(12) United States Patent
Iida et al.

(10) Patent No.: US 8,168,307 B2
(45) Date of Patent: May 1, 2012

(54) ORGANIC COMPOUND, CHARGE TRANSPORT MATERIAL AND ORGANIC ELECTROLUMINESCENT DEVICE

(75) Inventors: Koichiro Iida, Kanagawa (JP); Hideki Sato, Kanagawa (JP); Masayoshi Yabe, Kanagawa (JP); Masako Takeuchi, Kanagawa (JP)

(73) Assignees: Pioneer Corporation, Tokyo (JP); Mitsubishi Chemical Corporation, Tokyo (JP)

( * ) Notice: Subject to any disclaimer, the term of this patent is extended or adjusted under 35 U.S.C. 154(b) by 627 days.

(21) Appl. No.: 11/814,570

(22) PCT Filed: Jan. 19, 2006

(86) PCT No.: PCT/JP2006/300716
§ 371 (c)(1),
(2), (4) Date: Jul. 24, 2007

(87) PCT Pub. No.: WO2006/080229
PCT Pub. Date: Aug. 3, 2006

(65) Prior Publication Data
US 2009/0021146 A1    Jan. 22, 2009

(30) Foreign Application Priority Data
Jan. 25, 2005 (JP) .................................. 2005-017098

(51) Int. Cl.
*H01J 1/63* (2006.01)
*C09K 11/06* (2006.01)
*C07D 209/82* (2006.01)
*C07D 401/14* (2006.01)

(52) U.S. Cl. ........ 428/690; 428/917; 313/504; 546/256; 548/440

(58) Field of Classification Search .................. None
See application file for complete search history.

(56) References Cited

U.S. PATENT DOCUMENTS

| | | | |
|---|---|---|---|
| 2004/0086745 A1 | 5/2004 | Iwakuma et al. | |
| 2004/0110031 A1* | 6/2004 | Fukuda et al. | 428/690 |
| 2005/0127823 A1 | 6/2005 | Iwakuma et al. | |
| 2005/0249976 A1 | 11/2005 | Iwakuma et al. | |

FOREIGN PATENT DOCUMENTS

| | | |
|---|---|---|
| EP | 1 489 155 | 12/1922 |
| EP | 0 517 542 | 12/1992 |
| EP | 1 486 550 | 12/2004 |
| JP | 04-172357 | 6/1992 |
| JP | 4 172357 | 6/1992 |
| JP | 6 1972 | 1/1994 |
| JP | 2000-186066 | 7/2000 |
| JP | 2004-273190 | 9/2004 |
| JP | 2004 273190 | 9/2004 |
| KR | 10-2004-0094842 | 11/2004 |
| WO | 03 078541 | 9/2003 |
| WO | 03 080760 | 10/2003 |

OTHER PUBLICATIONS

Baldo, et al., "Very high-efficiency green organic light-emitting devices based on electrophosphorescence", Applied Physics Letters, vol. 75, No. 1, pp. 4-6, 1999.
Jian Pei, et al., "Structural Dependence of the Selectivity of Fluorescent Chemosensors to $Mg^{2+}$ form Alkali Earth Metal Ions", Macromolecular: Rapid Communications, XP009118214, vol. 23, No. 1, Jan. 1, 2002, pp. 21-25.
Office Action issued Mar. 11, 2011, in Korean Patent Application No. 10-2007-7017180.
Office Action issued Sep. 7, 2011, in Chinese Patent Application No. 200680002950.1 (with partial English-language translation).
Office Action mailed Jan. 17, 2012, in Japanese Patent Application No. 2006-011266, filed Jan. 19, 2006.
English translation of Office Action mailed Jan. 17, 2012, in Japanese Patent Application No. 2006-011266, filed Jan. 19, 2006.

* cited by examiner

*Primary Examiner* — Lynda Salvatore
*Assistant Examiner* — Andrew K Bohaty
(74) *Attorney, Agent, or Firm* — Oblon, Spivak, McClelland, Maier & Neustadt, L.L.P.

(57) ABSTRACT

An organic compound is represented by following Formula (I):

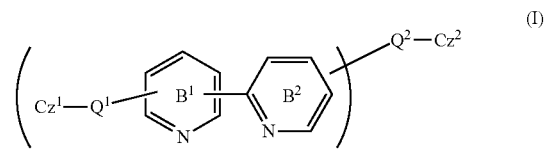

wherein $Cz^1$ and $Cz^2$ may be the same as or different from each other and each represent a carbazolyl group; $Q^1$ and $Q^2$ may be the same as or different from each other and each represent a direct bond or an arbitrary linkage group; and $Cz^1$, $Cz^2$, $Q^1$, $Q^2$, Ring $B^1$ and Ring $B^2$ may each be substituted. The organic compound and charge transporting material show both excellent hole transporting ability and excellent electron transporting ability and have satisfactory durability against electric oxidation/reduction and a high triplet excitation level. An organic electroluminescent device using the organic compound emits light with a high efficiency and is highly stably driven.

15 Claims, 2 Drawing Sheets

[Fig.1]
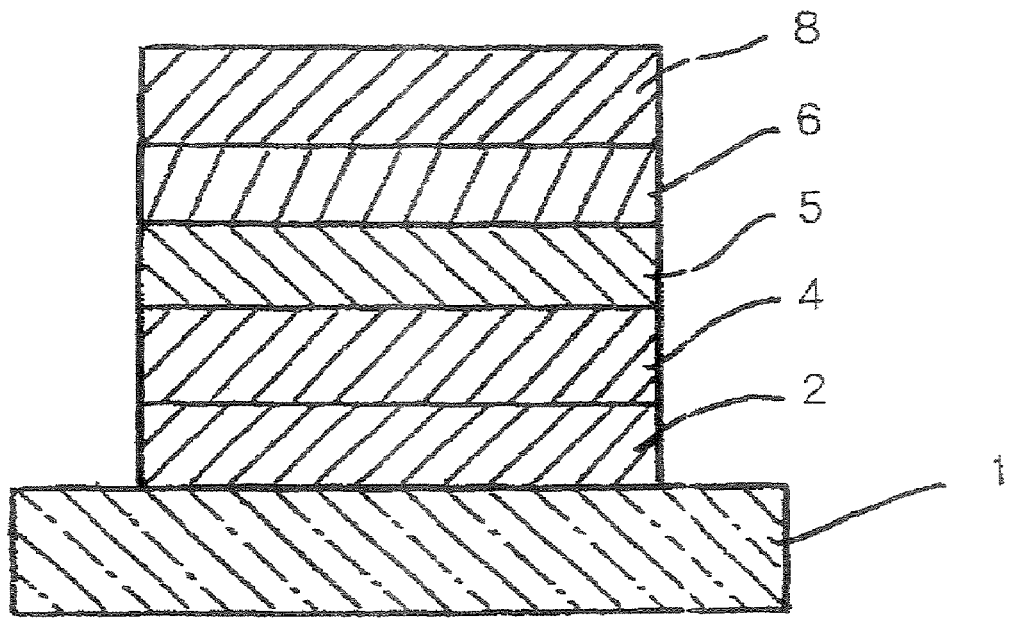
[Fig.2]
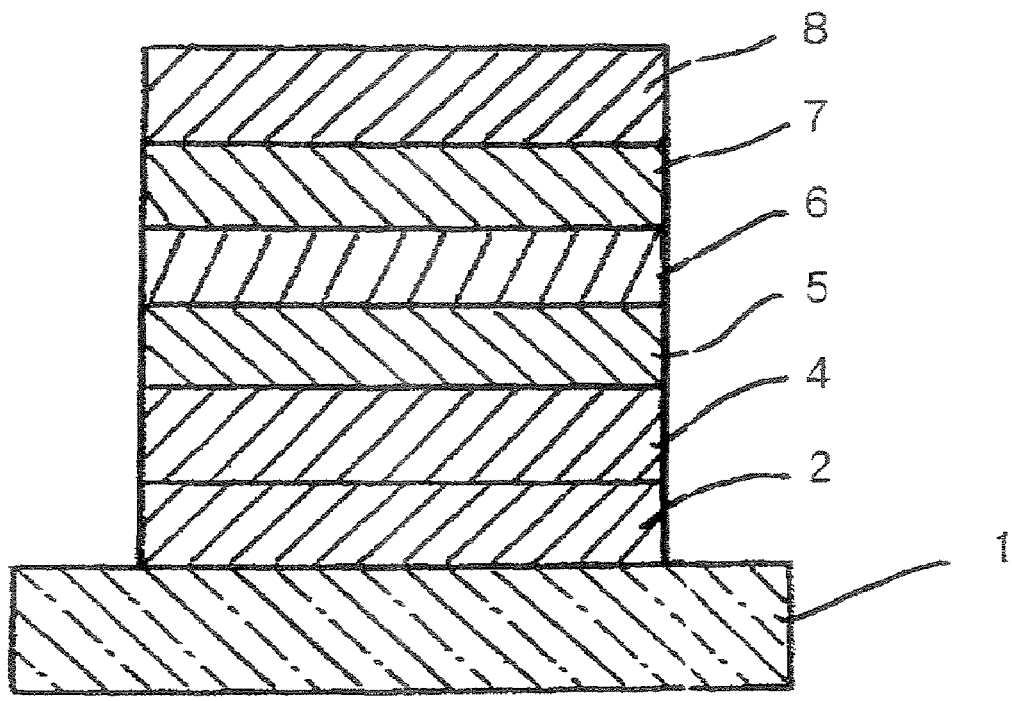

[Fig.3]
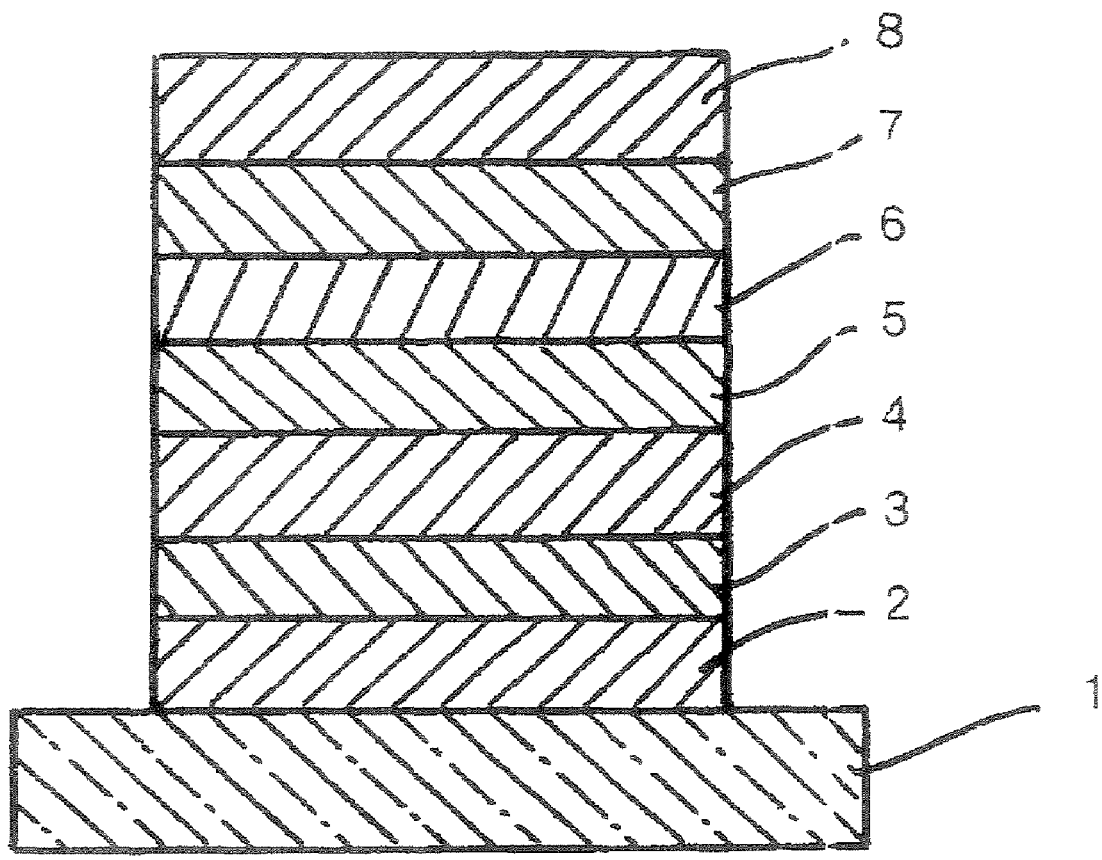

ORGANIC COMPOUND, CHARGE TRANSPORT MATERIAL AND ORGANIC ELECTROLUMINESCENT DEVICE

FIELD OF THE INVENTION

The present invention relates to organic compounds and charge transporting materials, and organic electroluminescent devices using the organic compounds.

BACKGROUND OF THE INVENTION

Electroluminescent devices using organic thin films, namely, organic electroluminescent devices each generally include a substrate bearing an anode, a cathode, and one or more organic layers including at least a light-emitting layer. The one or more organic layer are arranged between the two electrodes. Such organic layers may include a hole injection layer (anode buffer layer), a hole transport layer, a hole blocking layer, an electron transport layer, and an electron injection layer, in addition to a light-emitting layer. These layers are generally arranged or laminated between the anode and the cathode to constitute an organic electroluminescent device.

Organic electroluminescent devices have used fluorescent emission. As an attempt to raise luminous efficiency of the devices, it has also been examined to use phosphorescent emission instead of fluorescent emission. Sufficient luminous efficiency, however, has not yet been obtained even when phosphorescent emission is used.

Most of developed organic electroluminescent devices using phosphorescent molecules include materials containing carbazolyl group(s) as materials (host materials) for the light-emitting layer. For example, Non-patent Document 1 discloses, used as a host material, the following biphenyl derivative:

[Chemical Formula 1]

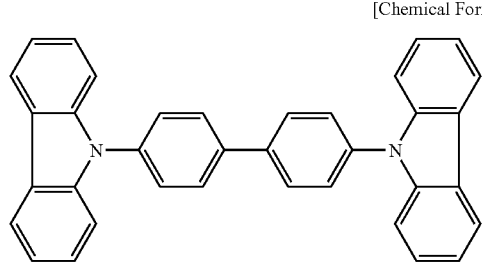

However, an organic electroluminescent device using the biphenyl derivative does not yield a satisfactorily high luminous efficiency, because the recombination of charge tends to occur unevenly in the vicinity of the cathode, and the device has poor balance in charge recombination.

Patent Document 1 mentioned below discloses an organic electroluminescent device using the following compound as a host material which enables a recombination region to concentrate in a light-emitting layer and has both hole transporting ability and electron transporting ability.

[Chemical Formula 2]

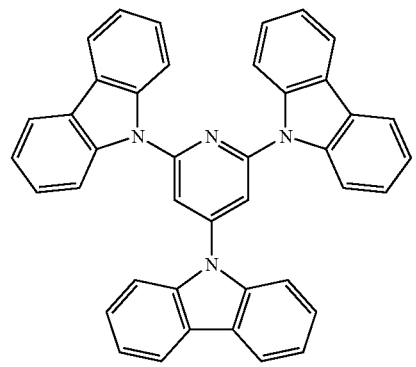

The device using the compound, however, shows light emission only under a high voltage and is insufficient in luminance and luminous efficiency. This is because the compound has only one pyridine ring, thereby shows a lowest unoccupied molecular orbital (LUMO) localized in the one pyridine ring, and shows a low electron transporting ability. In addition, the compound is insufficient in durability upon one-electron reduction.

Patent Document 2 proposes materials for use in organic electroluminescent devices typified by the following compounds:

[Chemical Formula 3]

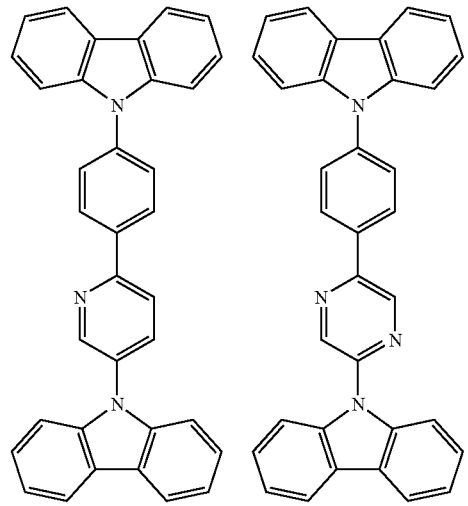

These compounds, however, each have only one pyridine ring or pyrazine ring and are susceptible to improvements in electron transporting ability and durability upon one-electron reduction, as described above. In this connection, compounds having a pyrazine ring and/or a pyrimidine ring each containing two or more nitrogen atoms per one ring may be not suitable as host materials, because they may have a lower triplet excitation level and lower durability upon one-electron reduction than compounds having a pyridine ring.

Patent Documents 2 and 3 propose materials for use in organic electroluminescent devices typified by the following compounds:

[Chemical Formula 4]

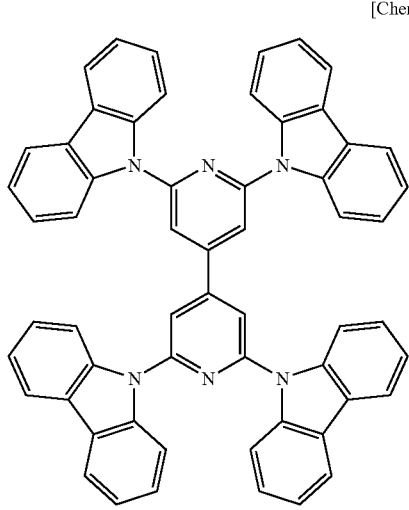

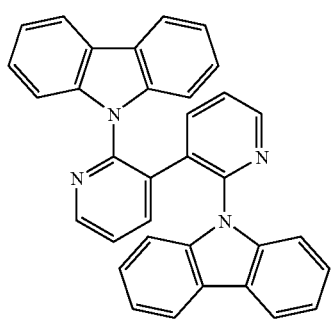

[Chemical Formula 5]

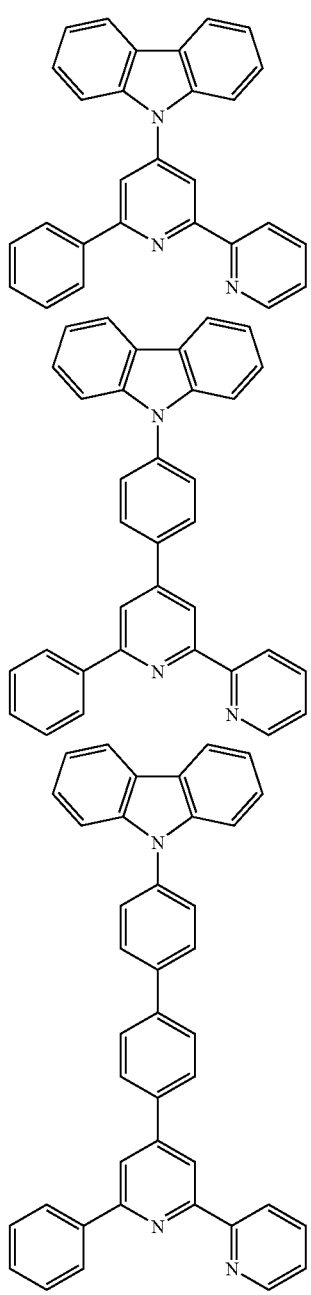

These compounds are supposed to have somewhat improved electron transporting ability, because they each have two pyridine rings directly bound to each other (bipyridyl skeleton) and show somewhat delocalized LUMO. These compounds, however, are still insufficient in electron transporting ability. This is because all the carbon atoms at the ortho positions with respect to the carbon atom in one pyridine ring directly bound to another pyridine ring are each bound to a hydrogen atom or a substituent in these compounds. Accordingly, the bipyridyl skeletons of these compounds are poor in planarity due to steric hindrance, and the compounds have still insufficient delocalized LUMO. In addition, the compounds are insufficient in durability upon one-electron reduction and fail to achieve a practically sufficient driving lifetime. This is because the compounds are resistant to increase in planarity of the bipyridyl skeleton, but such a bipyridyl skeleton is to have increased planarity upon one-electron reduction.

Patent Documents 2 and 4 propose materials for use in organic electroluminescent devices typified by the following compounds:

Although these compounds are expected to have improved electron transporting ability and durability upon one-electron reduction, they are not well balanced in between hole transporting ability and electron transporting ability as materials for light-emitting layers of organic electroluminescent devices and are still susceptible to improvements as host materials.

Patent Document 1: Japanese Unexamined Patent Application Publication No. 6-1972

Patent Document 2: PCT International Publication Number WO 03/078541

Patent Document 3: Japanese Unexamined Patent Application Publication No. 2004-273190

Patent Document 4: PCT International Publication Number WO 03/080760

Non-patent Document 1: Appl. Phys. Lett., vol. 75, p. 4, 1999

SUMMARY OF THE INVENTION

Accordingly, an object of the present invention is to provide an organic compound and a charge transporting material which exhibit both excellent hole transporting ability and excellent electron transporting ability, show satisfactory durability against electric oxidation/reduction, and have a high triplet excitation level. Another object of the present invention is to provide an organic electroluminescent device which uses the organic compound, emits light with a high efficiency, and is highly stably driven.

According to a first aspect of the present invention, there is provided an organic compound represented by following Formula (I).

According to a second aspect of the present invention, there is provided a charge transporting material which includes the organic compound according to the first aspect.

There is also provided, according to a third aspect of the present invention, an organic electroluminescent device including a substrate bearing an anode, a cathode, and an organic light-emitting layer arranged between the two electrodes, wherein the organic electroluminescent device further includes a layer containing the organic compound according to the first aspect between the anode and the cathode.

[Chemical Formula 6]

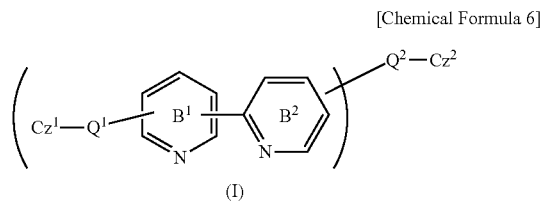

(I)

In formula (I), $Cz^1$ and $Cz^2$ may be the same as or different from each other and each represent a carbazolyl group;

$Q^1$ and $Q^2$ may be the same as or different from each other and each represent a direct bond or an arbitrary linkage group; and $Cz^1$, $Cz^2$, $Q^1$, $Q^2$, Ring $B^1$, and Ring $B^2$ may each be substituted.

BRIEF DESCRIPTION OF THE DRAWINGS

FIG. 1 is a schematic cross-sectional view showing an organic electroluminescent device according to an embodiment of the present invention.

FIG. 2 is a schematic cross-sectional view showing an organic electroluminescent device according to another embodiment of the present invention.

FIG. 3 is a schematic cross-sectional view showing an organic electroluminescent device according to yet another embodiment of the present invention.

DETAILED DESCRIPTION OF THE PREFERRED EMBODIMENTS

An organic compound according to the first aspect has a high triplet excitation level, exhibits excellent charge transporting abilities (hole transporting ability and electron transporting ability), and has excellent durability against electric oxidation/reduction. Accordingly, an organic electroluminescent device using this organic compound can emit light with a high luminance and a high efficiency, is more stable, is driven highly stably, and has a longer lifetime.

The organic electroluminescent device according to the third aspect using the organic compound according to the first aspect can supposedly be applied to a flat panel display (e.g., for office automation (OA) computers or as a wall-hanging television), an onboard display device, display for a cellular phone, a light source utilizing the characteristics as a flat light-emitting device (e.g., a light source for a copying machine or a backlight source for a liquid crystal display or a meter), an indication panel, or a beacon light. The device thereby has a significant technical value.

The organic compound according to the first aspect inherently shows excellent oxidation/reduction stability and can thereby be advantageously applied to an electrophotographic photoreceptor, in addition to an organic electroluminescent device.

The organic compound is useful for a light-emitting material; a material for solar cell; a material for a battery, such as an electrolytic solution, an electrode, a separation membrane or a stabilizer; a material for medical use; a material for paint; a material for coating; a material for organic semi-conductor; a material for toiletries; a material for antistatic material; and a material for thermoelectric device; as well as for a charge transporting material.

A charge transporting material according to the second aspect can be used typically as a hole injecting material, a hole transporting material, a light-emitting material, a host material, an electron injecting material, or an electron transporting material depending upon the layer structure of the device based on its excellent filming properties, charge transporting ability, light-emitting properties, and thermal stability.

Some preferred embodiments of organic compounds, charge transporting materials, and organic electroluminescent devices according to the present invention will be illustrated in detail below.

[Organic Compounds]

Organic compounds according to the first aspect are represented by Formula (I).

[1] STRUCTURAL CHARACTERISTICS

An organic compound according to the present invention represented by Formula (I) has excellent durability against oxidation/reduction and includes a moiety mainly bearing an electron transporting activity and a moiety mainly bearing a hole transporting activity in good balance.

The moiety Ring $B^1$-Ring $B^2$ serves as a moiety mainly bearing an electron transporting activity and constitutes a bipyridyl skeleton having high planarity, because neither hydrogen atom nor substituent is combined with the nitrogen atom in Ring $B^2$, and there is a small steric hindrance between Ring $B^1$ and Ring $B^2$. The LUMO is thereby sufficiently delocalized on the moiety Ring $B^1$-Ring $B^2$, and the organic compound exhibits excellent electron transporting ability. In addition, the organic compound is excellent in durability upon one-electron reduction, because it has a small structural change between the ground state and a state after one-electron reduction.

The organic compound according to the present invention has above mentioned characteristics and, when it is applied to an organic electroluminescent device, the device can be driven at a lower drive voltage with an increased stability.

An organic compound according to the present invention has two or more carbazolyl groups each serving as a moiety mainly bearing a hole transporting activity, as in the moieties $Cz^1$-$Q^1$- and $Cz^2$-$Q^2$-. The organic compound thereby has excellent hole transporting ability. Accordingly, an organic electroluminescent device using the organic compound can be driven at a lower drive voltage, and positive and negative charges necessary for the recombination of a hole and an electron in a light-emitting layer can be easily fed in good balance.

[2] COMPONENTS IN FORMULA (I)

<Ring $B^1$ and Ring $B^2$>

Ring $B^1$ and Ring $B^2$ are each a pyridine ring and may each independently have an arbitrary substituent in addition to $Cz^1$-$Q^1$- or $Cz^2$-$Q^2$-. In this connection, Ring $B^2$ is not always substituted with $Cz^2$-$Q^2$-.

A partial structure represented by following Formula (I') is a partial structure of Formula (I) and can be any of partial structures represented by following Formulae (III-1), (III-2), and (III-3). Of these, partial structures represented by Formulae (III-1) and Formula (III-2) are preferred from the viewpoint of delocalization of LUMO, of which a partial structure represented by Formula (III-1) is more preferred for high planarity, excellent electron transporting ability, and excellent durability against reduction.

[Chemical Formula 7]

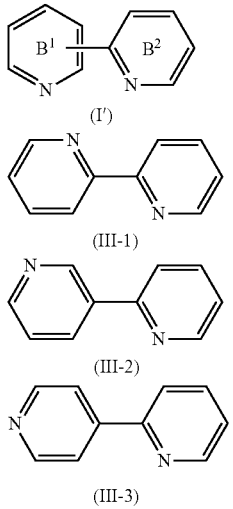

Examples of substituents which Ring $B^1$ and/or Ring $B^2$ may have include alkyl groups, aromatic hydrocarbon groups, acyl groups, alkoxy groups, aryloxy groups, alkylthio groups, arylthio groups, alkoxycarbonyl groups, aryloxycarbonyl groups, halogen atoms, arylamino groups, alkylamino groups, and aromatic heterocyclic groups. Among them, preferred are alkyl groups, aromatic hydrocarbon groups, and aromatic heterocyclic groups, of which more preferred are monovalent groups derived from monocyclic six-membered rings or from condensed rings having condensed two to five six-membered rings, such as benzene ring, naphthalene ring, anthracene ring, phenanthrene ring, perylene ring, tetracene ring, pyrene ring, benzopyrene ring, chrysene ring, triphenylene ring, fluoranthene ring, and carbazole ring; and monovalent groups each containing two or more of these combined with each other, such as biphenyl group and terphenyl group. Of these, phenyl group, 4-biphenyl group, 3-carbazolylphenyl group, 4-carbazolylphenyl group, and N-carbazolyl group are especially preferred.

When Ring $B^1$ and/or Ring $B^2$ has a substituent, the substituent is preferably substituted at the meta position or the para position with respect to a carbon atom directly bound to another pyridine ring. When Ring $B^2$ has a substituent, for example, it preferably has the substituent at any one of the 4-, 5-, and 6-positions.

Specifically, up to five substituents including $Cz^1$-$Q^1$- and $Cz^2$-$Q^2$- can be substituted on each of Ring $B^1$ and Ring $B^2$. However, Ring $B^1$ and Ring $B^2$ preferably do not have a substituent at the ortho position with respect to the carbon atom directly bound to another pyridine ring. If a ring has a substituent at the ortho position with respect to the carbon atom directly bound to another pyridine ring, the ring shows a larger steric hindrance and has lower electron transporting ability and durability against reduction than a ring having no substituent (i.e., having hydrogen atom) at the ortho position.

However, it is preferred that Ring $B^1$ and Ring $B^2$ have no other substituent than $Cz^1$-$Q^1$- and $Cz^2$-$Q^2$- or have a phenyl group and/or a 3-carbazolylphenyl group as a substituent. Ring $B^1$ and Ring $B^2$ more preferably have no other substituent than $Cz^1$-$Q^1$- and $Cz^2$-$Q^2$-.

Specifically, when Ring $B^1$ and/or Ring $B^2$ has one or more substituents in addition to $Cz^1$-$Q^1$- and $Cz^2$-$Q^2$-, the ring may show decreased electron transporting ability upon one-electron reduction due to blockage of negative charge, as compared with a ring substituted with $Cz^1$-$Q^1$- and $Cz^2$-$Q^2$- alone. Accordingly, it is preferred that at least one of Ring $B^1$ and Ring $B^2$ has no other substituent than $Cz^1$-$Q^1$- and $Cz^2$-$Q^2$-, and it is more preferred that both Ring $B^1$ and Ring $B^2$ have no other substituent than $Cz^1$-$Q^1$- and $Cz^2$-$Q^2$-.

<$Cz^1$ and $Cz^2$>

$Cz^1$ and $Cz^2$ each represent a carbazolyl group.

$Cz^1$ and $Cz^2$ may be the same as or different from each other.

Examples of $Cz^1$ and $Cz^2$ include N-carbazolyl group, 1-carbazolyl group, 2-carbazolyl group, 3-carbazolyl group, and 4-carbazolyl group. Among them, N-carbazolyl group and 2-carbazolyl group are preferred, and N-carbazolyl group is most preferred from the viewpoint of yielding a high triplet excitation level and excellent electrochemical stability.

When $Cz^1$ and $Cz^2$ in Formula (I) are N-carbazolyl groups, Formula (I) is represented by following Formula (I-4):

[Chemical Formula 8]

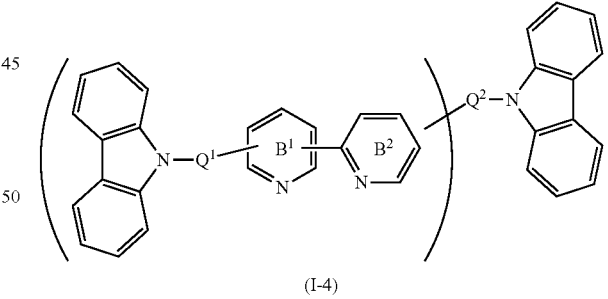

$Cz^1$ and $Cz^2$ may each independently have one or more arbitrary substituents.

Preferred examples of the substituents include alkyl groups, aromatic hydrocarbon groups, acyl groups, alkoxy groups, aryloxy groups, alkylthio groups, arylthio groups, alkoxycarbonyl groups, aryloxycarbonyl groups, halogen atoms, arylamino groups, alkylamino groups, and aromatic heterocyclic groups, of which alkyl groups, aromatic hydrocarbon groups, and aromatic heterocyclic groups are more preferred.

For yielding a high triplet excitation level and for avoiding decrease in electric resistance due to deviation of charge distribution, the substituents herein are preferably monovalent groups derived from monocyclic six-membered rings or from condensed rings having condensed two to five six-membered rings, such as benzene ring, naphthalene ring, anthracene ring, phenanthrene ring, perylene ring, tetracene ring, pyrene ring, benzopyrene ring, chrysene ring, triphenylene ring, and fluoranthene ring; and monovalent groups each containing two or more of these groups combined with each other, such as biphenylenyl group and terphenylenyl group.

The total molecular weight of substituents on each of $Cz^1$ and $Cz^2$ is preferably 500 or less and more preferably 250 or less. Most preferably, $Cz^1$ and $Cz^2$ are unsubstituted.

An organic compound according to the present invention preferably has all the carbazolyl groups in the molecule being N-carbazolyl groups represented by following Formula (II):

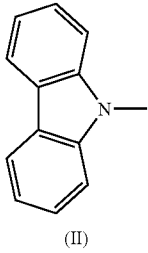

[Chemical Formula 9]

(II)

<$Q^1$ and $Q^2$>

$Q^1$ and $Q^2$ each represent a direct bond or an arbitrary linkage group.

$Q^1$ and $Q^2$ may be the same as or different from each other.

Preferred examples of the arbitrary linkage group include bivalent linkage groups derived from monocyclic six-membered rings or from condensed rings having condensed two to five six-membered rings, such as benzene ring, naphthalene ring, anthracene ring, phenanthrene ring, perylene ring, tetracene ring, pyrene ring, benzopyrene ring, chrysene ring, triphenylene ring, and fluoranthene ring; and bivalent linkage groups each including two or more of these groups combined with each other, such as biphenylene group and terphenylene group. $Q^1$ and $Q^2$ are each preferably a direct bond or a bivalent linkage group containing one to eight benzene rings combined with each other, such as phenylene group, biphenylene group, or terphenylene group.

When $Q^1$ and $Q^2$ are each an arbitrary linkage group, and $Q^2$ may each independently have one or more arbitrary substituents. Preferred examples of the substituents include alkyl groups, aromatic hydrocarbon groups, acyl groups, alkoxy groups, aryloxy groups, alkylthio groups, arylthio groups, alkoxycarbonyl groups, aryloxycarbonyl groups, halogen atoms, arylamino groups, alkylamino groups, and aromatic heterocyclic groups, of which alkyl groups, aromatic hydrocarbon groups, and aromatic heterocyclic groups are more preferred. Among them, particularly preferred are monovalent groups derived from monocyclic six-membered rings or from condensed rings having condensed two to five six-membered rings, such as benzene ring, naphthalene ring, anthracene ring, phenanthrene ring, perylene ring, tetracene ring, pyrene ring, benzopyrene ring, chrysene ring, triphenylene ring, and fluoranthene ring; and monovalent groups each containing two or more of these groups combined with each other, such as biphenylenyl group and terphenylenyl group.

The molecular weight of each of $Q^1$ and $Q^2$ is preferably 1000 or less, and more preferably 500 or less.

$Q^1$ and $Q^2$ are each typically preferably a direct bond or -$(Ph)_p$-, wherein Ph represents a phenylene group which may be substituted; and "p" represents an integer of from 1 to 8 and is preferably an integer of from 1 to 3. Such substituents which the phenylene group may have are as with those exemplified as substituents for $Q^1$ and $Q^2$.

In Formula (I), $Q^2$ may be combined with any one of Ring $B^1$, Ring $B^2$, $Q^1$, and $Cz^1$.

<$Cz^1$-$Q^1$- and $Cz^2$-$Q^2$->

While $Cz^1$, $Cz^2$, $Q^1$, and $Q^2$ have been described above, preferred combinations of $Cz^1$ with $Q^1$, and of $Cz^2$ with $Q^2$ will be illustrated below.

Preferred embodiments of $Cz^1$-$Q^1$- and $Cz^2$-$Q^2$- are following embodiments [1] to [3]:

[1] $Cz^1$-$Q^1$- and $Cz^2$-$Q^2$- are each preferably represented by following Formula (IV-1). Hereinafter, $Cz^1$-$Q^1$- and $Cz^2$-$Q^2$- are generically referred to as Cz-Q-.

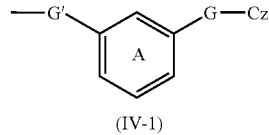

[Chemical Formula 10]

(IV-1)

In Formula (IV-1), Cz represents $Cz^1$ or $Cz^2$;

Ring A represents a benzene ring which may be substituted;

G and G' may be the same as or different from each other, each represent direct bond or an arbitrary linkage group, and may each be substituted.

In an organic compound having Cz-Q- moieties represented by Formula (IV-1), a moiety mainly bearing a hole transporting activity (carbazolyl group) and a moiety mainly bearing an electron transporting activity (bipyridyl skeleton) are combined through benzene ring at the meta position. The organic compound having Cz-Q- moieties represented by Formula (IV-1) has excellent electrochemical stability, excellent thermal stability, and a high triplet excitation level. These properties are derived from excellent thermal stability, excellent electrochemical stability, and a high triplet excitation level of the benzene ring. In addition, in the organic compound having partial structures Cz-Q- represented by Formula (IV-1), such a benzene ring having substituents at the meta-positions has both electron accepting ability and electron donating ability and, where necessary, serves to receive part of positive charges upon reduction of the carbazolyl group and to receive part of negative charges upon reduction of Rings $B^1$ and $B^2$. Thus, the organic compound having Cz-Q- moieties represented by Formula (IV-1) exhibits further improved durability against oxidation/reduction.

G and G' in Formula (IV-1) are each a part of Q in Formula (I), and preferred examples thereof and substituents which G and G' may have are as with those described in $Q^1$ and $Q^2$ in Formula (I).

Ring A in Formula (IV-1) is a part of $Q^1$ or $Q^2$ in Formula (I), and examples of substituents which Ring A may have are as with those mentioned in $Q^1$ and $Q^2$ in Formula (I).

The molecular weight of the partial structure represented by Formula (IV-1) is preferably 2000 or less, and more preferably 1000 or less.

When partial structures $Cz^1$-$Q^1$- and $Cz^2$-$Q^2$- are represented by Formula (IV-1), an organic compound according to the present invention is preferably represented by following Formula (I-1):

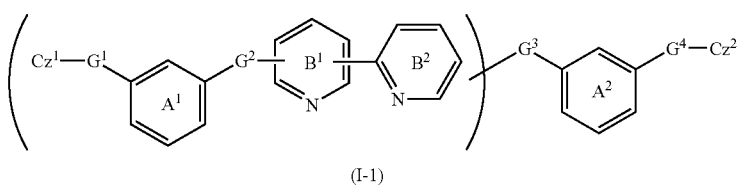

(I-1)

wherein $G^1$, $G^2$, $G^3$, and $G^4$ are each defined as with G or G' in Formula (IV-1), each represent a direct bond or an arbitrary linkage group, and may be the same as or different from one another;

Ring $A^1$ and Ring $A^2$ are each defined as with Ring A in Formula (IV-1), each represent a benzene ring, and may each be substituted; and $Cz^1$, $Cz^2$, Ring $B^1$ and Ring $B^2$ are as defined in Formula (I).)

$Cz^1$-$Q^1$- and $Cz^2$-$Q^2$- are preferably combined to form a partial structure represented by following Formula (IV-2):

[Chemical Formula 12]

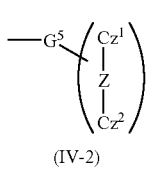

(IV-2)

wherein $Cz^1$ and $Cz^2$ are as defined in Formula (I);

$G^5$ represents a direct bond or an arbitrary linkage group;

Z represents an arbitrary linkage group enabling the conjugation of nitrogen atoms on $Cz^1$ and $Cz^2$ with each other; and $G^5$ and Z may each be substituted.

It is important that $Cz^1$ and $Cz^2$ are represented by Formula (IV-2), namely, that nitrogen atoms on the two carbazolyl groups are capable of conjugating with each other through the linkage group Z.

Specifically, when two or more carbazolyl groups are combined with one aromatic hydrocarbon group (the aromatic hydrocarbon group in this case includes a group containing two or more rings combined with each other, such as biphenyl group), it is undesirable that nitrogen atoms on the two or more carbazolyl groups are non-conjugated. This is because excess positive electric charges concentrate on the aromatic hydrocarbon group or positive electric charges are more intensively localized on at least one of the N-, 1-, 3-, 6-, and 8-positions of the carbazolyl groups upon electric oxidation. Thus, the durability against electric oxidation may significantly decrease.

In contrast, when two or more carbazolyl groups are combined to one aromatic hydrocarbon group (the aromatic hydrocarbon group in this case includes a group containing two or more rings combined with each other, such as biphenyl group), it is desirable that nitrogen atoms on the two or more carbazolyl groups are capable of conjugating with each other. This is because positive electric charges are relatively uniformly distributed on the aromatic hydrocarbon group and the two carbazolyl groups, which contributes to excellent durability upon one-electron oxidation.

The phrase "nitrogen atoms are capable of conjugating with each other" has the same meaning as that the nitrogen atoms are connected to each other through a partial structure represented by:

[Chemical Formula 13]

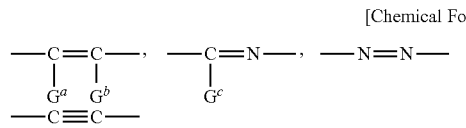

wherein either of cis- and trans-form will do, and wherein $G^a$, $G^b$, and $G^c$ each independently represent a hydrogen atom or an arbitrary substituent, or constitute a part of an aromatic hydrocarbon ring or an aromatic heterocyclic ring, or any combination of these partial structures.

The total number of substituents, including $Cz^1$ and $Cz^2$, on the linkage group Z is preferably 2 to 5, more preferably 2 or 4, and most preferably 2.

Z in Formula (IV-1) is a part of $Q^1$ or $Q^2$ in Formula (I), and specific examples thereof and examples of substituents which Z may have are as with those described in $Q^1$ and $Q^2$ in Formula (I). However, Z is an arbitrary linkage group enabling the conjugation of nitrogen atoms on $Cz^1$ and $Cz^2$ with each other.

Examples of the partial structure represented by Formula (IV-2) including Z are as follows.

[Chemical Formula 14]

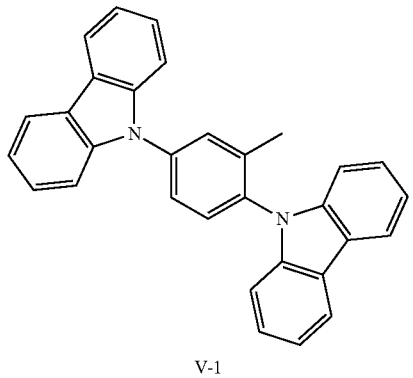

V-1

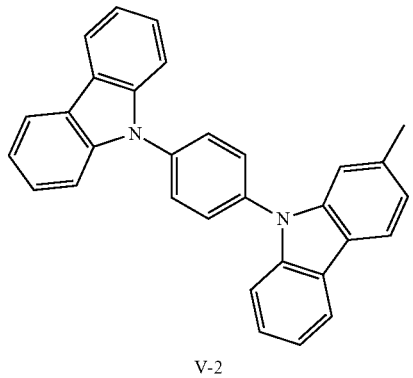

V-2

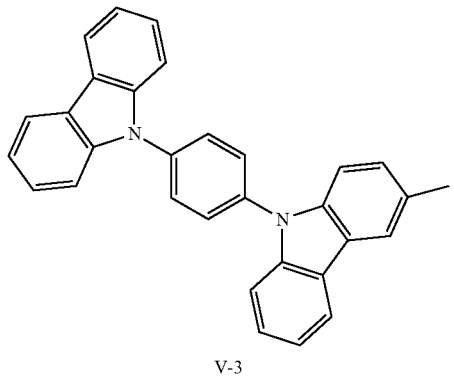
V-3
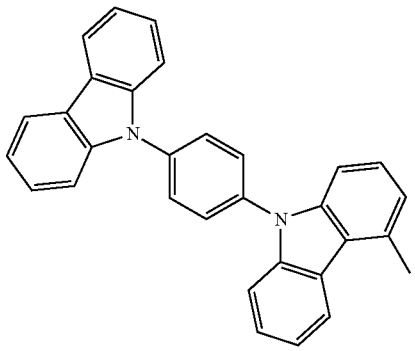
V-4
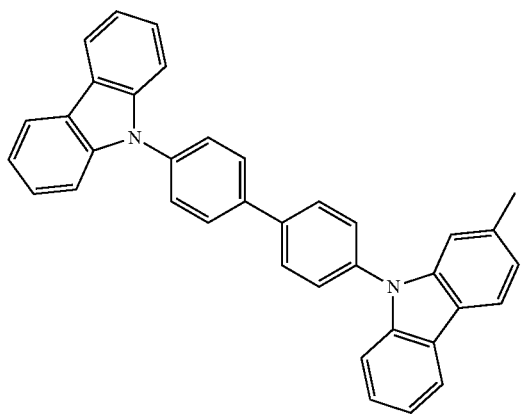
V-5
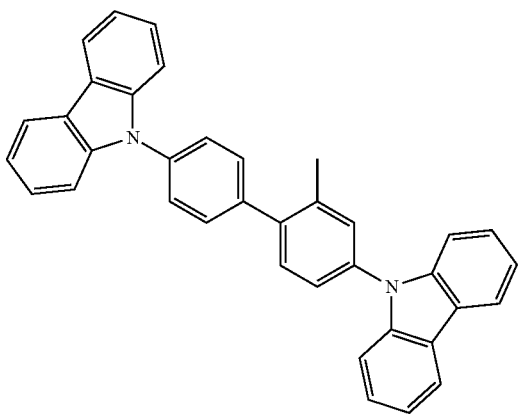
V-6
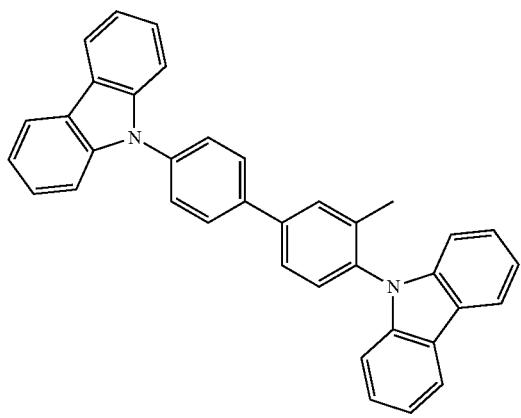
V-7
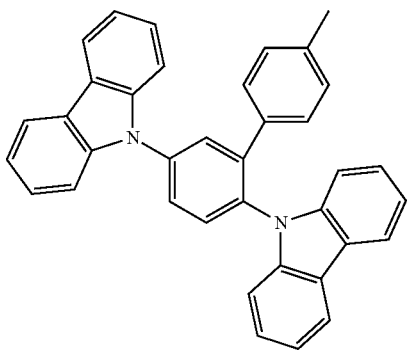
V-8
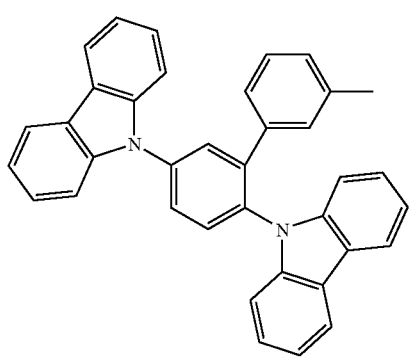
V-9

-continued
[Chemical Formula 15]
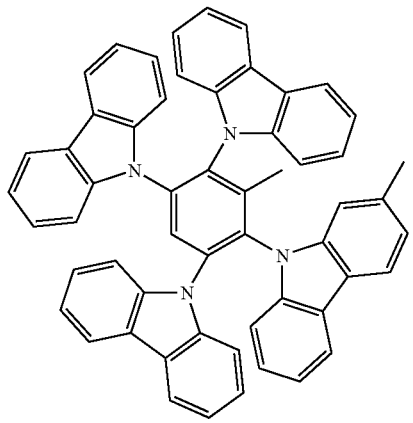
V-10
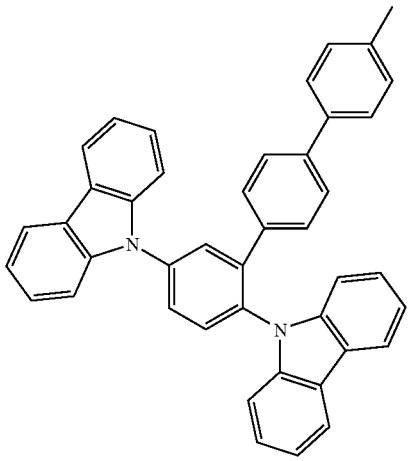
V-11
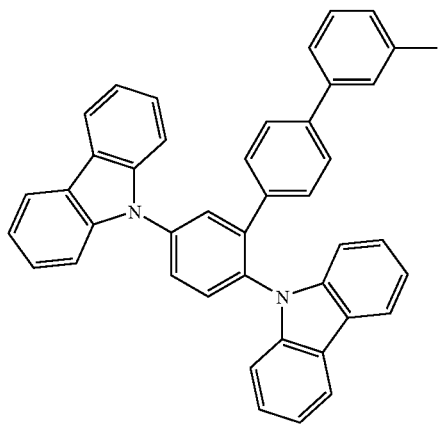
V-12
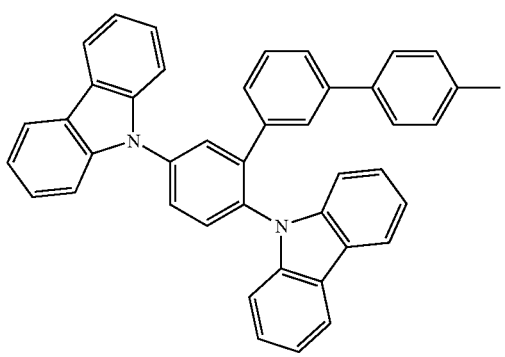
V-13
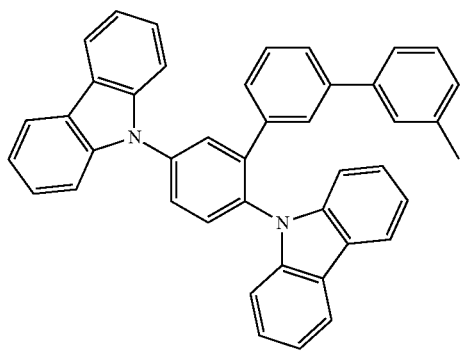
V-14
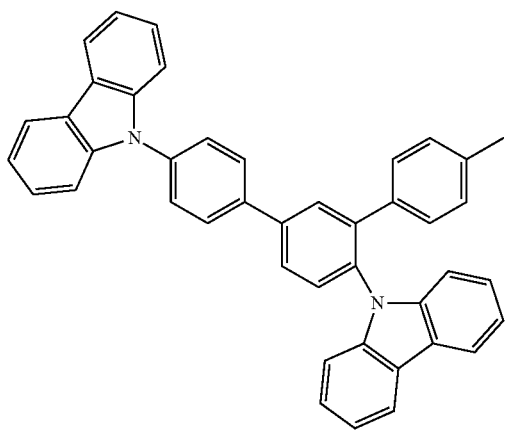
V-15

-continued
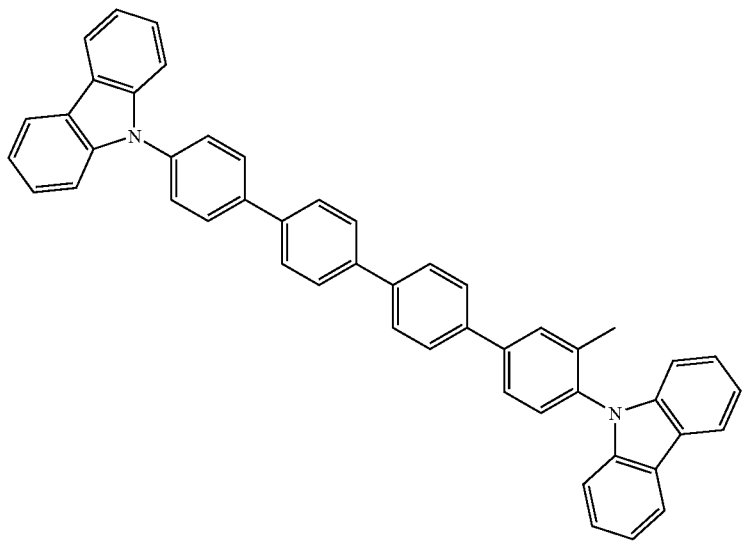
V-16
[Chemical Formula 16]
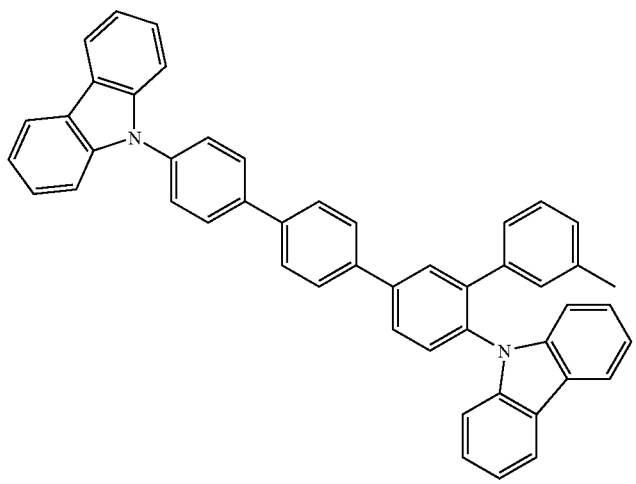
V-17
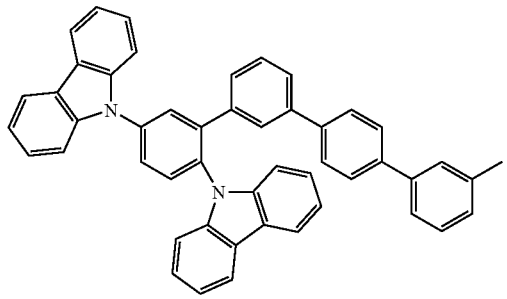
V-18
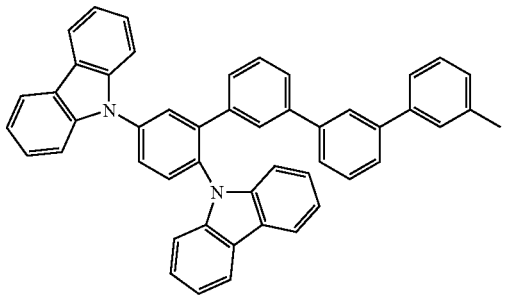
V-19

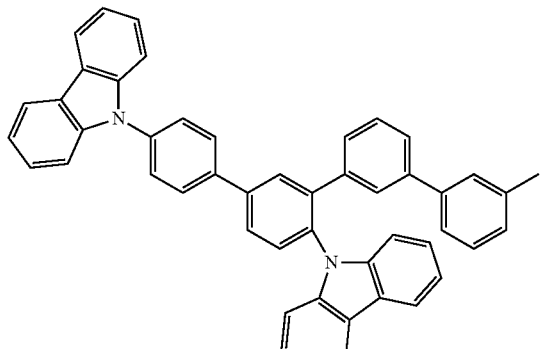
V-20
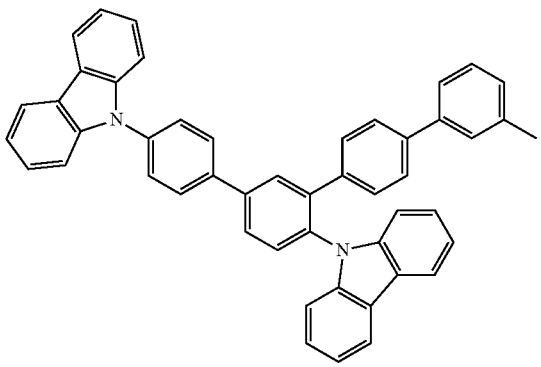
V-21
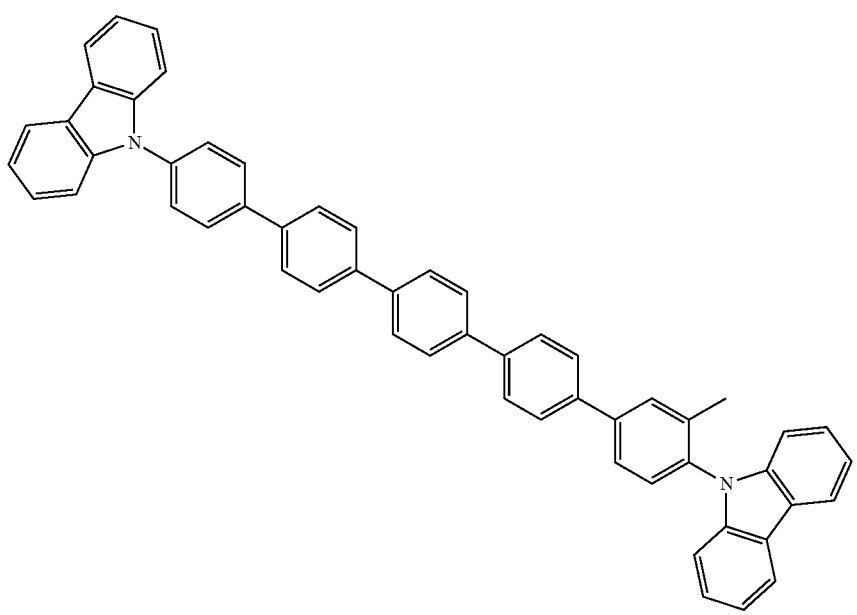
V-22
[Chemical Formula 17]
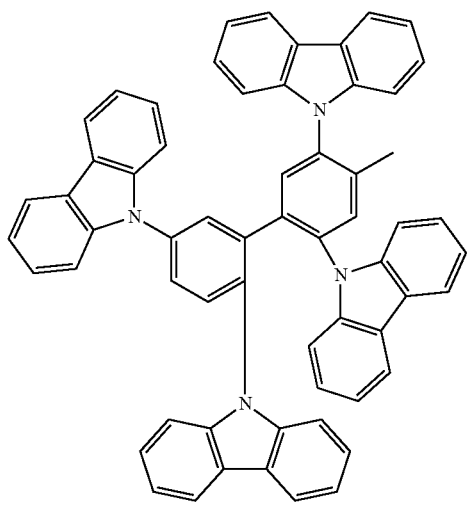
V-23
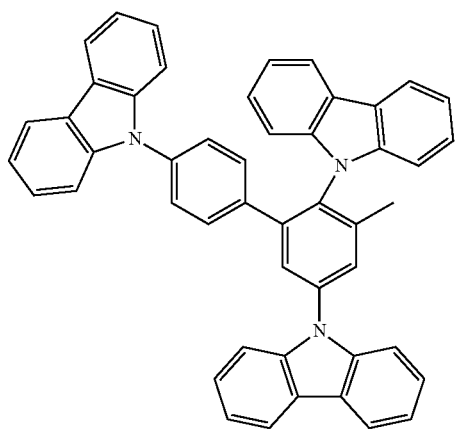
V-24

-continued
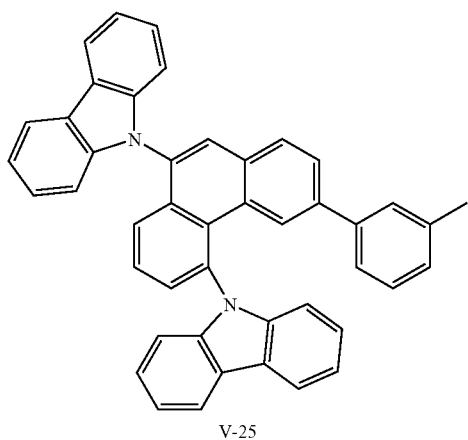
V-25
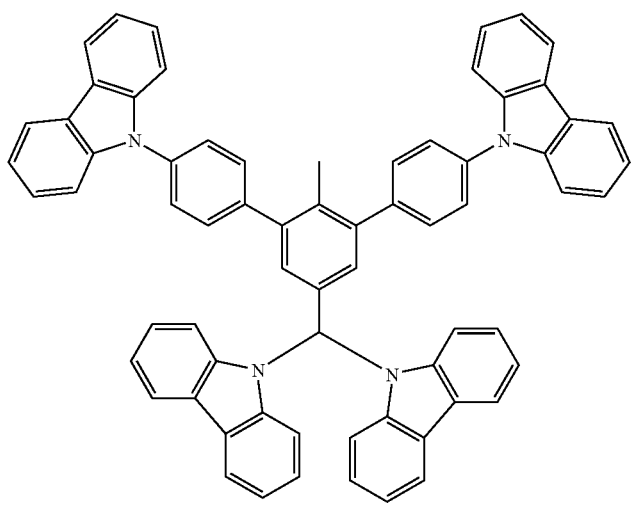
V-26
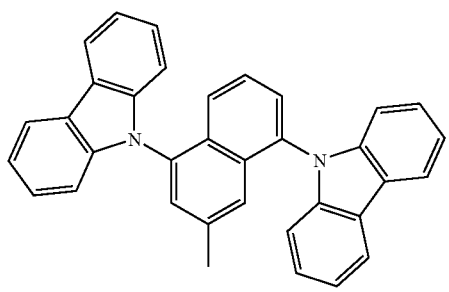
V-27
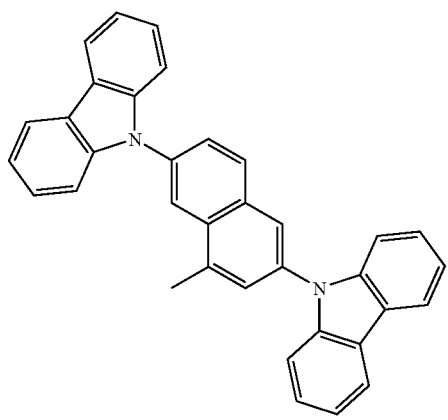
V-28

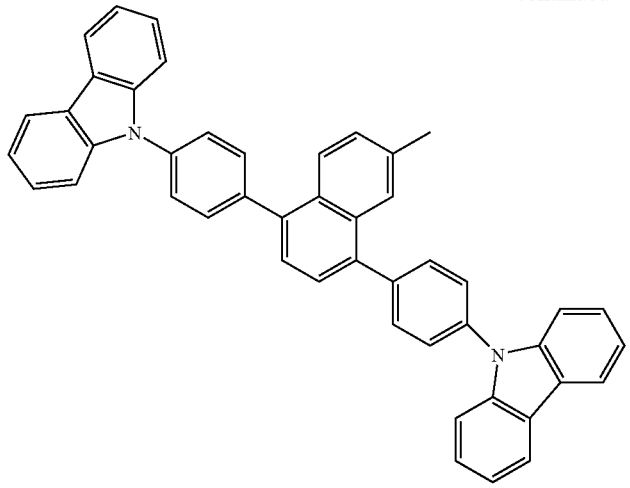

V-29

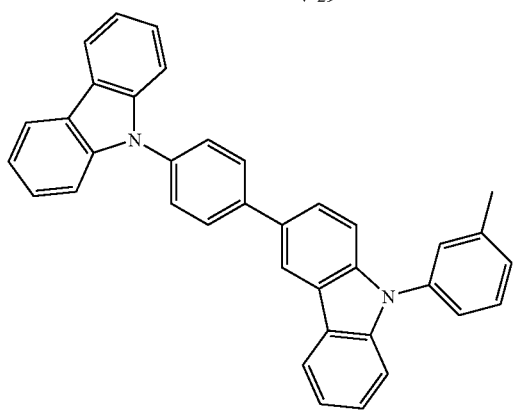

V-30

Of the exemplified partial structures, the partial structures V-1, V-2, V-4 to V-15, V-17 to V-21, V-27, and V-28 are preferred, the partial structures V-1, V-6 to V-9, V-11 to V-15 are more preferred, and the partial structure V-1 is most preferred.

$G^5$ in Formula (IV-2) is a part of $Q^1$ or $Q^2$ in Formula (I), and preferred examples thereof and examples of substituents which $G^5$ may have are as with those described in $Q^1$ and $Q^2$ in Formula (I).

The molecular weight of the partial structure represented by Formula (IV-2) is preferably 3000 or less, and more preferably 1500 or less.

When the partial structures $Cz^1$-$Q^1$- and $Cz^2$-$Q^2$- are represented by Formula (IV-2), an organic compound according to the present invention is preferably represented by following Formula (I-2):

Z is defined as with Z in Formula (IV-2), represents an arbitrary linkage group enabling the conjugation of nitrogen atoms on $Cz^1$ and $Cz^2$ with each other, and may be substituted; and $Cz^1$, $Cz^2$, $Q^1$, Ring $B^1$, and Ring $B^2$ are as defined in Formula (I).

[3] It is also preferred that $Cz^1$-$Q^1$- and $Cz^2$-$Q^2$- are each directly bound to Rings $B^1$ and $B^2$.

In this case, an organic compound according to the present invention is preferably represented by following Formula (I-3). The resulting organic compound may have more widely distributed positive electric charges upon one-electron oxidation, show more excellent hole transporting ability and more easily have good balance with the excellent electron transporting ability owing to the bipyridyl skeleton.

[Chemical Formula 18]

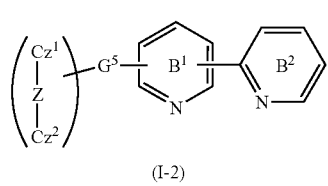

(I-2)

[Chemical Formula 19]

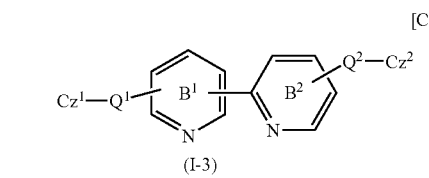

(I-3)

wherein $G^5$ is defined as with $G^5$ in Formula (IV-2) and represents a direct bond or an arbitrary linkage group;

In Formula (I-3), $Cz^1$, $Cz^2$, $Q^1$, $Q^2$, Ring $B^1$, and Ring $B^2$ are as defined in Formula (I).

[3] MOLECULAR WEIGHT

The molecular weight of an organic compound according to the present invention is generally 4000 or less, preferably 3000 or less, and more preferably 2000 or less and is generally 200 or more, preferably 300 or more, and more preferably 400 or more.

If an organic compound according to the present invention has a molecular weight exceeding the upper limit, the compound may have significantly decreased sublimability and may become difficult to form a satisfactory film by vapor deposition in the production of an electroluminescent device. Alternatively or in addition, the compound may contain impurities having higher molecular weights, and the compound may not be sufficiently purified. If an organic compound has a molecular weight lower than the lower limit, the compound may be decreased typically in glass transition temperature, melting point, and gasification temperature and may have significantly poor thermal stability.

[4] PHYSICAL PROPERTIES

An organic compound according to the present invention generally has a glass transition temperature of 50° C. or higher. When the organic compound is used in an organic electroluminescent device, the glass transition temperature is preferably 90° C. or higher and more preferably 110° C. or higher, from the viewpoint of yielding satisfactory thermal stability of the device. The upper limit of the glass transition temperature is generally about 400° C.

An organic compound according to the present invention generally has a gasification temperature of 800° C. or lower under normal pressure. When the organic compound is used in an organic electroluminescent device, the gasification temperature is preferably 700° C. or lower, and more preferably 600° C. or lower, for stably carrying out a film forming process by vapor deposition. The lower limit of the gasification temperature is generally about 300° C.

An organic compound according to the present invention generally has a melting point of 100° C. or higher. When the organic compound is used in an organic electroluminescent device, the melting point is preferably 150° C. or higher, and more preferably 200° C. or higher, for yielding satisfactory thermal stability of the device. The upper limit of the melting point is generally about 500° C.

[5] SPECIFIC EXAMPLES

Preferred examples of organic compounds according to the present invention will be illustrated below, which, however, are not limitative at all. In the following structural formulae, —N-Cz represents an N-carbazolyl group.

[Chemical Formula 20]

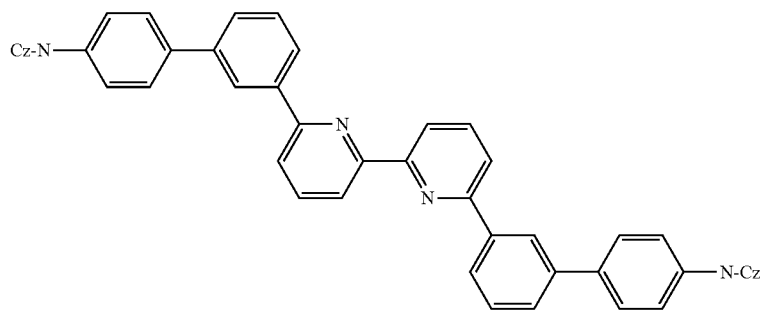

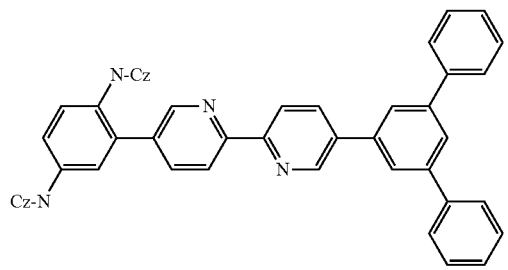

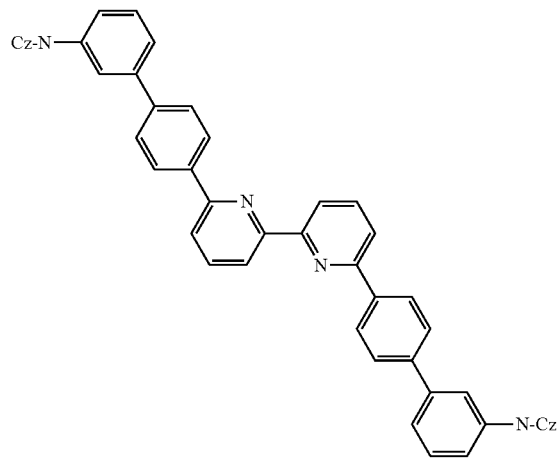

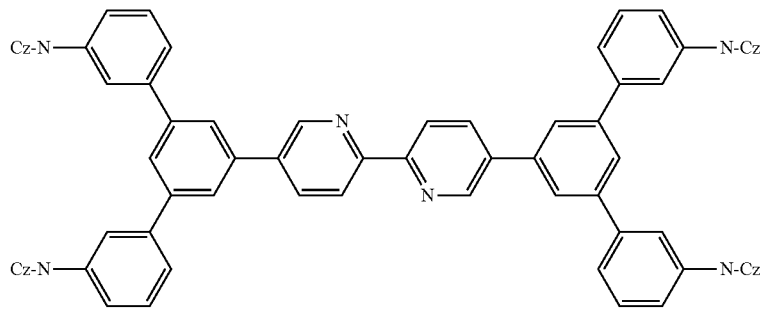
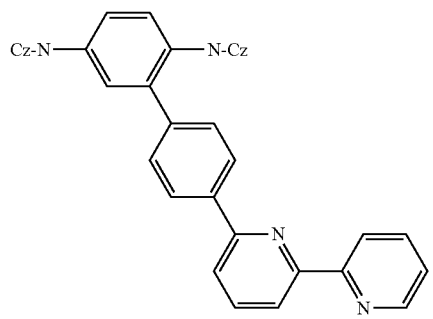
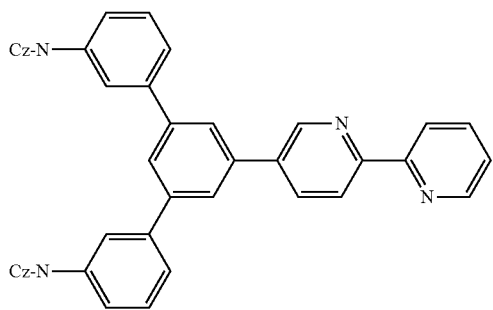
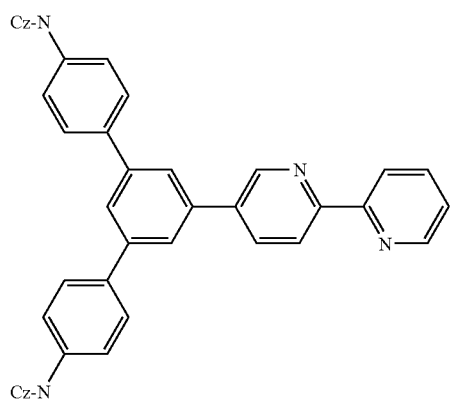
[Chemical Formula 21]
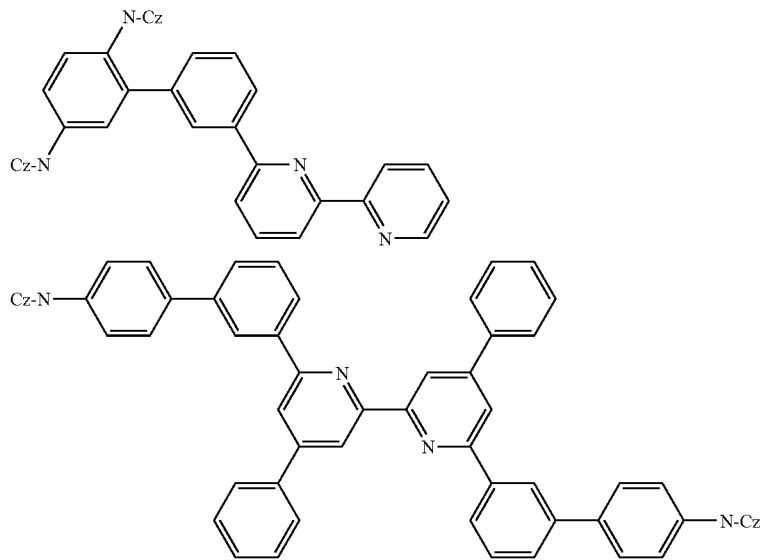

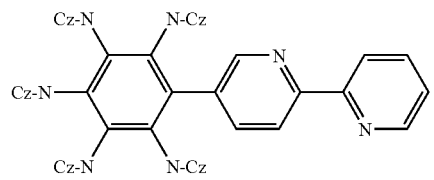
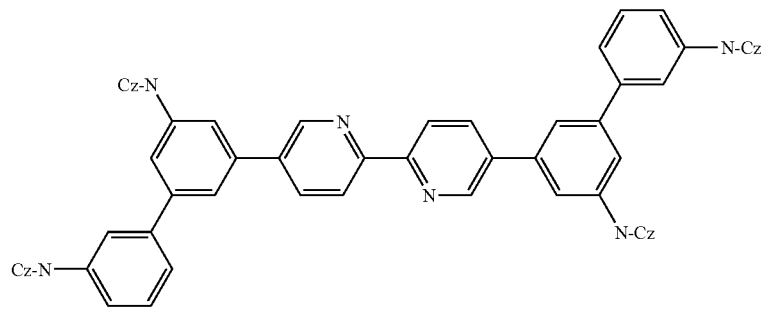
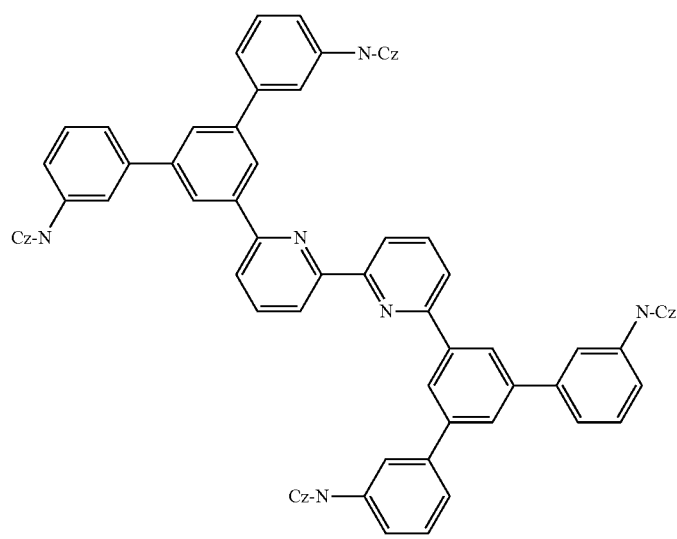
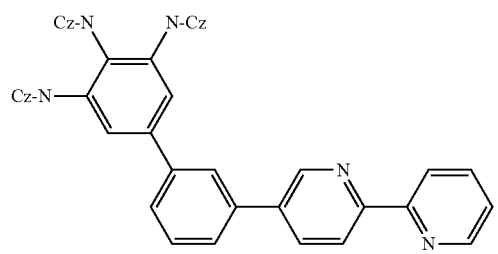
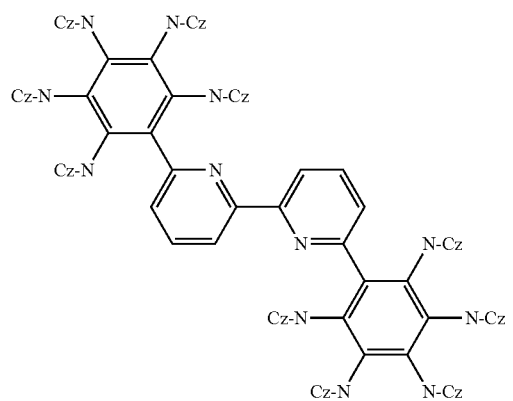

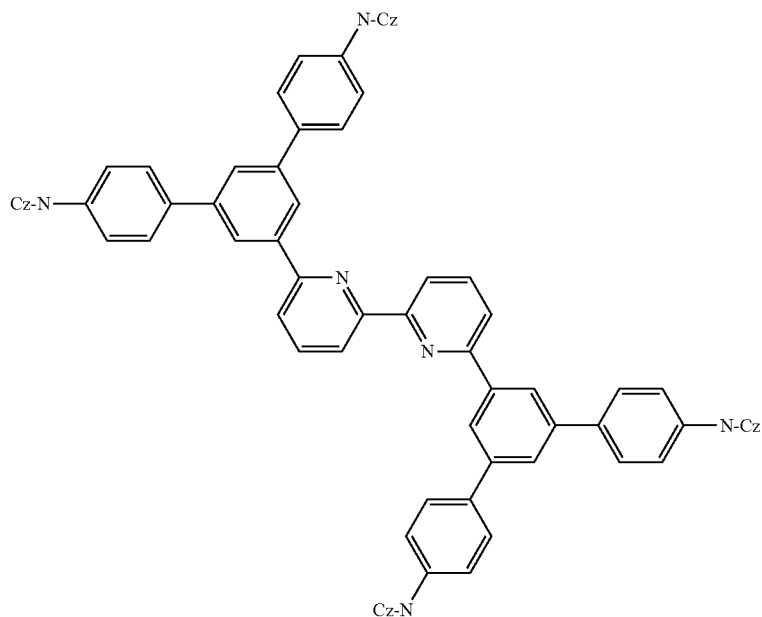
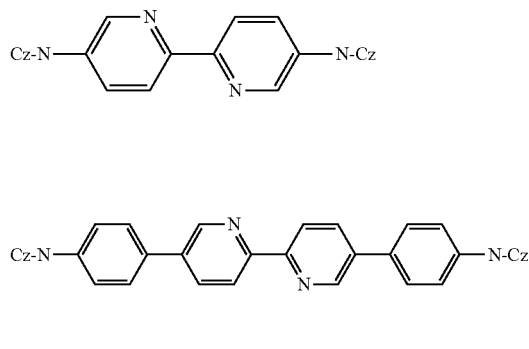
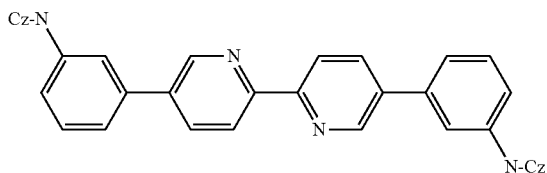
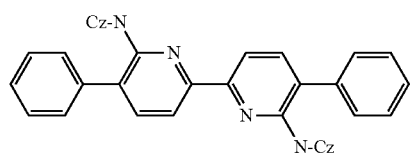
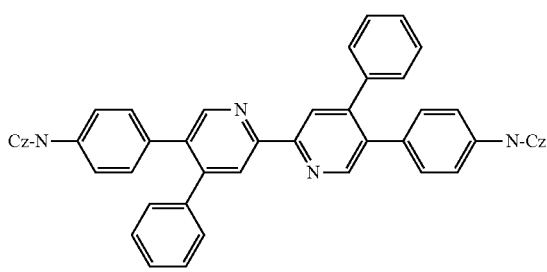
[Chemical Formula 22]
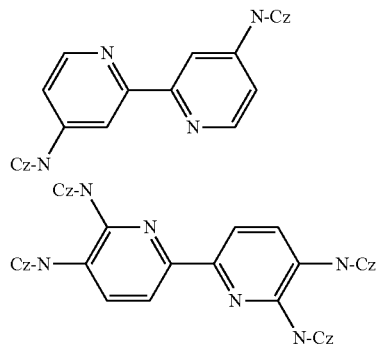
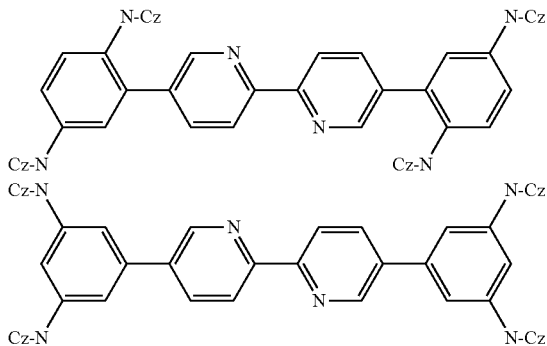

-continued
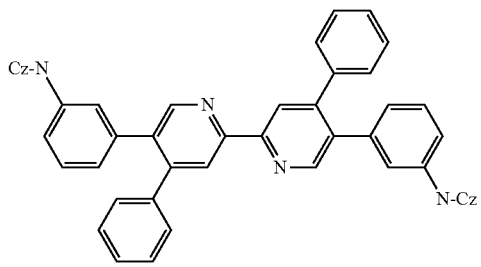
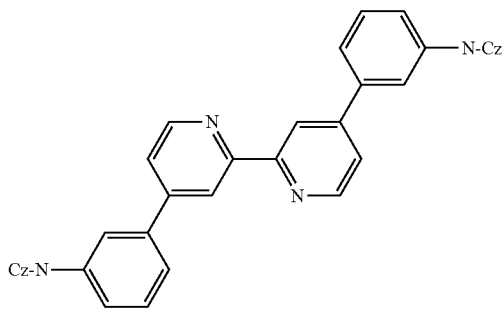
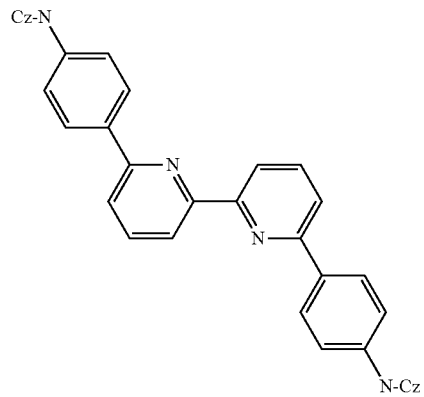
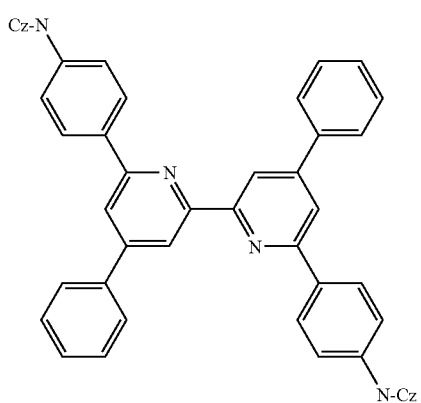
[Chemical Formula 23]
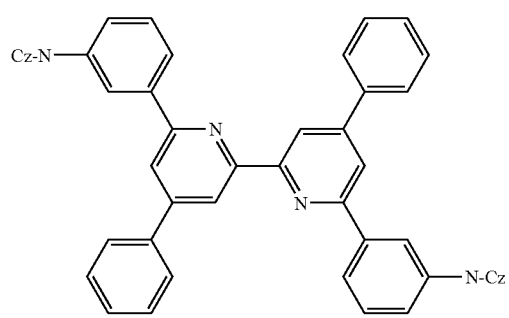
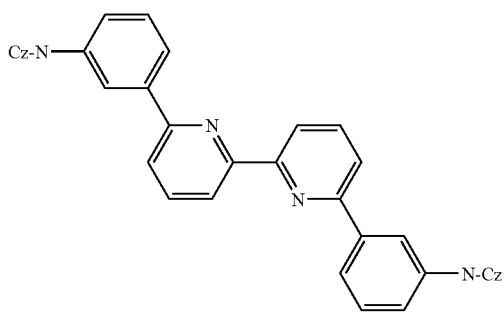
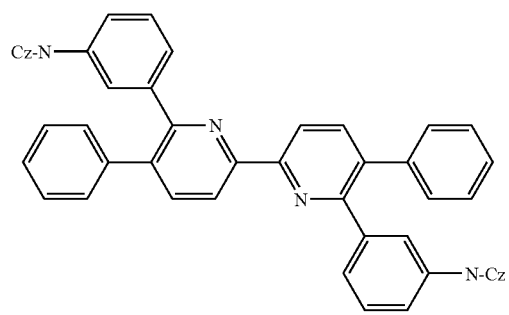
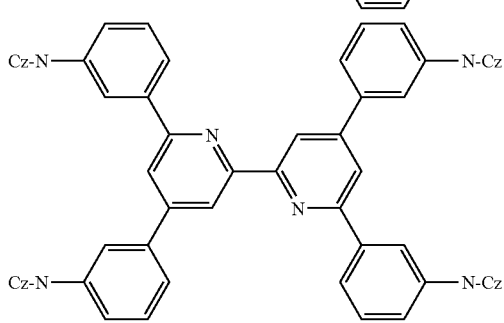
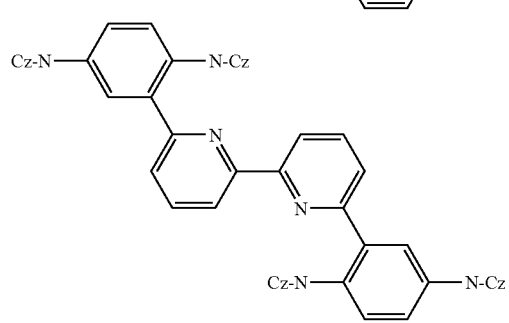

-continued
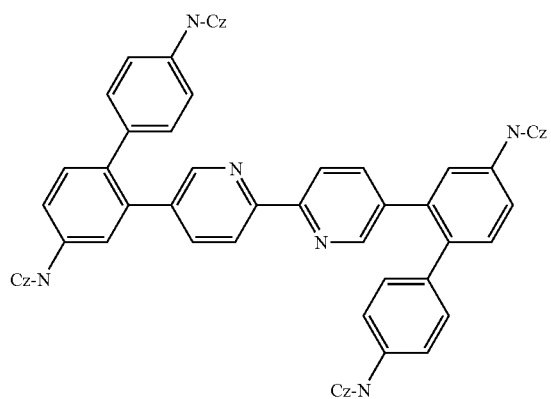
[Chemical Formula 24]
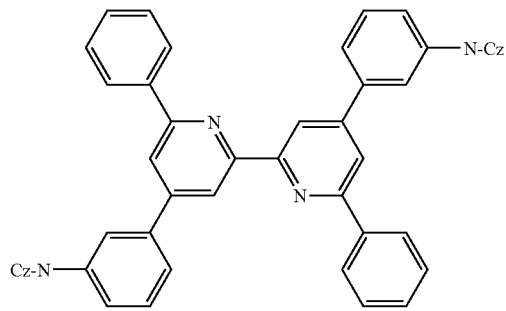
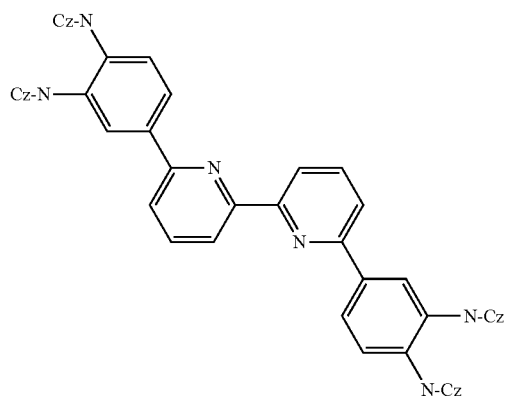
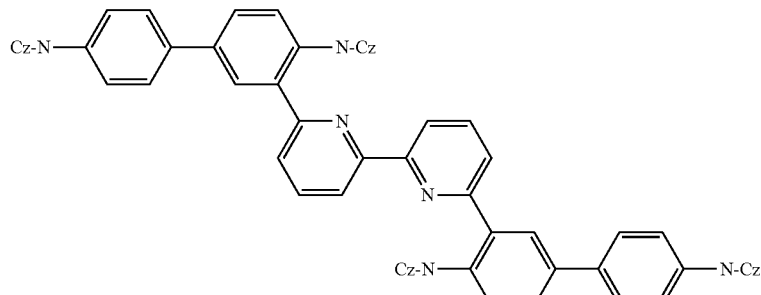
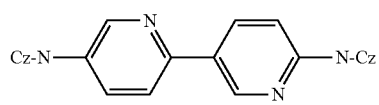
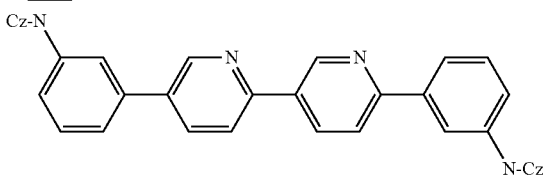

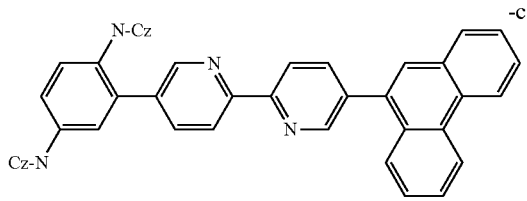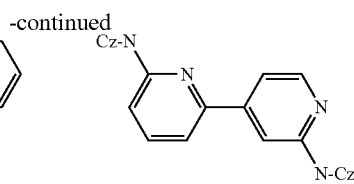

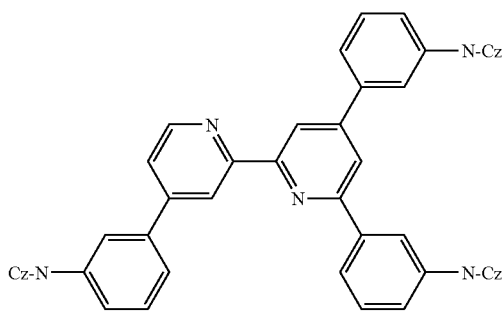
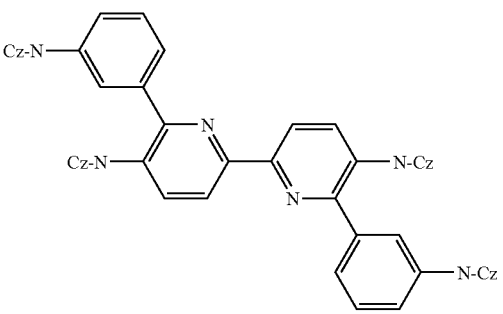
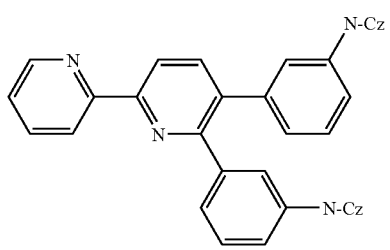
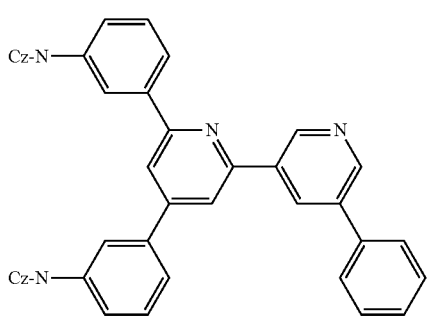
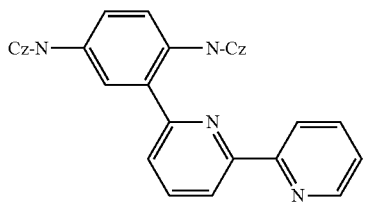
[Chemical Formula 26]
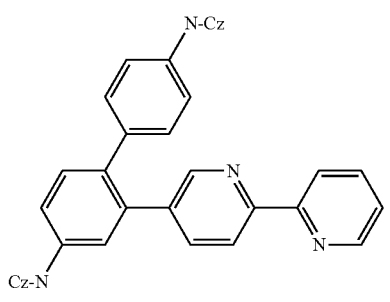
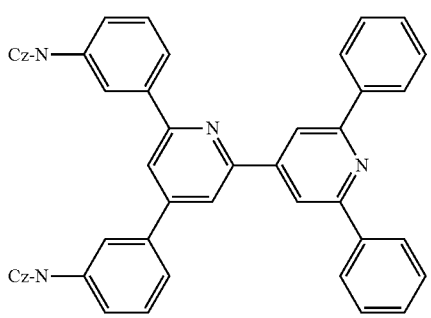
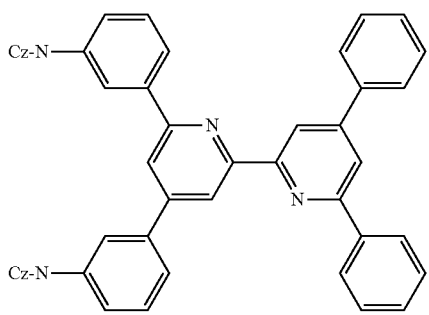
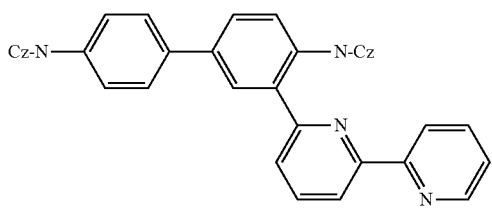

[Chemical Formula 27]

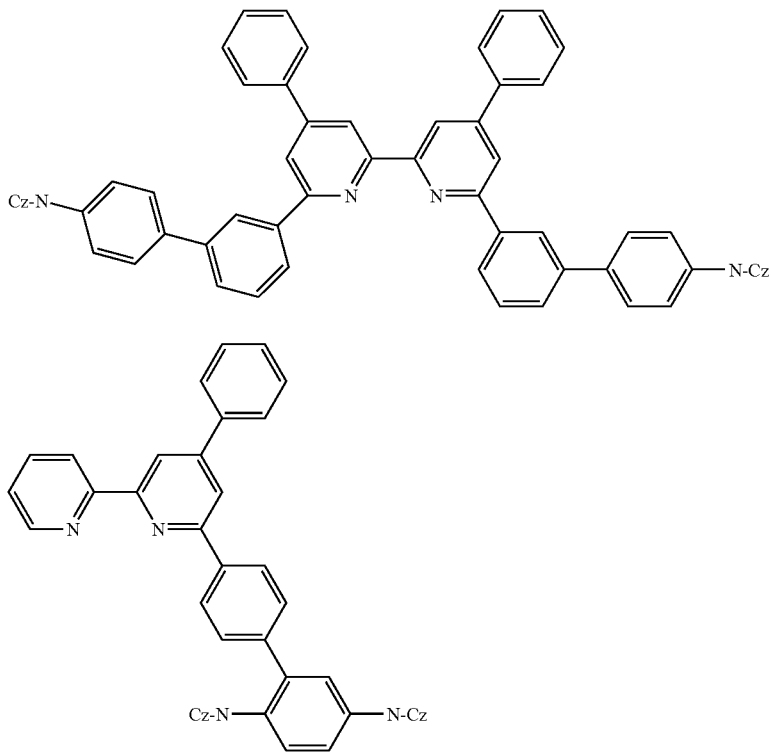

[6] PREPARATION METHOD

Each of organic compounds according to the present invention can be synthetically prepared according to a known procedure while selecting starting materials depending on the structure of a target compound.

(1) A bipyridyl skeleton, i.e., two pyridine rings directly bound to each other, can be introduced, for example, according to processes described in following A), B), C), D), and E):

A) A process as disclosed in Synthesis, 1-24; 1976 and cited references thereof. According to this process, synthesis is carried out by reacting an aldehyde and pyridyl acetylide in the presence of a strong acid such as sulfuric acid in a solvent, such as acetic acid, an alcohol, or an aromatic solvent including nitrobenzene, or a mixture of these, or reacting them with heating in the presence of a strong base, such as sodium hydroxide, in an alcohol and/or an aqueous solvent, to yield an intermediate (—CH=CR—CO—); and allowing an acylpyridinium salt and ammonium acetate to act upon the intermediate in a solvent such as acetic acid or methanol with heating in the presence of oxygen.

[Chemical Formula 28]

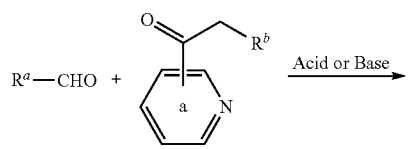

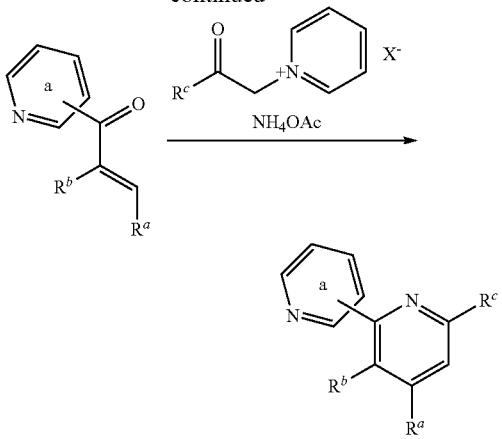

B) A process as disclosed typically in Synthesis, 1-24; 1976 and cited references thereof, Journal of the American Chemical Society, 126, 4958-4971; 2004, Inorganic Chemistry, 42, 2908-2918; 2003, and European Journal of Inorganic Chemistry, 1019-1029, 2001. According to this process, synthesis is carried out by reacting an aldehyde and an acetylide in the presence of a strong acid, such as sulfuric acid, in a solvent, such as acetic acid, an alcohol, nitrobenzene or another aromatic solvent, or a mixture of these solvents, or reacting them with heating in the presence of a strong base, such as sodium hydroxide, in an alcohol and/or an aqueous solvent to yield an intermediate (—CH=CR—CO—); and allowing a pyridacylpyridinium salt and ammonium acetate to act upon the intermediate with heating in a solvent, such as acetic acid or methanol, in the presence of oxygen.

[Chemical Formula 29]

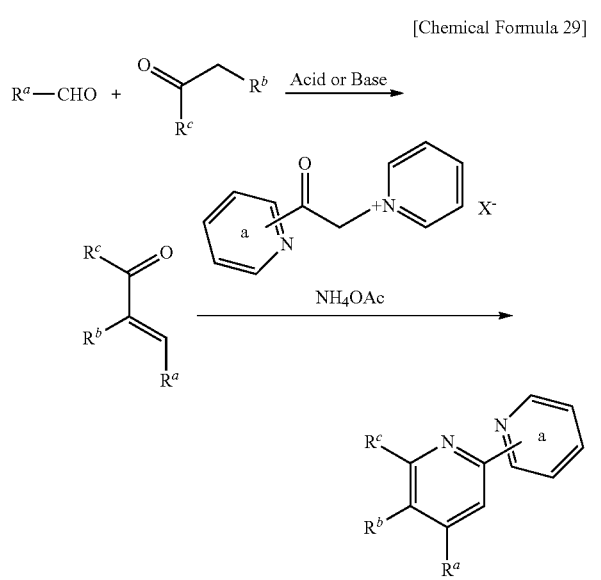

C) A process as disclosed typically in Synthesis, 1-24; 1976 and cited references thereof, Inorganic Chemistry, 42, 367-378; 2002, and Polyhedron, 22, 93-108; 2003. According to this process, synthesis is carried out by reacting an aldehyde and a 1,2-diketone in the presence of a strong acid, such as sulfuric acid, in a solvent, such as acetic acid, an alcohol, nitrobenzene or another aromatic solvent, or a mixture of these solvents, or reacting them with heating in the presence of a strong base, such as sodium hydroxide, in an alcohol and/or an aqueous solvent, to yield an intermediate (—CH=CR—CO—)$_2$; and allowing an acylpyridinium salt and ammonium acetate to act upon the intermediate with heating in a solvent, such as acetic acid or methanol, in the presence of oxygen.

[Chemical Formula 30]

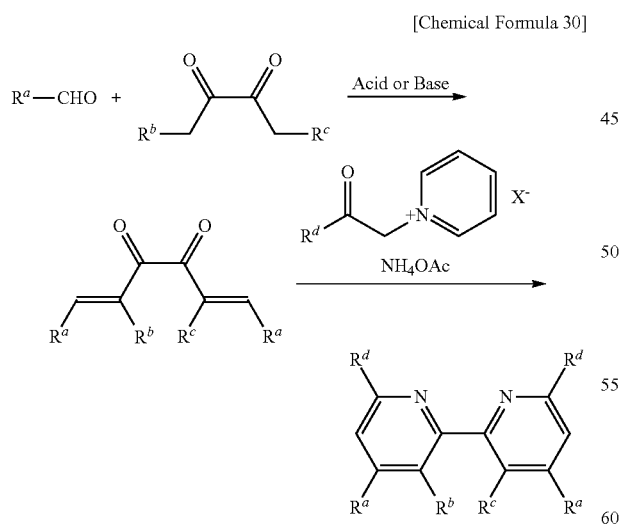

D) A process as disclosed typically in Journal of Organic Chemistry, 67, 443-449; 2002, and Inorganic Chemistry, 42, 367-378; 2002. According to this process, synthesis is carried out by reacting a halogenated pyridine typically with distannane or diborane by the catalysis of a transition metal catalyst, such as palladium or nickel, or reacting a halogenated pyridine with an organic lithium reagent, such as butyllithium, and subsequently reacting the same typically with chlorostannane or trialkoxyborane, to yield an organometallic reagent, such as an organic tin reagent, an organic boron reagent, or an organic zinc reagent; and reacting the organometallic reagent with a halogenated pyridine in the presence of a transition metal catalyst such as palladium or nickel.

[Chemical Formula 31]

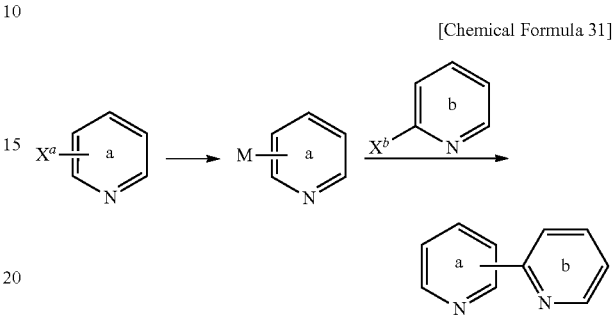

E) A process of dimerizing pyridine typically using Raney nickel, palladium carbon, butyllithium, or a boron trifluoride ether complex, as disclosed typically in Tetrahedron, 43, 895-904; 1987, Synthesis, 321-324; 1998, Organic Letters, 2, 803-805; 2000, and Journal of Organic Chemistry, 67, 443-449; 2002.

(2) Next, a carbazolyl group can be introduced, for example, by a process selected from the following processes depending on the bonding position thereof.

(2-1) An N-carbazolyl group can be introduced, for example, any of following processes a), b), and c).

a) A process of reacting an aromatic di- or higher-substituted fluoride (F—Ar—F) having a bipyridyl skeleton, a substituted or unsubstituted carbazole, and a strong base to yield a reaction mixture, and stirring the reaction mixture with heating under reflux for one to sixty hours in a solvent. The strong base includes, for example, sodium hydride, tert-butoxypotassium, and n-butyllithium. The amount of the strong base is about 1.1 to 10 equivalents relative to fluorine atom. The solvent includes tetrahydrofuran, dioxane, an ether, and N,N-dimethylformamide.

[Chemical Formula 32]

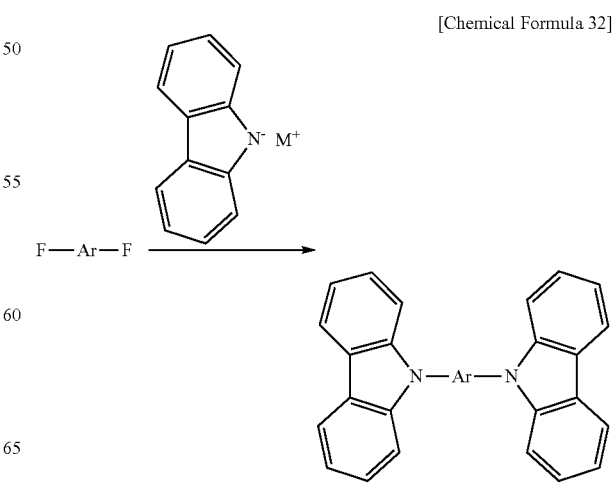

-continued

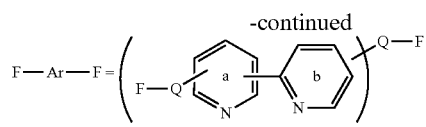

b) A process of stirring and mixing an aromatic di- or higher-substituted halide (X—Ar—X, wherein X is preferably Br or I) having a bipyridyl skeleton and a substituted or unsubstituted carbazole by the catalysis of a copper catalyst in the presence of a basic substance in the absence of or in the presence of a solvent at temperatures from 20° C. to 300° C. in an inert gas stream for one to sixty hours. The copper catalyst includes, for example, copper powder, copper wire, a halogenated copper (CuX, wherein X is Cl, Br, or I)), and copper oxide (CuO). The amount of the copper catalyst is about 0.1 to 5 equivalents relative to the halogen atom. The basic substance includes, for example, potassium carbonate, calcium carbonate, potassium phosphate, cesium carbonate, and tert-butoxysodium. The amount of the basic substance is about 1 to 10 equivalents relative to the halogen atom. The solvent includes, for example, aromatic solvents such as nitrobenzene; as well as other solvents such as Tetraglyme and polyethylene glycols.

[Chemical Formula 33]

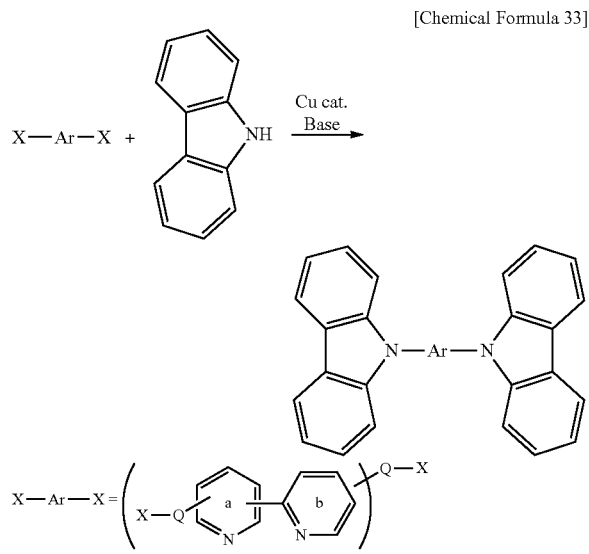

c) A process of stirring an aromatic di- or tri-substituted halide (X—Ar—X, wherein X is preferably Cl, Br, or I) having a bipyridyl skeleton with a substituted or unsubstituted carbazole in the presence of a catalyst and a basic substance in a solvent at temperatures of from 30° C. to 200° C. over one to sixty hours. Examples of the catalyst include a combination of bivalent palladium catalyst with a ligand; a zerovalent palladium complex; and a palladium chloride complex. The bivalent palladium catalyst includes, for example, $Pd_2(dba)_3$, wherein Pd represents palladium; and dba represents dibenzylideneacetone, $Pd(dba)_2$, and palladium acetate. The ligand includes, for example, BINAP (i.e., 2,2'-bis(diphenylphosphino-1,1'-binaphthyl), tri(tert-butyl)phosphine, triphenylphosphine, 1,2-bis(diphenylphosphino)ethane, 1,3-bis(diphenylphosphino)propane, 1,3-bis(diphenylphosphino)butane, and dppf (i.e., 1,1'-bis(diphenylphosphino)ferrocene). The zerovalent palladium complex includes, for example, $Pd(PPh_3)_4$ wherein $PPh_3$ represents triphenylphosphine. The palladium chloride complex includes, for example, $PdCl_2(dppf)_2$. The amount of the catalyst is about 0.001 to 1 equivalent relative to the halogen atom. Examples of the basic substance include tert-butoxypotassium, tert-butoxysodium, potassium carbonate, cesium carbonate, and triethylamine. The amount of the basic substance is generally 1.1 to 10 equivalents relative to the halogen atom. Examples of the solvent include tetrahydrofuran, dioxane, dimethoxyethane, N,N-dimethylformamide, dimethyl sulfoxide, xylenes, toluene, and triethylamine.

[Chemical Formula 34]

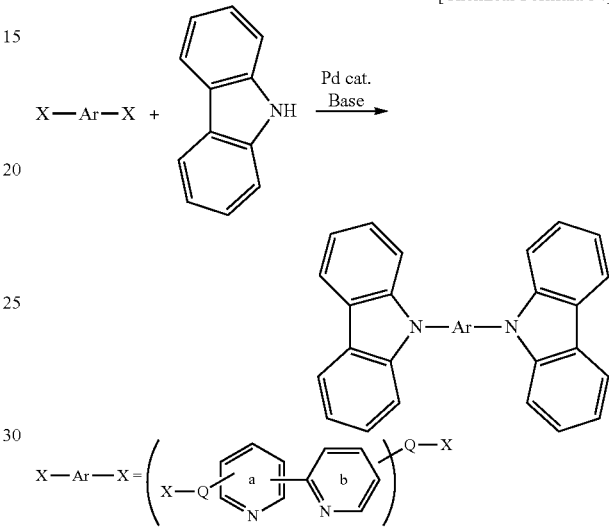

(2-2) The introduction of a 2-, 3-, 4-, 5-, 6-, 7- or 8-carbazolyl group can be carried out, for example, by using a coupling reaction between an aryl borate and a carbazole having a halogen atom, such as chlorine, bromine, or iodine, at the position to which the linkage group Q is to be bound, or a coupling reaction between a halogenated aryl and a carbazolyl borate. More specifically, any known coupling procedures can be used herein. Such coupling procedures are bonding reactions (coupling reactions) between rings, as described or cited typically in "Palladium in Heterocyclic Chemistry: A guide for the Synthetic Chemist" (Second Ed., 2002, Jie Jack Li and Gordon W. Gribble, Pergamon Press), Sen-ikinzoku Ga Hiraku Yukigousei-Sono Tasai Na Hannokeishiki To Saishin No Seika (in Japanese; Organic Syntheses Developed by Transition Metals, Their Various Reaction Modes and Latest Products)" (1997, Jiro Tsuji, Kagaku-Dojin Publishing Company, Inc.), and "Vollhardt & Schore, Organic Chemistry, Last Volume" (2004, K. P. C. Vollhardt, Kagaku-Dojin Publishing Company, Inc.).

(3) In addition to the above-exemplified preparation procedures or processes, where necessary, any known coupling procedures can be applied in the present invention to the formation of linkage groups (namely, $Q^1$ and $Q^2$) connecting a carbazolyl group and a bipyridyl skeleton. Such coupling procedures are bonding reactions (coupling reactions) between rings, as described or cited typically in "Palladium in Heterocyclic Chemistry: A guide for the Synthetic Chemist" (Second Ed., 2002, Jie Jack Li and Gordon W. Gribble, Pergamon Press), Sen-ikinzoku Ga Hiraku Yukigousei-Sono Tasai Na Hannokeishiki To Saishin No Seika (in Japanese, Organic Syntheses Developed by Transition Metals, Their Various Reaction Modes and Latest Products)" (1997, Jiro Tsuji, Kagaku-Dojin Publishing Company, Inc.), and "Vollhardt & Schore, Organic Chemistry, Last Volume" (2004, K. P. C. Vollhardt, Kagaku-Dojin Publishing Company, Inc.).

(4) The purification of a compound can be carried out, for example, by using known techniques such as techniques described in "Handbook of Separation/Purification Technology" (1993, edited by the Chemical Society of Japan), "High-purity Separation of Trace Components and Difficult-to-Separate Substances by Chemical Conversion" (1988, published by IPC Co., Ltd.), and "Experimental Chemistry (Fourth Ed.) Vol. 1; Section: Separation and Purification" (1990, edited by the Chemical Society of Japan). Specific examples of purification procedures include extraction (including washing in a suspended state, boiling washing, ultrasonic washing, and washing with an acid and/or a base), adsorption, occlusion, melting or fusion, crystallization (including recrystallization from a solvent, and reprecipitation), distillation (distillation under normal pressure and distillation under reduced pressure), evaporation, sublimation (sublimation under normal pressure and sublimation under reduced pressure), ion exchange, dialysis, filtration, ultrafiltration, reverse osmosis, pressurized osmosis, zone melting, electrophoresis, centrifugation, floatation separation, sedimentation, magnetic separation, and various chromatography techniques. Such chromatography techniques are classified by the shape into column, paper, thin-layer, and capillary chromatography; by the mobile phase into gas, liquid, micelle, and supercritical fluid chromatography; and by the separation mechanism into adsorption, partition, ion-exchange, molecular sieve, chelate, gel filtration, exclusion, and affinity chromatography.

(5) The identification of a product and the analysis of a purity thereof can be carried out by applying a procedure or an apparatus according to necessity. Such procedures and apparatuses for use herein include a gas chromatograph (GC), a high-performance liquid chromatograph (HPLC), a high-performance amino acid analyzer (AAA), capillary electrophoresis measurement (CE), a size exclusion chromatograph (SEC), a gel permeation chromatograph (GPC), a cross fractionation chromatograph (CFC), mass spectrometry (MS, LC/MS, GC/MS, and MS/MS), a nuclear magnetic resonance apparatus (NMR ($^1$H-NMR or $^{13}$C-NMR)), a Fourier transform infrared spectrophotometer (FT-IR), an ultraviolet-visible ray-near infrared spectrophotometer (UV.VIS, NIR), an electron spin resonance spectrometer (ESR), a transmission electron microscope (TEM-EDX), an electron probe microanalyzer (EPMA), metal element analysis (an ion chromatograph, inductively-coupled plasma atomic emission spectrometry (ICP-AES), atomic absorption spectrophotometry (AAS), and an X-ray fluorescence spectrometer (XRF)), nonmetal element analysis, and trace analysis (inductively coupled plasma mass spectrometry (ICP-MS), graphite furnace atomic absorption spectrometry (GF-AAS), and glow discharge mass spectrometry (GD-MS)).

[Charge Transporting Material]

An organic compound according to the present invention has excellent charge transporting ability and is useful as a charge transporting material. A charge transporting material containing such an organic compound according to the present invention has excellent filming properties charge transporting ability, light-emitting properties, and thermal stability.

[Organic Electroluminescent Device]

Next, an organic electroluminescent device according to the present invention using the organic compound according to the present invention will be illustrated below.

An organic electroluminescent device according to the present invention is an organic electroluminescent device including a substrate bearing an anode, a cathode, and an organic light-emitting layer arranged between the two electrodes, in which the organic electroluminescent device includes a layer containing the organic compound between the anode and the cathode. The device preferably includes the organic compound according to the present invention in the organic light-emitting layer. The device particularly preferably contains the organic compound according to the present invention as a host material in the organic light-emitting layer, which host material is doped with an organometallic complex.

When used as a host material of an organic light-emitting layer of an organic electroluminescent device as above, each of organic compounds according to the present invention can be used alone or in combination.

Hereinafter, structures of organic electroluminescent devices according to the present invention will be illustrated by way of example, with reference to the attached drawings. It should be noted, however, the exemplified structures of organic electroluminescent devices according to the present invention are not limitative.

FIGS. 1 to 3 are cross-sectional views schematically illustrating structures of organic electroluminescent devices according to the present invention by way of example. FIGS. 1 to 3 illustrate a substrate 1, an anode 2, a hole injection layer (anode buffer layer) 3, a hole transport layer 4, an organic light-emitting layer (hereinafter also referred to as "light-emitting layer") 5, a hole blocking layer 6, an electron transport layer 7, and a cathode 8.

Substrate

The substrate 1 functions as a support in the organic electroluminescent device, and may include a plate of quartz or glass, a metal plate or metal foil, or a plastic film or sheet. In particular, a glass plate and a plate or film of transparent synthetic resin such as a polyester, a polymethacrylate, a polycarbonate or a polysulfone are preferred. When a synthetic resin substrate is used, its gas barrier properties are important. If the gas barrier properties are too poor, the organic electroluminescent device might deteriorate due to the air outside having passed through the substrate, thus poor gas barrier properties not being preferred. To avoid this, for example, a dense silicon oxide film may be preferably arranged on at least one side of the synthetic resin substrate to thereby ensure sufficient gas barrier properties.

Anode

An anode 2 is arranged on the substrate 1. The anode 2 serves to inject holes into a hole transport layer 4. The anode 2 generally includes a metal such as aluminum, gold, silver, nickel, palladium or platinum, a metal oxide such as indium oxide and/or tin oxide, a metal halide such as copper iodide, carbon black, or a conductive polymer such as a poly(3-methylthiophene), a polypyrrole, or a polyaniline. The anode 2 is generally formed by sputtering or vacuum deposition. When the anode 2 is formed from fine particles of a metal such as silver, fine particles of copper iodide, carbon black, fine particles of a conductive metal oxide, or fine particles of a conductive polymer, it can also be formed by dispersing such particles in a suitable binder resin solution and coating the dispersion on the substrate 1. Further, when the anode 2 is formed from an electroconductive polymer, the anode 2 can also be directly formed as a polymerized thin film on the substrate 1 through electrolytic polymerization or formed by applying an electroconductive polymer to the substrate 1 (App. Phys. Lett., vol. 60, p. 2711, 1992).

The anode 2 is usually of a single-layer structure but, as needed, it may be of a multilayer structure made from two or more different materials.

The thickness of the anode 2 varies depending upon required transparency. When some transparency is required, the transmittance for visible light is adjusted to be usually 60% or more, and preferably 80% or more. In this case, the thickness of the anode is usually 5 nm or more, and preferably 10 nm or more, and is usually 1,000 nm or less, and preferably 500 nm or less. When the anode may be opaque, the thickness of the anode 2 is arbitrary, and may be formed by a metal according to necessity, so as to also function as the substrate 1.

Hole Transport Layer

The device of the structure shown in FIG. 1 includes a hole transport layer 4 arranged on the anode 2. A material for the hole transport layer is required to show a high hole injecting efficiency from the anode and transport the injected holes with high efficiency. For satisfying the requirements, the material is required to have a small ionization potential, show a high transparency for a visible light, show a high hole mobility, have an excellent stability and resistance to the formation of impurities, which function as a trap, upon production or upon use. Since the hole transport layer is in contact with the light-emitting layer 5, the material is required not to reduce the luminous efficiency by quenching the light emitted from the light-emitting layer 5 or by forming an exciplex with the light-emitting layer 5. In addition to the above-described general requirements, the device is required to have some heat resistance in consideration of application to an onboard display. Therefore, a material having a glass transition temperature of 85° C. or higher is desirable.

Examples of such hole transporting materials include, as with hole transporting materials for use as a host material of the light-emitting layer 5, aromatic diamines containing two or more tertiary amines wherein the nitrogen atoms are substituted by two or more condensed aromatic rings, typified by 4,4'-bis[N-(1-naphthyl)-N-phenylamino]biphenyl (Japanese Unexamined Patent Application Publication No. 5-234681); aromatic amine compounds having a star-burst structure such as 4,4',4''-tris(1-naphthylphenylamino)triphenylamine (J. Lumin., vol. 72-74, p. 985, 1997); aromatic amine compounds including a tetramer of triphenylamine (Chem. Commun., p. 2175, 1996); spiro compounds such as 2,2',7,7'-tetrakis-(diphenylamino)-9,9'-spirobifluorene (Synth. Metals, vol. 91, p. 209, 1997); and carbazole derivatives such as 4,4'-N,N'-dicarbazolebiphenyl. Each of these compounds can be used alone or in combination according to necessity.

In addition to the above-mentioned compounds, materials for the hole transport layer 4 further include polymer materials such as polyvinylcarbazoles, polyvinyltriphenylamines (Japanese Unexamined Patent Application Publication No. 7-53953), and poly(arylene ether sulfone)s containing tetraphenylbenzidine (Polym. Adv. Tech., vol. 7, p. 33, 1996).

The hole transport layer 4 can be formed by a wet filming process or a dry filming process. Such wet filming processes include common coating processes such as spraying, printing, spin coating, dip coating, and die coating; and printing processes such as an ink jet process and screen printing. Such dry filming processes include a vacuum deposition process.

When the hole transport layer 4 is formed by a coating process, one or more different hole transporting materials and, as needed, a binder resin and/or an additive such as a coating property-improving agent which does not function as a trap of holes are dissolved in a proper solvent to prepare a coating solution, and the solution is applied to the anode 2 according typically to spin coating, followed by drying to form the hole transport layer 4. Examples of the binder resin include polycarbonates, polyarylates, and polyesters. When added in a large amount, the binder resin would reduce the hole mobility, and hence the amount is preferably small. Accordingly, the content in the hole transport layer is generally preferably 50 percent by weight or less.

When the hole transport layer is formed by vacuum deposition, a hole transporting material is placed in a crucible installed within a vacuum chamber and, after evacuating the vacuum chamber using a suitable vacuum pump to a degree of vacuum of about $10^{-4}$ Pa, the crucible is heated to evaporate the hole transporting material and form the hole transport layer 4 on the substrate 1 bearing the anode 2 which is placed facing the crucible.

The thickness of the hole transport layer 4 is usually 5 nm or more, and preferably 10 nm or more, and is usually 300 nm or less, and preferably 100 nm or less. In order to uniformly form such a thin film, vacuum deposition is generally often employed.

Organic Light-Emitting Layer

In the device shown in FIG. 1, a light-emitting layer 5 is arranged on the hole transport layer 4. The light-emitting layer 5 is formed by a light-emitting compound which can emit a strong light when strongly excited in a space between energized electrodes. The excitation is caused by recombination of holes injected from the anode and having migrated through the hole transport layer with electrons injected from the cathode and having migrated through the hole blocking layer 6. The light-emitting layer 5 generally contains a dopant material acting as a light-emitting substance, and a host material. Materials contained in a light-emitting layer, such as a dopant material and a host material, are herein referred to as light-emitting layer materials.

Such a light-emitting layer material to be used in the light-emitting layer 5 is required to be a compound which shows a stable thin film form, shows a high quantum yield in emission of light (fluorescence or phosphorescence) in a solid state and can transport holes and/or electrons with a high efficiency. Further, the compound is required to be electrochemically and chemically stable and resistant to the formation of impurities, functioning as a trap, upon production or use thereof.

Light-emitting materials for use in the present invention are preferably light-emitting materials having a first oxidation potential smaller than the first oxidation potential of a hole blocking material, in which the first oxidation potentials are determined in cyclic voltammetry, as described in the after-mentioned hole blocking layer. Of such light-emitting materials, more preferred as light-emitting layer materials are light-emitting materials satisfying the following conditions:

(Oxidation potential of the hole blocking material)−
(Oxidation potential of the light-emitting layer material)≧0.1 V (Reduction potential of the hole blocking material)≧
(Reduction potential of the light-emitting material)

When the light-emitting layer 5 contains a host material and a dopant material, the oxidation or reduction potential of the light-emitting layer material in the above formulae refers to the oxidation or reduction potential of the host material.

Such materials which satisfy the requirements and can form organic light-emitting layers capable of emitting fluorescence include metal complexes such as 8-hydroxyquinoline aluminum complex (Japanese Unexamined Patent Application Publication No. 59-194393), metal complexes of 10-hydroxybenzo[h]quinoline (Japanese Unexamined Patent Application Publication No. 6-322362), bisstyrylbenzene derivatives (Japanese Unexamined Patent Application Publications No. 1-245087 and No. 2-222484), bisstyrylarylene derivatives (Japanese Unexamined Patent Application Publication No. 2-247278), metal complexes of (2-hydroxyphenyl)benzothiazole (Japanese Unexamined Patent Application Publication No. 8-315983), and silole derivatives. These materials for the light-emitting layer are deposited on the hole transport layer usually by vacuum deposition. Of the above-mentioned hole transporting materials, aromatic amine compounds capable of emitting a light can also be used as the light-emitting layer materials.

For the purpose of improving luminous efficiency of the device and changing the color of emitted light, it has been conducted, for example, to dope a host material of 8-hydroxyquinoline aluminum complex with a fluorescent dye for laser such as coumarin (J. Appl. Phys., vol. 65, p. 3610, 1989). This doping technique can also be applied to the light-emitting layer 5 and, as the material for doping, various fluorescent dyes in addition to coumarin may be used as well. Examples of fluorescent dyes giving a blue light emission include perylene, pyrene, anthracene, coumarin, and derivatives of these. Examples of fluorescent dyes giving a green light emission include quinacridone derivatives and coumarin derivatives. Examples of fluorescent dyes giving a yellow light emission include rubrene and perimidone derivatives. Examples of fluorescent dyes giving a red light emission include DCM (4-dicyanomethylene-2-methyl-6-p-dimethylaminostyryl-4H-pyran) derivatives, benzopyran derivatives, rhodamine derivatives, benzothioxanthene derivatives, and azabenzothioxanthene.

In addition to the above-described fluorescent dyes for doping, fluorescent dyes illustrated in Laser Kenkyu (in Japanese; Laser Research), vol. 8, p. 694, p. 803, p. 958 (1980) and ibid., vol. 9, p. 85 (1981) may be selected according to the kind of the host material and used as a doping material for the light-emitting layer.

The doping amount of the fluorescent dye relative to the host material is preferably $10^{-3}$ percent by weight or more, and more preferably 0.1 percent by weight or more, and is preferably 10 percent by weight or less, and more preferably 3 percent by weight or less. If the amount is less than the lower limit, the dopant might fail to contribute to improvement of luminous efficiency of the device whereas, if the amount exceeds the upper limit, there might result quenching of light, possibly leading to reduction in the luminous efficiency.

In this connection, an organic compound according to the present invention is suitable as a host material for an organic light-emitting layer of an organic electroluminescent device. This is because the organic compound has both a moiety mainly bearing a hole transporting activity and another moiety mainly bearing an electron transporting activity, thereby shows both excellent hole transporting ability and excellent electron transporting ability, and has excellent durability against electric oxidation/reduction and a high triplet excitation level, as described above. Thus, the organic light-emitting layer of an organic electroluminescent device according to the present invention preferably includes the organic compound according to the present invention as a host material, which host material is doped with an organometallic complex suitable as a light-emitting substance for the after-mentioned reasons.

Preferred dopant materials for use in a light-emitting layer in the present invention include organic metal complexes containing metals selected from metals belonging to Group 7 to Group 11 of the periodic table. These metal complexes preferably have a TI (excited triplet level) lower than T1 of the organic compound according to the present invention used as a host material, from the viewpoint of luminous efficiency. In addition, such a dopant material is required to have chemical stability typically against oxidation and reduction, because the dopant material serves to emit a light.

Preferred examples of the metal in the phosphorescent organometallic complex containing a metal selected from among metals belonging to Group 7 to Group 11 of the periodic table include ruthenium, rhodium, palladium, silver, rhenium, osmium, iridium, platinum, and gold. Preferred examples as these organometallic complexes include compounds represented by following Formula (V) or (VI):

$$MLk-jL'j \qquad (V)$$

wherein M represents a metal; "k" represents the valency of the metal; L and L' each represent a bidentate ligand; and "j" represents 0 or 1 or 2:

[Chemical Formula 35]

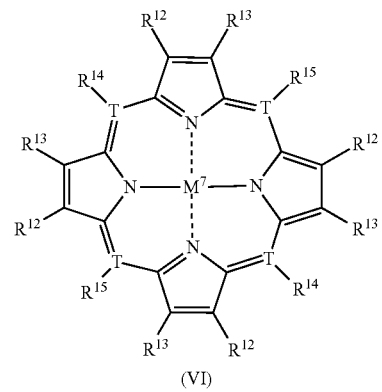

(VI)

wherein $M^7$ represents a metal; T represents carbon or nitrogen; and, when T represents nitrogen, $R^{14}$ and $R^{15}$ are absent and, when T represents carbon, $R^{14}$ and $R^{15}$ each represent a hydrogen atom, a halogen atom, an alkyl group, an aralkyl group, an alkenyl group, a cyano group, an amino group, an acyl group, an alkoxycarbonyl group, a carboxyl group, an alkoxy group, an alkylamino group, an aralkylamino group, a haloalkyl group, a hydroxyl group, an aryloxy group, an aromatic hydrocarbon group which may be substituted, or aromatic heterocyclic group which may be substituted;

$R^{12}$ and $R^{13}$ each represent a hydrogen atom, a halogen atom, an alkyl group, an aralkyl group, an alkenyl group, a cyano group, an amino group, an acyl group, an alkoxycarbonyl group, a carboxyl group, an alkoxy group, an alkylamino group, an aralkylamino group, a haloalkyl group, a hydroxyl group, an aryloxy group, an aromatic hydrocarbon group which may be substituted, or aromatic heterocyclic group which may be substituted, and $R^{12}$ and $R^{13}$ may be combined with each other to form a ring.

The bidentate ligands L and L' in Formula (V) each represent a ligand having the following partial structure:

L:

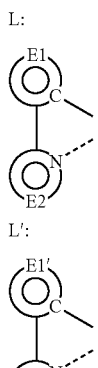

L':

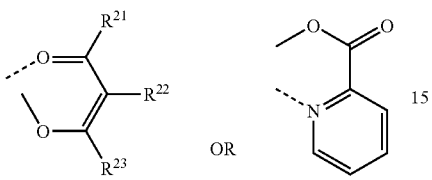

wherein Ring E1 and Ring E1' each independently represent an aromatic hydrocarbon group which may be substituted or an aromatic heterocyclic group which may be substituted; Ring E2 and Ring E2' each represent a nitrogen-containing aromatic heterocyclic group which may be substituted; and $R^{21}$, $R^{22}$ and $R^{23}$ each represent a halogen atom, an alkyl group, an alkenyl group, an alkoxycarbonyl group, a methoxy group, an alkoxy group, an aryloxy group, a dialkylamino group, a diarylamino group, a carbazolyl group, an acyl group, a haloalkyl group, or a cyano group.

More preferred examples of compounds represented by Formula (V) include compounds represented by following Formulae (Va), (Vb), and (Vc):

[Chemical Formula 37]

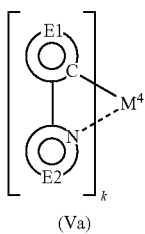

(Va)

wherein $M^4$ represents a metal; "k" represents the valency of the metal; Ring E1 represents an aromatic hydrocarbon group which may be substituted; and Ring E2 represents a nitrogen-containing aromatic heterocyclic group which may be substituted:

[Chemical Formula 38]

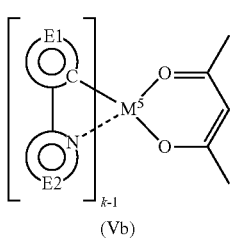

(Vb)

wherein $M^5$ represents a metal; "k" represents the valency of the metal; Ring E1 represents an aromatic hydrocarbon group which may be substituted or an aromatic heterocyclic group which may be substituted; and Ring E2 represents a nitrogen-containing aromatic heterocyclic group which may be substituted:

[Chemical Formula 39]

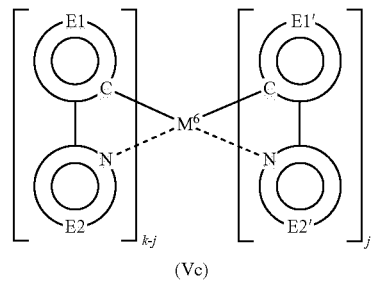

(Vc)

wherein $M^6$ represents a metal; "k" represents the valency of the metal; "j" represents 0 or 1 or 2; each of Ring E1 and Ring E1' independently represents an aromatic hydrocarbon group which may be substituted or an aromatic heterocyclic group which may be substituted; and each of Ring E2 and Ring E2' independently represents a nitrogen-containing aromatic heterocyclic group which may be substituted.

Preferred as Ring E1 and Ring E1' of the compounds represented by Formulae (Va), (Vb), and (Vc) are phenyl group, biphenyl group, naphthyl group, anthryl group, thienyl group, furyl group, benzothienyl group, benzofuryl group, pyridyl group, quinolyl group, isoquinolyl group, and carbazolyl group.

Preferred as Ring E2 and Ring E2' are pyridyl group, pyrimidyl group, pyrazyl group, triazyl group, benzothiazole group, benzoxazole group, benzimidazole group, quinolyl group, isoquinolyl group, quinoxalyl group, and phenanthrydyl group.

Examples of substituents which the compounds represented by Formulae (Va), (Vb) and (Vc) may have include halogen atoms such as fluorine atom; alkyl groups having one to six carbon atoms, such as methyl group and ethyl group; alkenyl groups having two to six carbon atoms, such as vinyl group; alkoxycarbonyl groups having two to six carbon atoms, such as methoxycarbonyl group and ethoxycarbonyl group; alkoxy groups having one to six carbon atoms, such as methoxy group and ethoxy group; aryloxy groups such as phenoxy group and benzyloxy group; dialkylamino groups such as dimethylamino group and diethylamino group; diarylamino groups such as diphenylamino group; carbazolyl groups; acyl groups such as acetyl group; haloalkyl groups such as trifluoromethyl group; and cyano group. These substituents may be combined with each other to form a ring.

Additionally, a substituent of Ring E1 and a substituent of Ring E2 may be combined with each other to form one condensed ring, or a substituent of Ring E1' and a substituent of Ring E2' may be combined with each other to form one condensed ring. An example of such a condensed ring is 7,8-benzoquinoline group.

More preferred examples of substituents in Ring E1, Ring E1', Ring E2 and Ring E2' include alkyl groups, alkoxy groups, aromatic hydrocarbon groups, cyano groups, halogen atoms, haloalkyl groups, diarylamino groups, and carbazolyl groups.

Preferred Examples of $M^4$ and $M^5$ in Formulae (Va) and (Vb) include ruthenium, rhodium, palladium, silver, rhenium, osmium, iridium, platinum, and gold. Preferred examples of $M^7$ in Formula (VI) include ruthenium, rhodium, palladium, silver, rhenium, osmium; iridium, platinum, and gold, of which bivalent metals such as platinum and palladium are more preferred.
Specific examples of the organometallic complexes represented by Formulae (V), (Va), (Vb), and (Vc) are illustrated below, which, however, not limitative at all.
[Chemical Formula 40]
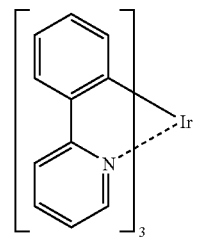
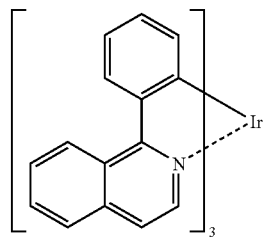
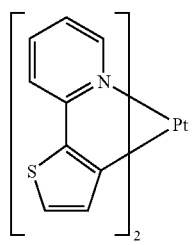
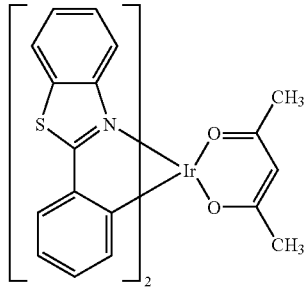
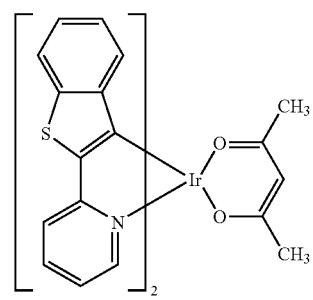
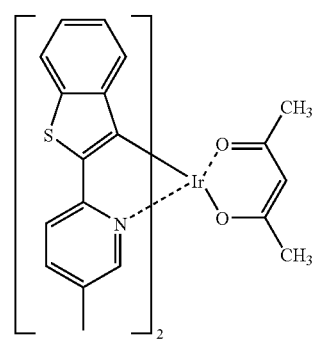
-continued
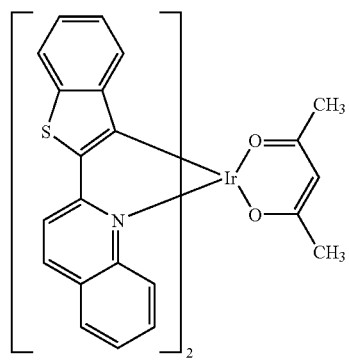
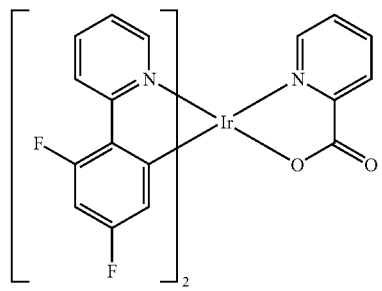
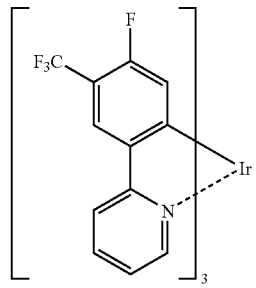
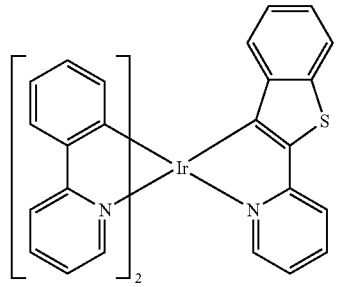
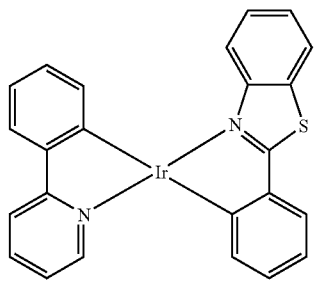

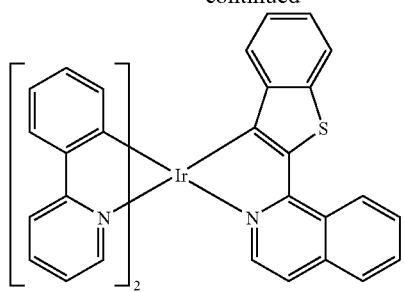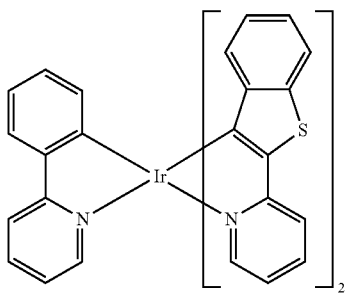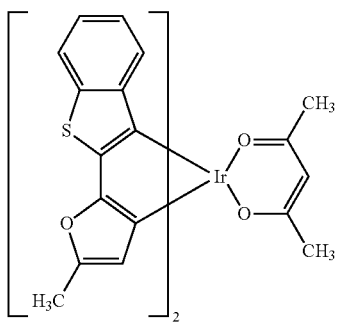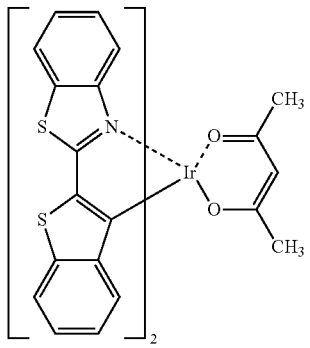
[Chemical Formula 41]
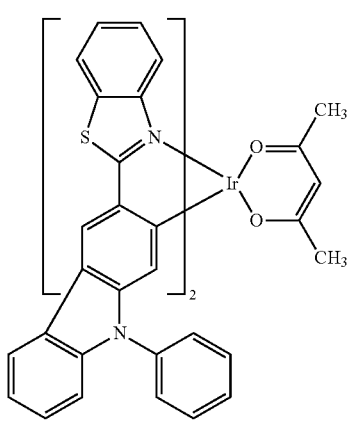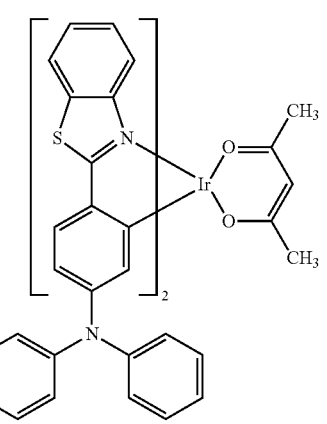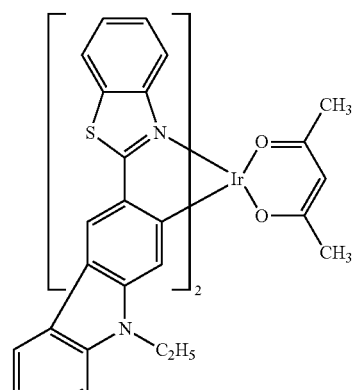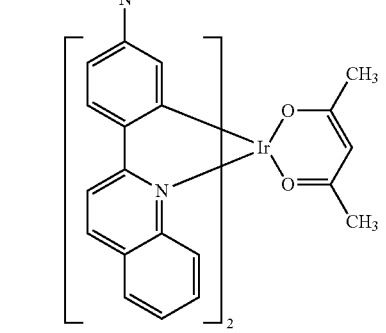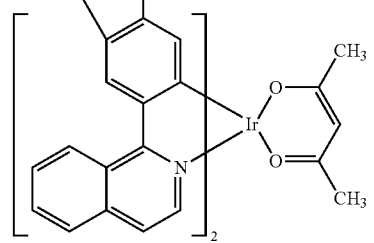

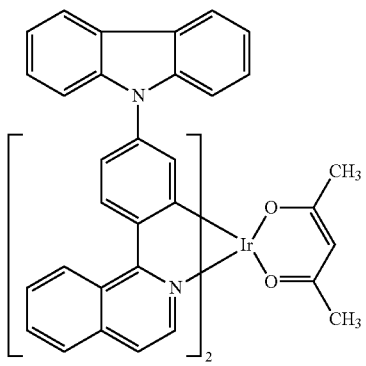

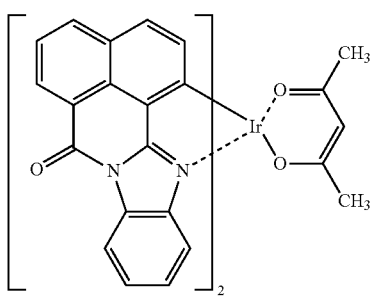

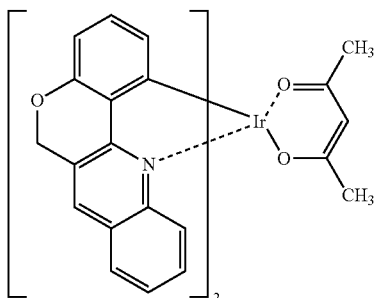

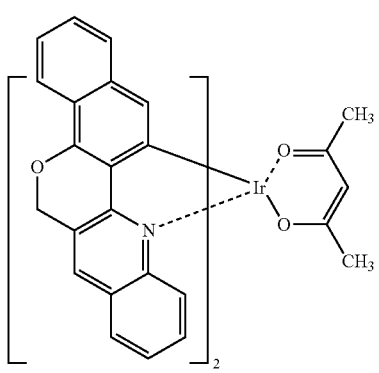

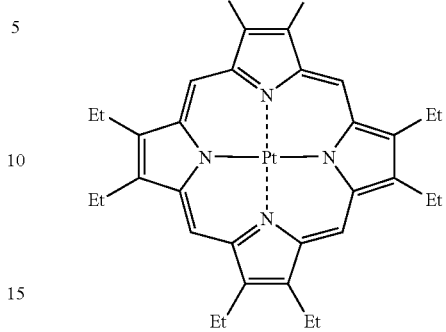

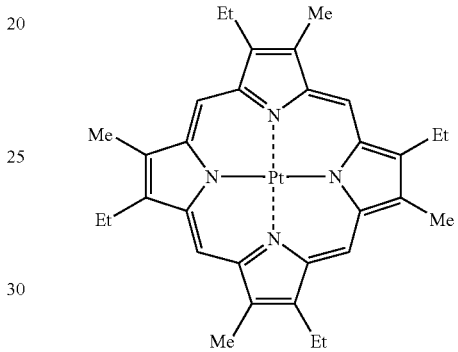

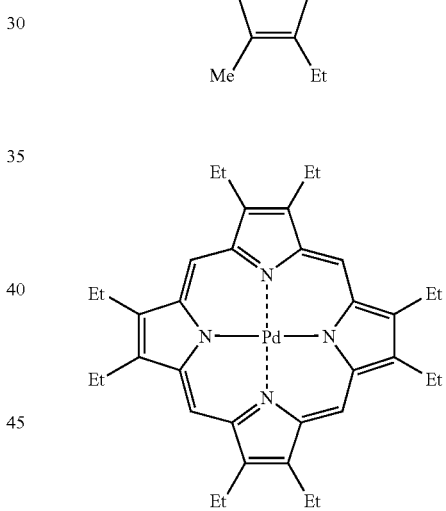

[Chemical Formula 42]

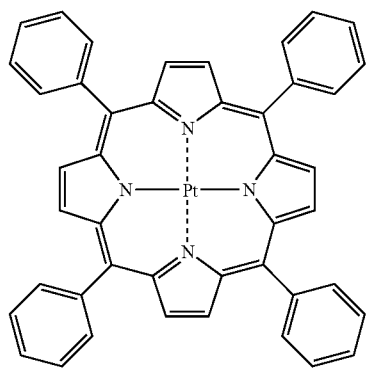

Of the organometallic complexes represented by Formulae (V), (Va), (Vb), and (Vc), typically preferred are compounds having, as ligand L and/or L', a 2-arylpyridine ligand such as an 2-arylpyridine, an 2-arylpyridine derivative having an arbitrary substituent, or an 2-arylpyridine derivative condensed with an arbitrary group.

Specific examples of the organometallic complexes represented by Formula (VI) are illustrated below, which, however, are not limitative at all. In the following formulae, Me represents a methyl group; and Et represents an ethyl group.

-continued

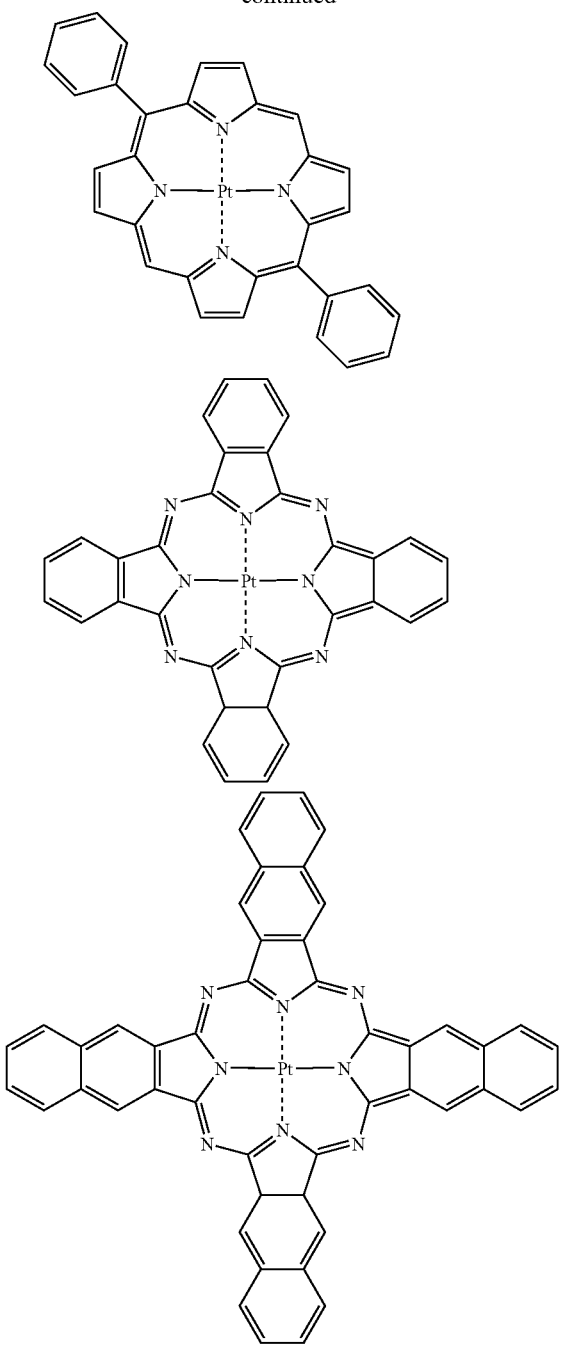

The molecular weight of such a phosphorescent dopant material is usually 4,000 or less, preferably 3,000 or less, and more preferably 2,000 or less and is usually 200 or more, preferably 300 or more, and more preferably 400 or more. If the molecular weight exceeds the upper limit, there might result seriously reduced sublimability which can cause troubles when vapor deposition is employed in the production of an electroluminescent device or might result a decreased solubility in an organic solvent which makes it difficult to conduct high purification (removal of substances causing deterioration) with an increase in the amount of impurities formed in the synthesizing steps. On the other hand, if the molecular weight is less than the lower limit, there results a reduced glass transition temperature, a reduced melting point, and a reduced gasification temperature, which may seriously spoil heat resistance.

When two or more different dopant materials are used, the hole blocking material in the hole blocking layer preferably has an oxidation potential greater than the greatest oxidation potential of the two or more different dopant materials.

When a light-emitting layer uses such an organometallic complex as a dopant material and emits phosphorescence, each of the organic compounds according to the present invention can be used alone or in combination as a host material for the light-emitting layer. The host material for use in the light-emitting layer giving phosphorescent emission may further include, in combination with one or more organic compounds according to the present invention, one or more of the materials having been described as host materials to be used in the light-emitting layer giving fluorescent emission (including aromatic amine compounds), carbazole derivatives such as 4,4'-N,N'-dicarbazolebiphenyl (PCT International Publication Number WO 00/70655), tris(8-hydroxyquinoline)aluminum (U.S. Pat. No. 6,303,238), (Appl. Phys. Lett., vol. 78, p. 1622, 2001), and polyvinylcarbazoles (Japanese Unexamined Patent Application Publication No. 2001-257076). The content of such other host materials, if contained in the light-emitting layer in combination with one or more organic compounds according to the present invention, is preferably 50 percent by weight or less relative to the organic compounds according to the present invention.

The amount of the organometallic complex to be contained as a dopant material in the light-emitting layer is preferably 0.1 percent by weight or more, and is preferably 30 percent by weight or less. If the amount is less than the lower limit, the complex might fail to contribute to the improvement of the luminous efficiency of the device whereas, if the complex exceeds the upper limit, there arises the possibility that concentration quenching takes place due typically to formation of a dimmer of the organometallic complex, leading to reduction of luminous efficiency.

There is a tendency that the amount of a dopant material in the light-emitting layer showing phosphorescent light emission is preferably somewhat larger than the amount of a fluorescent dye contained in the light-emitting layer in a device utilizing conventional fluorescence (singlet). When a fluorescent dye is contained in the light-emitting layer together with a phosphorescent dopant material, the amount of the fluorescent dye is preferably 0.05 percent by weight or more, more preferably 0.1 percent by weight or more, and is preferably 10 percent by weight or less, more preferably 3 percent by weight or less.

The thickness of the light-emitting layer 5 is usually 3 nm or more, preferably 5 nm or more, and is usually 200 nm or less, preferably 100 nm or less.

The light-emitting layer 5 can also be formed in the same manner as with the hole transport layer 4.

An organic compound according to the present invention as a host material for the light-emitting layer may be doped with the above-mentioned fluorescent dye and/or the phosphorescent dye (phosphorescent dopant material) as a dopant material, for example, in the following manner.

When the light-emitting layer 5 is formed by coating, a coating composition is prepared by dissolving the organic compound according to the present invention, a dopant material, and, as needed, a binder resin which does not function as a trap of electrons or as a emitted light-quenching agent in a solvent, and the coating composition is applied to the hole transport layer 4 typically by spin coating, followed by drying to form the light-emitting layer 5. Examples of the binder resin include polycarbonates, polyarylates, and polyesters. When added in a large amount, the binder resin may reduce the hole/electron mobility and, therefore, a smaller amount of the binder resin is desirable, with 50 percent by weight or less in terms of content in the light-emitting layer being preferred.

When the light-emitting layer 5 is formed by vacuum deposition, an organic compound according to the present invention is placed in a crucible placed in a vacuum chamber, a dopant material is placed in a different crucible, and the inside of the vacuum chamber is evacuated to a degree of vacuum of about $10^{-4}$ Torr using a proper vacuum pump. Thereafter, the crucibles are heated at the same time to evaporate them and form a layer on the substrate which is placed facing the crucibles. As an alternative process, the above-mentioned materials are mixed in a predetermined ratio to yield a mixture and the mixture is evaporated using one crucible.

When each dopant material is introduced into the light-emitting layer 5 by doping, it is uniformly distributed in a thickness direction of the light-emitting layer. However, there may be a concentration distribution of the dopant material in the thickness direction. For example, doping may be conducted only in the vicinity of the interface with the hole transport layer 4 or, reversely, may be conducted in the vicinity of the hole blocking layer 6.

The light-emitting layer 5 can be formed in the same manner as with the hole transport layer 4 but, usually, is formed by vacuum deposition.

The light-emitting layer 5 may further contain other components in addition to the above-mentioned components, within ranges not adversely affecting the performance according to the present invention.

Hole Blocking Layer

In the device shown in FIG. 1, a hole blocking layer 6 is arranged on the light-emitting layer 5 so as to be in contact with one of the interfaces of the light-emitting layer 5 near to the cathode.

The hole blocking layer 6 is preferably formed by a compound which serves to prevent holes migrating from the hole transport layer 4 from reaching the cathode 8 and which can effectively transport electrons injected from the cathode 8 toward the light-emitting layer 5. Physical properties required for a material constituting the hole blocking layer 6 include a high electron mobility and a low hole mobility. The hole blocking layer 6 has the function of confining holes and electrons within the light-emitting layer 5 to thereby improve luminous efficiency.

The ionization potential of the hole blocking layer 6 to be arranged in an organic electroluminescent device according to the present invention is preferably larger than the ionization potential of the light-emitting layer 5 (when the light-emitting layer 5 contains both a host material and a dopant material, the ionization potential of the host material) by 0.1 eV or more. The ionization potential is defined in terms of energy necessary to release an electron at HOMO (highest occupied molecular orbital) level of a substance to a vacuum level. The ionization potential can be directly defined by the photoelectron spectrometry. Alternatively, it can be determined by correcting an electrochemically measured oxidation potential based on a reference electrode. In the latter process using, for example, a saturated calomel electrode (SCE) as the reference electrode, the ionization potential is defined according to the following equation (Molecular Semiconductors, Springer-Verlag, 1985, p. 98):

Ionization potential=(Oxidation potential(vs. SCE))+ 4.3 eV

Further, electron affinity (EA) of the hole blocking layer 6 to be arranged in an organic electroluminescent device according to the present invention is preferably equal to or more than the electron affinity of the light-emitting layer 5 (when the light-emitting layer 5 contains both a host material and a dopant material, the electron affinity of the host material). The electron affinity is defined in terms of energy released when an electron in a vacuum level falls to LUMO (lowest unoccupied molecular orbital) level to stabilize with taking the vacuum level as a standard as with the ionization potential. The electron affinity is similarly determined by subtracting an optical band gap from the ionization potential or determining from an electrochemical reduction potential according to the following equation:

Electron affinity=(Reduction potential (vs. SCE))+4.3 eV

Therefore, the hole blocking layer 6 to be arranged in an organic electroluminescent device according to the present invention can also be expressed as follows using oxidation potential and reduction potential:

(Oxidation potential of the hole blocking material)−(Oxidation potential of the light-emitting layer material)≧0.1 V (Reduction potential of the hole blocking material)≧(Reduction potential of the light-emitting layer material)

Further, in a device having an electron transport layer 7 to be described below, the electron affinity of the hole blocking layer 6 is preferably equal to or lower than the electron affinity of the electron transport layer 7. Accordingly, the following condition is preferably satisfied:

(Reduction potential of the electron transporting material)≧(Reduction potential of the hole blocking material)≧(Reduction potential of the light-emitting layer material)

In this condition, when two or more different electron transporting materials, two or more different hole blocking materials, or two or more different light-emitting layer materials are used, one having the smallest reduction potential is employed for comparison in the condition; and when the light-emitting layer 5 contains both host materials and dopant materials, one of the host materials having the smallest reduction potential is employed for comparison in the condition.

A preferred example of hole blocking materials satisfying such conditions includes a mixed ligand complex represented by following Formula (VII):

[Chemical Formula 43]

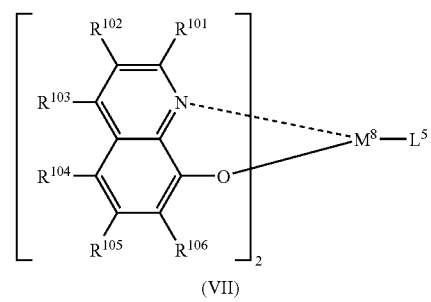

(VII)

wherein $R^{101}$, $R^{102}$, $R^{103}$, $R^{104}$, $R^{105}$, and $R^{106}$ each independently represent a hydrogen atom or an arbitrary substituent; $M^8$ represents a metal atom selected from aluminum, gallium, and indium; and L⁵ is represented by any one of following Formulae (VIIa), (VIIb), and (VIIc):

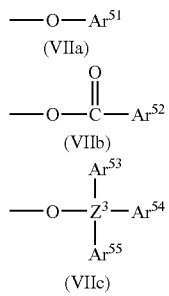

wherein $Ar^{51}$, $Ar^{52}$, $Ar^{53}$, $Ar^{54}$, and $Ar^{55}$ each independently represent an aromatic hydrocarbon group which may be substituted or an aromatic heterocyclic group which may be substituted; and $Z^3$ represents silicon or germanium.

In Formula (VII), $R^{101}$ to $R^{106}$ each independently represent a hydrogen atom or an arbitrary substituent. Preferred examples of $R^{101}$ to $R^{106}$ include hydrogen atom; halogen atoms such as chlorine and bromine; alkyl groups having one to six carbon atoms, such as methyl group and ethyl group; aralkyl groups such as benzyl group; alkenyl groups having two to six carbon atoms, such as vinyl group; cyano group; amino groups; acyl groups; alkoxy groups having one to six carbon atoms, such as methoxy group and ethoxy group; alkoxycarbonyl groups having two to six carbon atoms, such as methoxycarbonyl group and ethoxycarbonyl group; carboxyl group; aryloxy groups such as phenoxy group and benzyloxy group; dialkylamino groups such as diethylamino group and diisopropylamino group; diaralkylamino groups such as dibenzylamino group and diphenethylamino group; α-haloalkyl groups such as trifluoromethyl group; hydroxy group; aromatic hydrocarbon groups which may be substituted, such as phenyl group and naphthyl group; and aromatic heterocyclic groups which may be substituted, such as thienyl group and pyridyl group.

Examples of substituents which the aromatic hydrocarbon groups and aromatic heterocyclic groups may have include halogen atoms such as fluorine atom; alkyl groups having one to six carbon atoms, such as methyl group and ethyl group; alkenyl groups having two to six carbon atoms, such as vinyl group; alkoxycarbonyl groups having two to six carbon atoms, such as methoxycarbonyl group and ethoxycarbonyl group; alkoxy groups having one to six carbon atoms, such as methoxy group and ethoxy group; aryloxy groups such as phenoxy group and benzyloxy group; dialkylamino groups such as dimethylamino group and diethylamino group; acyl groups such as acetyl group; haloalkyl groups such as trifluoromethyl group; and cyano group.

More preferred examples of $R^{101}$ to $R^{106}$ include hydrogen atom, alkyl groups, halogen atoms, and cyano group. As $R^{104}$, cyano group is especially preferred.

Specific examples of $Ar^{51}$ to $Ar^{55}$ in Formulae (VIIa), (VIIb), and (VIIc) include aromatic hydrocarbon groups which may be substituted, such as phenyl group, biphenyl group, and naphthyl group; and aromatic heterocyclic groups which may be substituted, such as thienyl group and pyridyl group.

Preferred specific examples of the compounds represented by Formula (VII) will be illustrated below, which are, however, by no means limitative.

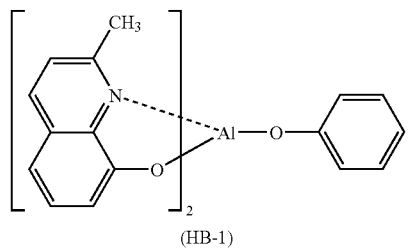
(HB-1)

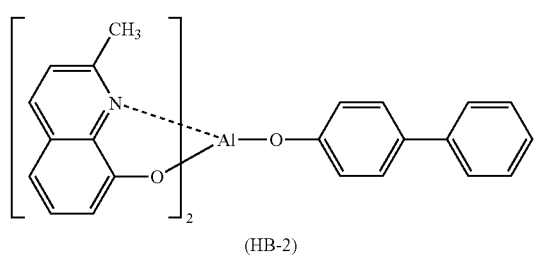
(HB-2)

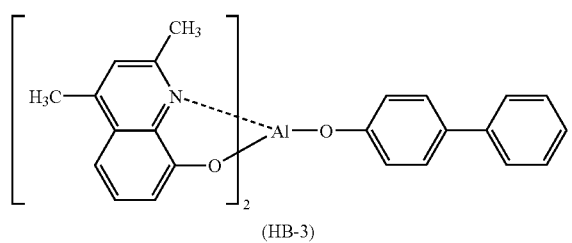
(HB-3)

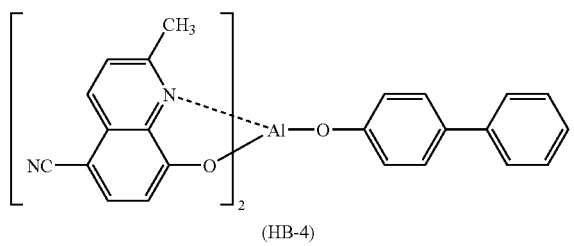
(HB-4)

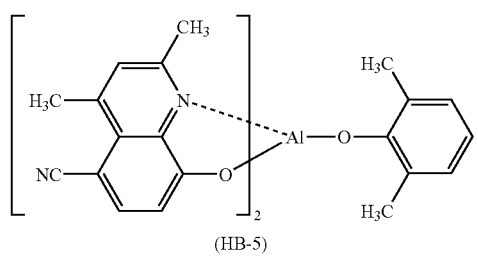
(HB-5)

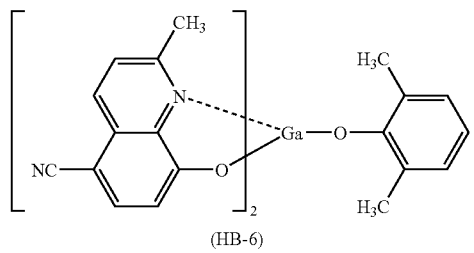
(HB-6)

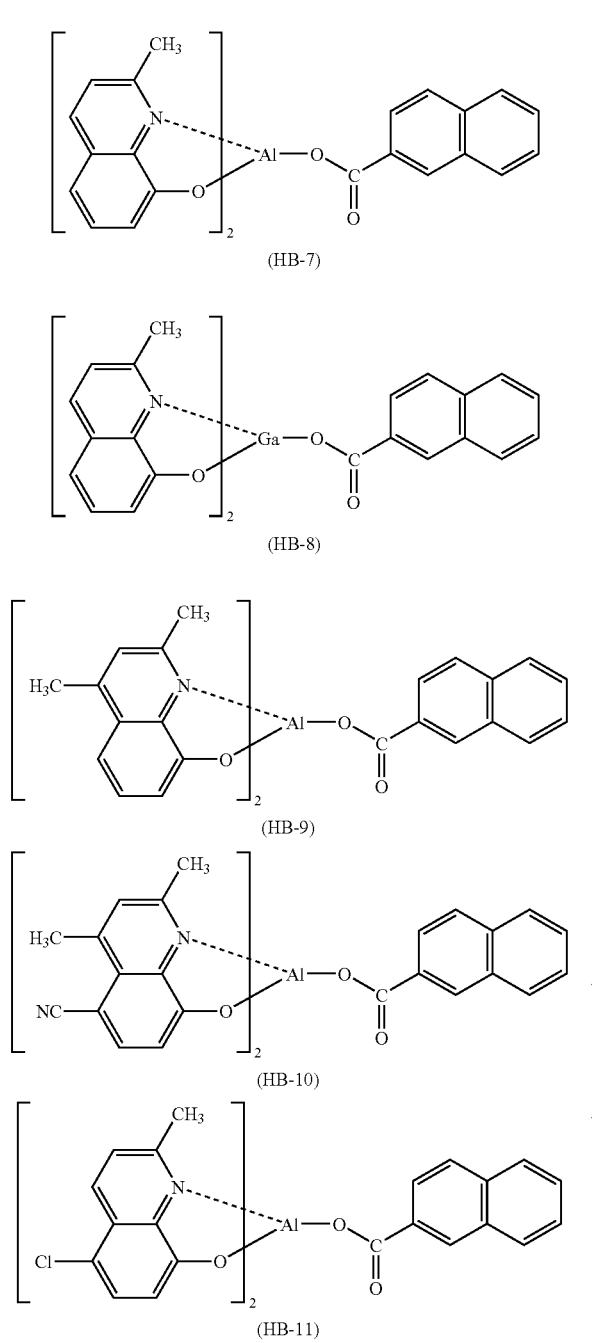
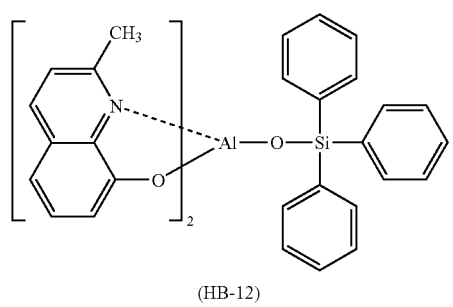
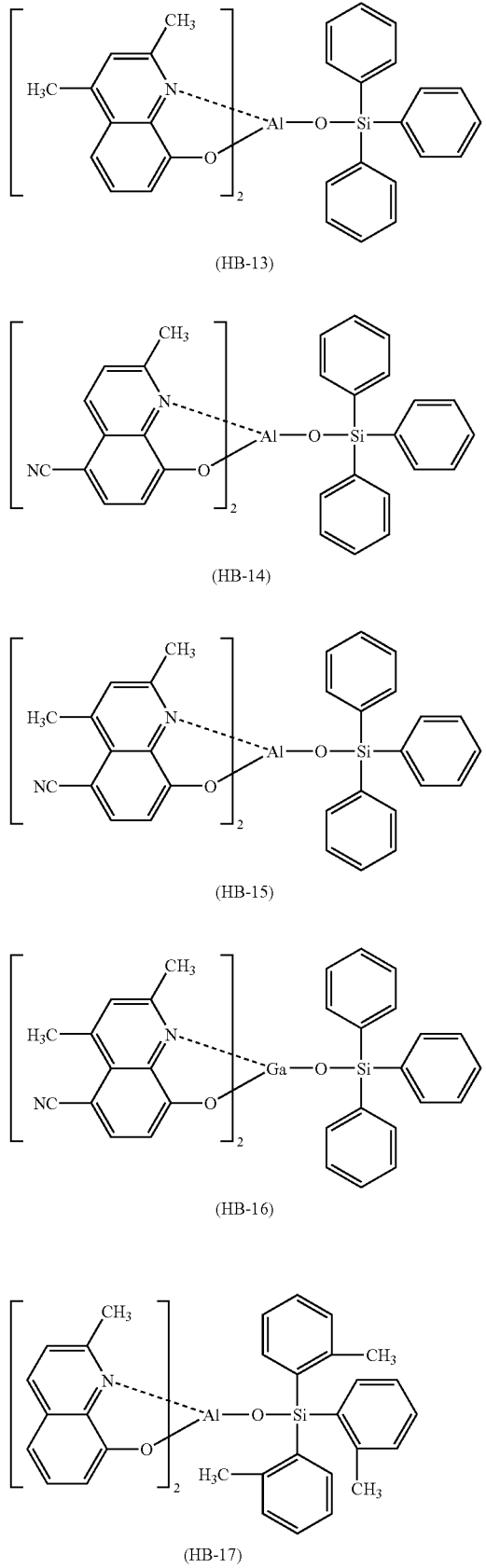

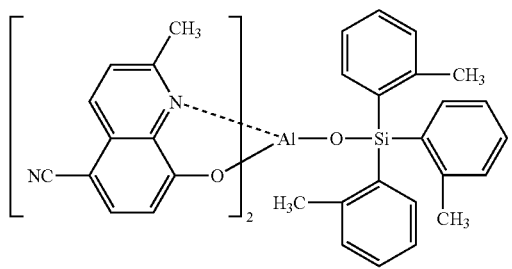

(HB-18)

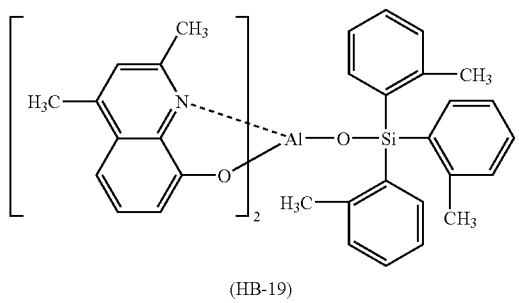

(HB-19)

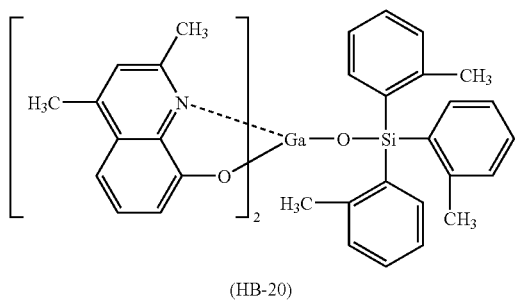

(HB-20)

Each of these compounds can be used alone or in combination according to necessity in the hole blocking layer 6.

Such hole blocking materials also include, in addition to the mixed ligand complexes represented by Formula (VII), compounds having at least one residue derived from 1,2,4-triazole ring and represented by the following structural formula:

[Chemical Formula 47]

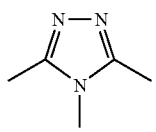

Specific examples of the compounds having at least one residue derived from 1,2,4-triazole ring and represented by the structural formula will be illustrated below, which are, however, by no means limitative.

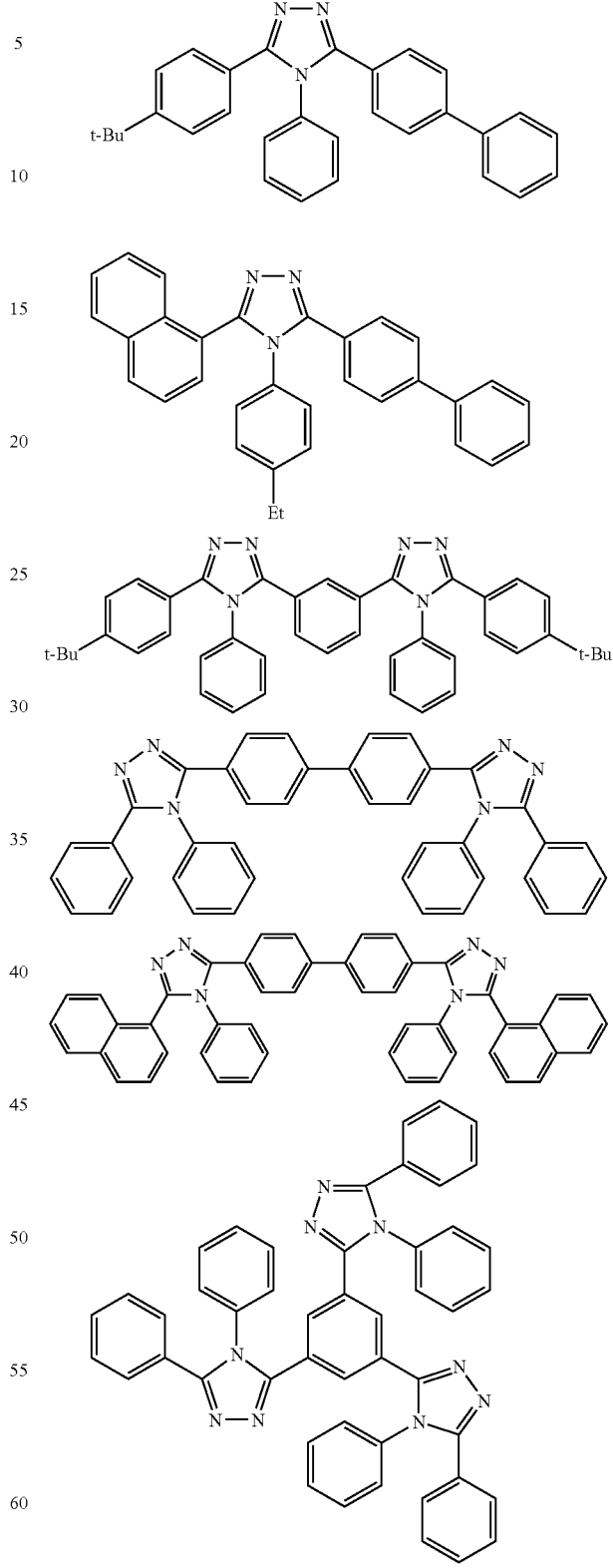

[Chemical Formula 48]

Hole blocking materials further include compounds having at least one phenanthroline ring represented by the following structural formula:

[Chemical Formula 49]

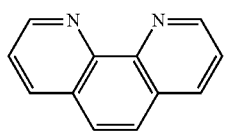

Specific examples of the compounds having at least one phenanthroline ring represented by the structural formula will be illustrated below, which are, however, by no means limitative.

[Chemical Formula 50]

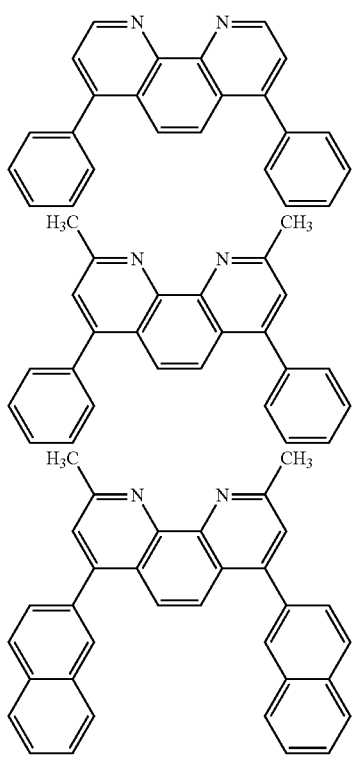

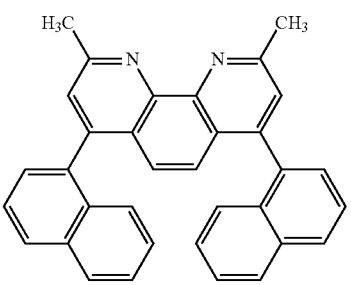

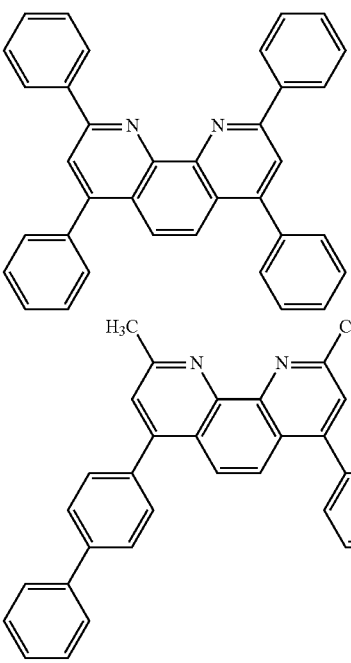

A compound including a pyridine ring intramolecularly having substituents at the 2-, 4-, and 6-positions is also preferably used as a hole blocking material. Specific examples of such compounds are illustrated below.

[Chemical Formula 51]

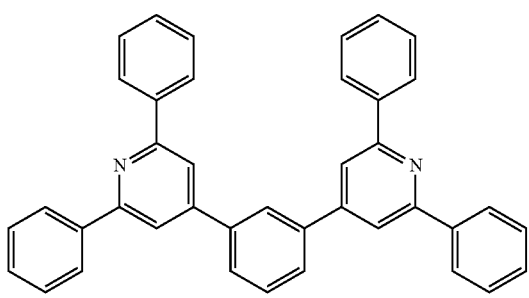

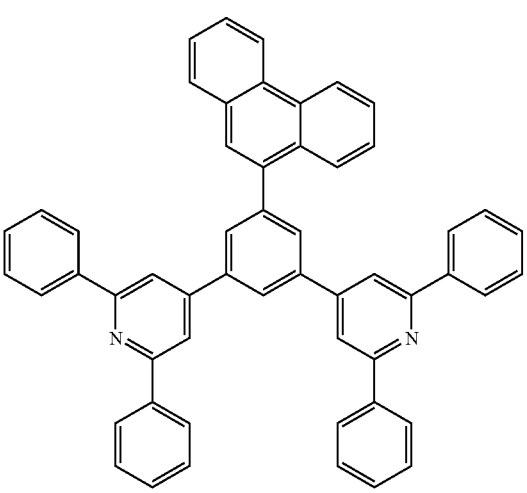

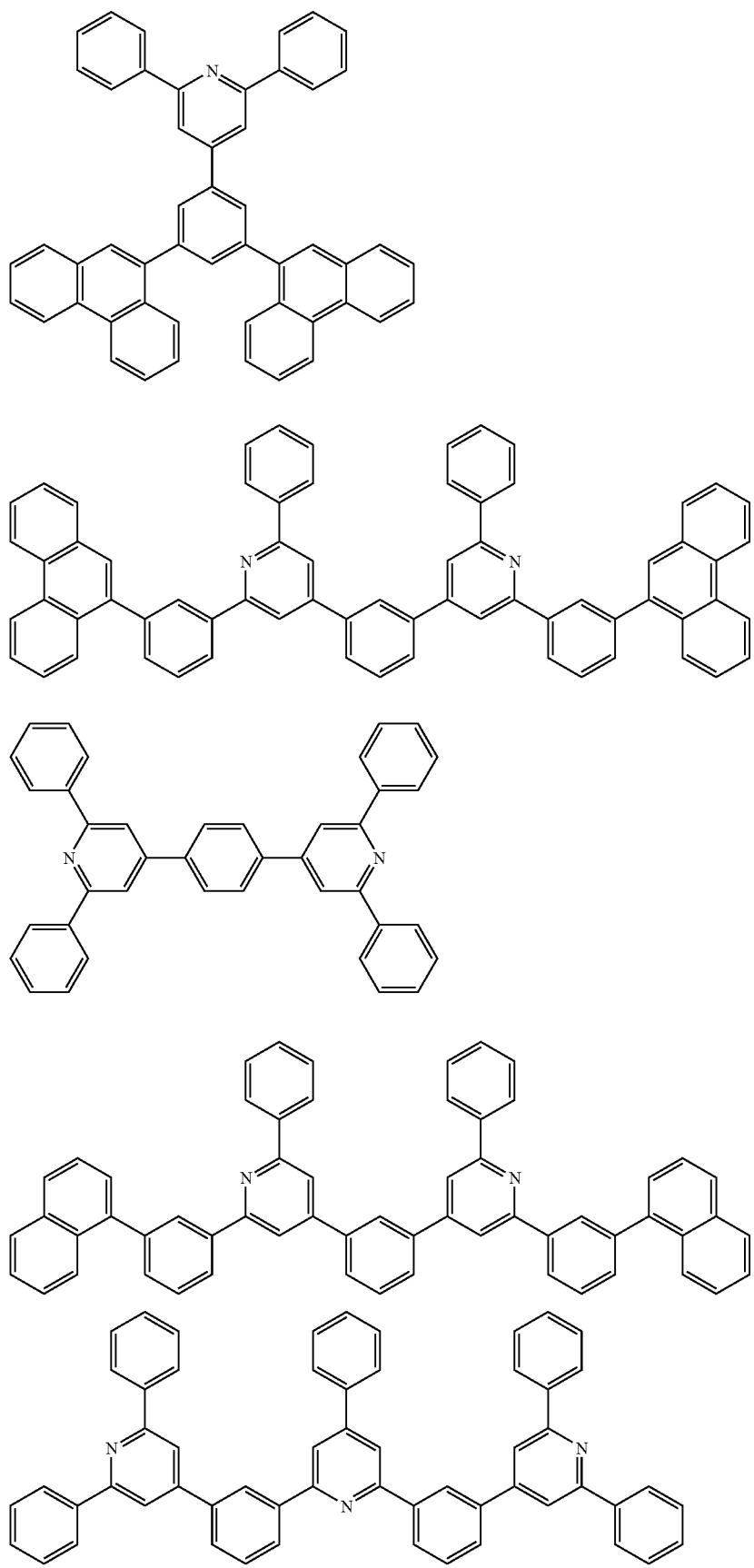

-continued

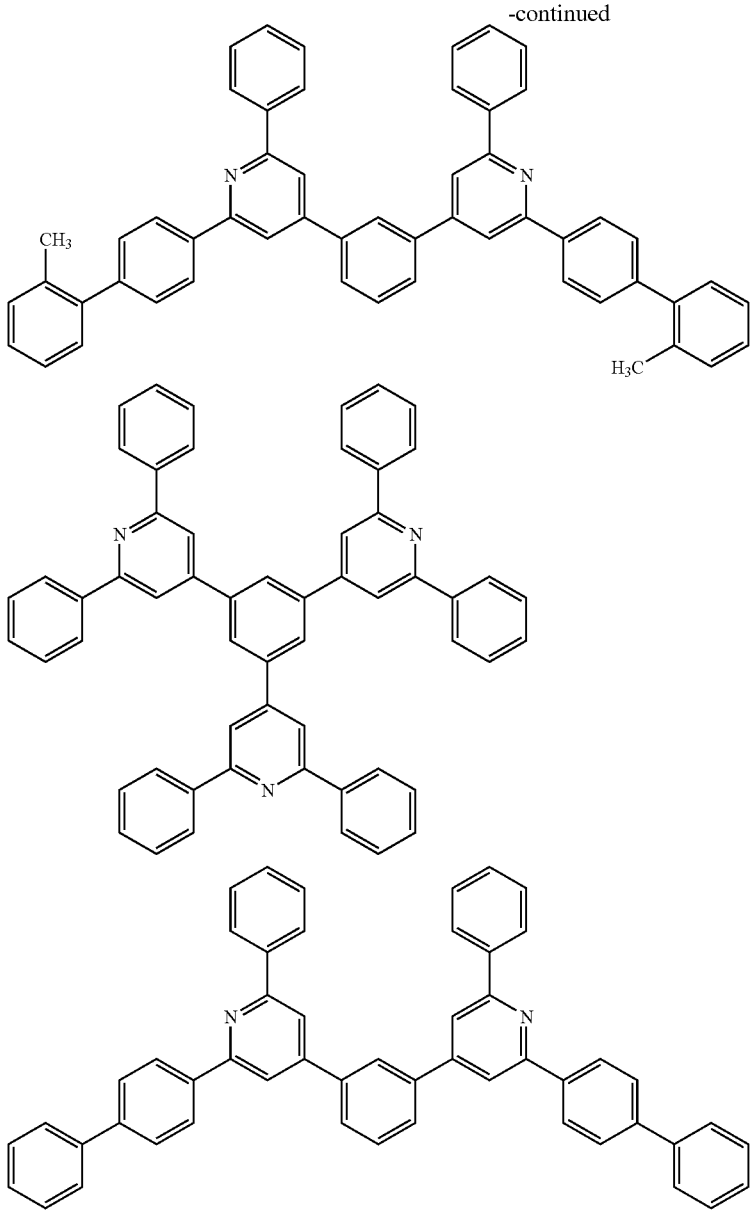

The thickness of the hole blocking layer 6 is generally 0.3 nm or more, preferably 0.5 nm or more and is generally 100 nm or less, preferably 50 nm or less.

The hole blocking layer 6 can be formed in the same manner as with the hole transport layer 4, but it is generally formed by vacuum deposition.

An organic electroluminescent device according to the present invention, however, can exhibit sufficiently satisfactory properties even when no hole blocking layer is provided, as described in after-mentioned Examples. This is because the organic compound for use in the present invention is excellent as a host material in a light-emitting layer of such an organic electroluminescent device.

Cathode

The cathode 8 serves to inject electrons into the light-emitting layer 5 through the hole blocking layer 6. As the material to be used as the cathode 8, those materials which are used for the anode 2 may be employed but, in order to inject electrons with a high efficiency, metals having a low work function are preferred. Thus, suitable metals such as tin, magnesium, indium, calcium, aluminum, and silver or alloys thereof are used. Specific examples thereof include electrodes of alloys having a low work function, such as a magnesium-silver alloy, a magnesium-indium alloy, and a aluminum-lithium alloy.

The thickness of the cathode 8 is generally as with the anode 2.

A metal layer having a high work function and stable in the atmosphere may be arranged on the cathode 8 in order to protect the cathode 8 including such a metal having a low work function. This improves the stability of the device. For this purpose, metals such as aluminum, silver, copper, nickel, chromium, gold and platinum are used.

Further, in order to improve efficiency of the device, it is also an effective technique to arrange an extremely thin insulating film of LiF, $MgF_2$ or $Li_2O$ at the interface between the cathode 8 and the light-emitting layer 5 or the electron transport layer 7 (Appl. Phys. Lett., vol. 70, p. 152, 1997; Japanese Unexamined Patent Application Publication No. 10-74586; and IEEE Trans. Electron. Devices, vol. 44, p. 1245, 1997).

Electron Transport Layer

For further improving luminous efficiency of the device, an electron transport layer 7 is preferably arranged between the hole blocking layer 6 and the cathode 8 as shown in FIGS. 2 and 3. The electron transport layer 7 is formed from a compound which can efficiently transport electrons injected from the cathode 8 toward the hole blocking layer 6 between the energized electrodes.

Examples of the material satisfying such conditions include metal complexes such as aluminum complex of 8-hydroxyquinoline (Japanese Unexamined Patent Application Publication No. 59-194393); metal complexes of 10-hydroxybenzo[h]quinoline; oxadiazole derivatives; distyrylbiphenyl derivatives; silole derivatives; metal complexes of 3- or 5-hydroxyflavone; metal complexes of benzoxazole; metal complexes of benzothiazole; trisbenzimidazolylbenzene (U.S. Pat. No. 5,645,948), quinoxaline compounds (Japanese Unexamined Patent Application Publication No. 6-207169); phenanthroline derivatives (Japanese Unexamined Patent Application Publication No. 5-331459); 2-t-butyl-9,10-N,N'-dicyanoanthraquinonediimine; n-type hydrogenated amorphous silicon carbide; n-type zinc sulfide; and n-type zinc selenide.

It is preferred to dope the electron transporting material described above with an alkali metal (described typically in Japanese Unexamined Patent Application Publications No. 10-270171, No. 2002-100478, and No. 2002-100482) since it serves to improve the electron transporting ability.

When the electron transport layer 7 is arranged, the hole blocking layer 6 preferably has an electron affinity equal to or lower than the electron affinity of the electron transport layer 7.

The reduction potentials of the light-emitting layer material for use in the light-emitting layer 5, the hole blocking material in the hole blocking layer 6, and the electron transporting material in the electron transport layer preferably satisfy the following condition, for adjusting light emitting regions and reducing the drive voltage.

(Reduction potential of the electron transporting material)≧(Reduction potential of the hole blocking material)≧(Reduction potential of the light-emitting layer material)

In this connection, when two or more different electron transporting materials, two or more different hole blocking materials, or two or more different light-emitting layer materials are used, one having the smallest reduction potential is used for comparison in the formula; and when the light-emitting layer 5 contains both host materials and dopant materials, one of the host materials having the smallest reduction potential is used for comparison in the formula.

The above-mentioned hole blocking materials may be used in the electron transport layer 7. In this case, each of the hole blocking materials can be used alone or in combination to form the electron transport layer 7.

The thickness of the electron transport layer 6 is generally 5 nm or more, preferably 10 nm or more and is generally 200 nm or less, preferably 100 nm or less.

The electron transport layer 7 may be formed on the hole blocking layer 6 by coating or vacuum deposition, in the same manner as with the hole transport layer 4, whereas it is generally formed by vacuum deposition.

Hole Injection Layer

A hole injection layer 3 may be arranged between the hole transport layer 4 and the anode 2 (FIG. 3), for further improving efficiency of injecting holes and improving adhesion of the whole organic layers onto the anode 2. Arrangement of the hole injection layer 3 serves to provide the effect of reducing the initial drive voltage of the device and, at the same time, depressing an increase in voltage upon continuous driving of the device at a constant current.

As to requirements for materials to be used in the hole injection layer 3, the materials are required to have a good contact with the anode 2, form a uniform thin film, and be thermally stable. Specifically, they preferably have a high melting point and a high glass transition temperature, with the melting point being preferably 300° C. or higher, and the glass transition temperature being 100° C. or higher. In addition, the materials are required to have a sufficiently low ionization potential to facilitate injection of holes from the anode 2 and have a large hole mobility.

As materials for the hole injection layer 3 to be arranged for this purpose, there have been reported organic compounds such as porphyrin derivatives and phthalocyanine derivatives (Japanese Unexamined Patent Application Publication No. 63-295695), hydrazone compounds, alkoxy-substituted aromatic diamine derivatives, p-(9-anthryl)-N,N'-di-p-tolylaniline, polythienylenevinylenes and poly-p-phenylenevinylenes, polyanilines (Appl. Phys. Lett., vol. 64, p. 1245, 1994), polythiophenes (Optical Materials, vol. 9, p. 125, 1998) and star-burst type aromatic triamines (Japanese Unexamined Patent Application Publication No. 4-308688); sputtered carbon films (Synth. Met., vol. 91, p. 73, 1997); and metal oxides such as vanadium oxide, ruthenium oxide, and molybdenum oxide (J. Phys. D, vol. 29, p. 2750, 1996).

There may also be employed a layer containing a hole injecting and transporting, low-molecular organic compound and an electron acceptive compound (described typically in Japanese Unexamined Patent Application Publications No. 11-251067 and No. 2000-159221), a layer including an aromatic amino group-containing, non-conjugated polymer doped with, as needed, an electron accepter (e.g., Japanese Unexamined Patent Application Publications No. 11-135262, No. 11-283750, No. 2000-36390, No. 2000-150168, and No. 2001-223084; and PCT International Publication Number WO 97/33193) and a layer containing a conductive polymer such as a polythiophene (Japanese Unexamined Patent Application Publication No. 10-92584) which, however, are not limitative at all.

As materials for the hole injection layer 3, either of low-molecular compounds and polymer may be used.

Of the low-molecular compounds, porphine compounds and phthalocyanine compounds are popularly used. These compounds may have a central metal or may be metal-free.

Preferred examples of these compounds include the following compounds:
porphine,
5,10,15,20-tetraphenyl-21H,23H-porphine,
5,10,15,20-tetraphenyl-21H,23H-porphine cobalt(II),
5,10,15,20-tetraphenyl-21H,23H-porphine copper(II),
5,10,15,20-tetraphenyl-21H,23H-porphine zinc(II),
5,10,15,20-tetraphenyl-21H,23H-porphine vanadium(IV) oxide,
5,10,15,20-tetra(4-pyridyl)-21H,23H-porphine,
29H,31H-phthalocyanine,
copper(II) phthalocyanine,
zinc(II) phthalocyanine,
titanium phthalocyanine oxide,
magnesium phthalocyanine,
lead phthalocyanine, and
copper(II) 4,4'4'',4'''-tetraaza-29H,31H-phthalocyanine A thin film constituting the hole injection layer 3 may be formed in the same manner as with the hole transport layer 4.

When an inorganic material is used, the thin film can also be formed by sputtering, electron-beam evaporation, or plasma chemical vapor deposition (plasma CVD).

When formed from a low-molecular compound, the thickness of the hole injection layer 3 is such that the lower limit is generally about 3 nm, preferably about 10 nm, and the upper limit is generally about 100 nm, preferably about 50 nm.

When a polymer compound is used as a material for the hole injection layer 3, the hole injection layer 3 may be formed, for example, by dissolving in a solvent the polymer compound, the electron accepter and, as needed, a binder resin and/or an additive such as a coating property-improving agent (e.g., a leveling agent) which does not function as a trap of holes, for example, to prepare a coating composition, and applying the coating composition to the anode 2 according to a common coating procedure such as spray coating, printing, spin coating, dip coating, or die coating or by an ink jet process, followed by drying to form the hole injection layer 3. Examples of the binder resin include polycarbonates, polyarylates, and polyesters. When added in a large amount, the binder resin might reduce the hole mobility, and hence the amount is preferably small, with 50 percent by weight or less in terms of content in the hole injection layer 3 being preferred.

It is also possible to previously form a thin film on a medium such as a film, a supporting substrate or a roll according to the thin film-forming process and transferring the thin film from the medium onto the anode 2 by applying heat or pressure to thereby form a thin film.

The lower limit of the thickness of the hole injection layer 3 formed as described hereinbefore is usually about 5 nm, preferably about 10 nm, and the upper limit is usually about 1,000 nm, preferably about 500 nm.

An organic electroluminescent device according to the present invention can have a reverse structure to that shown in FIG. 1. In the reverse structure, on a substrate 1, there are arranged a cathode 8, a hole blocking layer 6, a light-emitting layer 5, a hole transport layer 4, and an anode 2 in this order. An organic electroluminescent device according to the present invention can also be arranged between two substrates, one of which is optically highly transparent, as described above. Likewise, the components can be laminated in reverse order to those described in FIGS. 2 and 3, respectively. The layer structures shown in FIGS. 1 to 3 may each further include any arbitrary layer or layers, in addition to the layers mentioned above, within ranges not departing from the scope and spirit of the present invention. In addition, modifications and variations can be made as appropriate. For example, a layer structure can be simplified by arranging a layer having the functions of two or more of the above-mentioned layers.

Further, it is possible to employ a top emission structure or to use transparent electrodes as the cathode and the anode to prepare a transparent device or, further, to employ a layer structure wherein a plurality of the layer structures shown in FIG. 1 are stacked (a structure wherein a plurality of the light-emitting units are stacked). In this case, $V_2O_5$, for example, is preferably used as a charge generating layer (CGL) instead of the interface layers (when ITO and aluminum (Al) are used as the anode and the cathode, respectively, the two layers of the anode and the cathode) between the units (light-emitting units). This serves to reduce barrier between the units, thus being more preferred in view of luminous efficiency and drive voltage.

The present invention can be applied to any of structures of organic luminescent devices, such as a structure in which the organic electroluminescent device includes a single device, a structure which includes devices arranged in an array form, and a structure wherein the anode and the cathode are arranged in an X-Y matrix pattern.

EXAMPLES

Next, the present invention will be illustrated in further detail with reference to several examples below, which, however, are not limitative at all, as long as not exceeding the scope and the spirit of the present invention.

[Synthesis Examples of Organic Compounds]

Organic compounds useable as organic compounds according to the present invention and charge transporting materials according to the present invention may be synthetically prepared, for example, according to the following Synthesis Examples. In the following examples, the glass transition temperature (Tg) was determined by differentiation scanning calorimetry (DSC), the gasification temperature was determined by thermogravimetry/differential thermal analysis (TG-DTA), and the melting point was determined by differentiation scanning calorimetry (DSC) or thermogravimetry/differential thermal analysis (TG-DTA).

Synthesis Example 1

(i) Synthesis of Target Compound 1

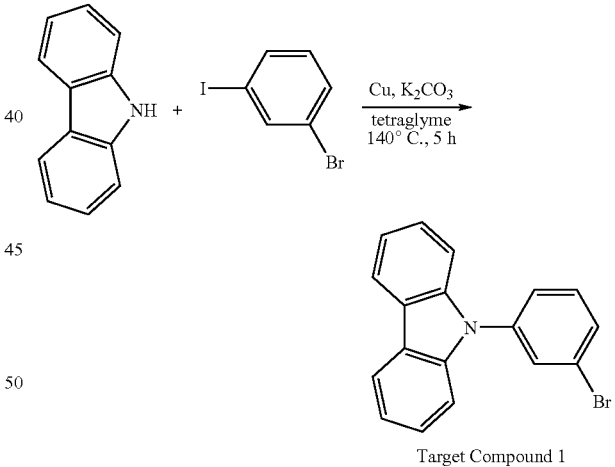

[Chemical Formula 52]

Target Compound 1

A mixture of carbazole (7.00 g), 3-bromoiodobenzene (14.2 g), copper powder (2.66 g), potassium carbonate (5.79 g), and Tetraglyme (10 ml) was stirred with heating at 140° C. in a nitrogen stream for five hours, followed by standing to cool to room temperature. After the completion of reaction, the reaction mixture was combined with chloroform, and insoluble components were separated by filtration. Chloroform was distilled off from the filtrate under reduced pressure, and the residue was purified by silica gel column chromatography (n-hexane/toluene=4/1). By drying under reduced pressure, Target Compound 1 (10.5 g, in a yield of 78%) was obtained as a colorless viscous liquid.

(ii) Synthesis of Target Compound 2

[Chemical Formula 53]

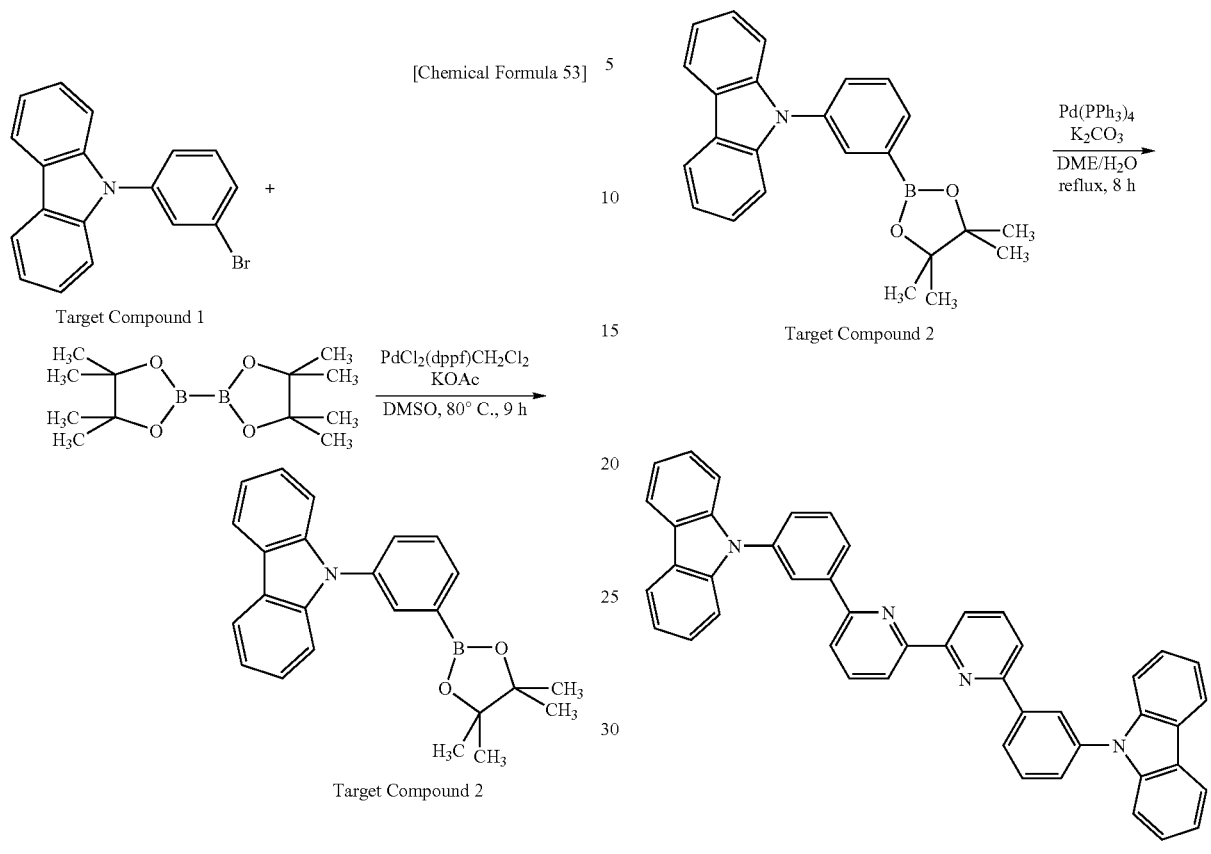

A mixture of Target Compound 1 (10.5 g), bis(pinacolatodiboron) (9.93 g), potassium acetate (10.9 g), and anhydrous dimethyl sulfoxide (DMSO) (190 ml) was stirred with heating at 60° C. in a nitrogen stream for fifteen minutes, and the mixture was combined with [1,1'-bis(diphenylphosphino)ferrocene]dichloropalladium(II) dichloromethane complex (0.799 g) and further stirred with heating at 80° C. for nine hours. After standing to cool to room temperature, the reaction mixture was combined with water (250 ml) and toluene (500 ml), followed by stirring. After reextracting the aqueous layer with toluene twice, the organic layers were combined, and the mixture was combined with magnesium sulfate and activated clay. Magnesium sulfate and activated clay were separated by filtration, and toluene was distilled off under reduced pressure to precipitate crystals. The crystals were washed with cold methanol, dried under reduced pressure, and thereby yielded Target Compound 2 (9.86 g, in a yield of 80%) as white crystals.

(iii) Synthesis of Target Compound 3

[Chemical Formula 54]

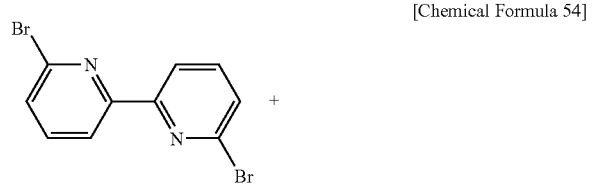

A mixture of 6,6'-dibromo-2,2'-bipyridyl (1.50 g), Target Compound 2 (4.23 g), potassium carbonate (3.96 g), ethylene glycol dimethyl ether (18 ml), and water (6 ml) was stirred with heating at 60° C. in a nitrogen stream for fifteen minutes, and the mixture was combined with tetrakis(triphenylphosphine)palladium(0) (0.277 g) and further stirred with heating under reflux for eight hours. After standing to cool to room temperature, the reaction mixture was combined with methanol (100 ml), followed by stirring to yield a precipitate. The precipitate was recovered by filtration, washed with a mixture of methanol/water, and dried under reduced pressure to yield crystals. The crystals were purified by silica gel column chromatography (n-hexane/methylene chloride=2/1), washed with a mixture of methylene chloride/methanol, dried under reduced pressure, and thereby yielded Target Compound 3 (1.63 g, in a yield of 53%) as white crystals. The white crystals (1.51 g) were purified by sublimation to recover 1.41 g of a white solid.

This was identified as Target Compound 3 through desorption electron ionization-mass spectrometry (DEI-MS) (m/z=638 ($M^+$)).

This compound had a glass transition temperature of 115° C., a melting point of 252° C., and a gasification temperature of 508° C.

Synthesis Example 2

(i) Synthesis of Target Compound 4

[Chemical Formula 55]

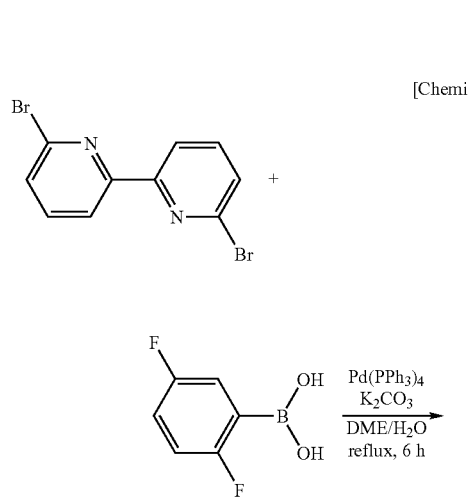

Target Compound 4

(ii) Synthesis of Target Compound 5

[Chemical Formula 56]

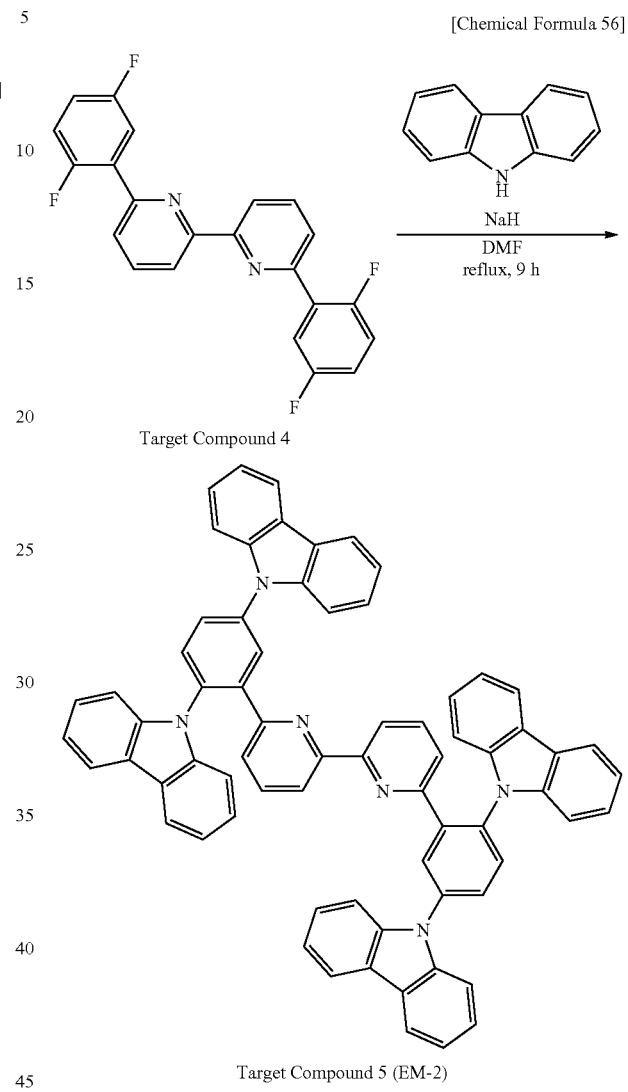

Target Compound 5 (EM-2)

A mixture of 6,6'-dibromo-2,2'-bipyridyl (2.00 g), 2,5-difluorophenylboronic acid (2.41 g), potassium carbonate (4.40 g), ethylene glycol dimethyl ether (25 ml), and water (13 ml) was stirred with heating at 60° C. in a nitrogen stream for fifteen minutes and combined with tetrakis(triphenylphosphine)palladium(0) (0.368 g), followed by stirring with heating under reflux for six hours. After standing to cool to room temperature, the reaction mixture was combined with methanol (100 ml), followed by stirring to yield a precipitate. The precipitate was recovered by filtration, washed with a mixture of methanol/water, and dried under reduced pressure to yield crystals. The crystals were dissolved in chloroform (150 ml) to yield a solution, and the solution was combined with activated clay and stirred with heating under reflux for one hour. Insoluble components were separated by filtration, and the filtrate was concentrated to precipitate crystals. The crystals were washed with methanol, dried under reduced pressure, and thereby yielded Target Compound 4 (2.16 g, in a yield of 89%) as white crystals.

A suspension of sodium hydride (55%, 1.65 g) in anhydrous N,N-dimethylformamide (100 ml) was combined with carbazole (6.33 g) in a nitrogen stream, followed by stirring with heating at 80° C. for one hour. The mixture was further combined with Target Compound 4 (1.80 g) and stirred with heating under reflux for nine hours. This was combined with water (70 ml) and methanol (70 ml) under cooling with ice to yield a precipitate. The precipitate was separated by filtration, washed with methanol, and dried under reduced pressure to yield crystals. The crystals were purified by silica gel column chromatography (chloroform), washed with ethyl acetate and a mixture of chloroform/methanol, dried under reduced pressure, and thereby yielded Target Compound 5 (2.15 g, in a yield of 47%) as white crystals. The white crystals (1.77 g) were purified by sublimation to recover 1.20 g of a white solid.

This was identified as Target Compound 5 through DEI-MS (m/z=968 ($M^+$)).

This compound had a glass transition temperature of 180° C., a crystallization temperature of 288° C., a melting point of 364° C., and a gasification temperature of 553° C.

Synthesis Example 3

(i) Synthesis of Target Compound 6

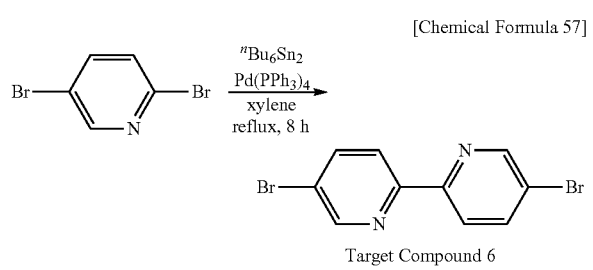

[Chemical Formula 57]

A mixture of 2,5-dibromopyridine (3.00 g), bis(tributyltin) (3.54 ml), and anhydrous xylene (100 ml) was stirred with heating at 60° C. in a nitrogen stream for fifteen minutes, and combined with tetrakis(triphenylphosphine)palladium(0) (0.351 g), followed by stirring with heating under reflux for eight hours. After standing to cool to room temperature, the reaction mixture was combined with chloroform (100 ml) and stirred, from which insoluble components were separated by filtration. Xylene and chloroform was distilled off from the filtrate under reduced pressure. The residue was purified by silica gel column chromatography (methylene chloride/hexane=1/5 to 1/1), washed with methanol, dried under reduced pressure, and thereby yielded Target Compound 6 (0.51 g, in a yield of 25%) as white crystals.

(ii) Synthesis of Target Compound 7

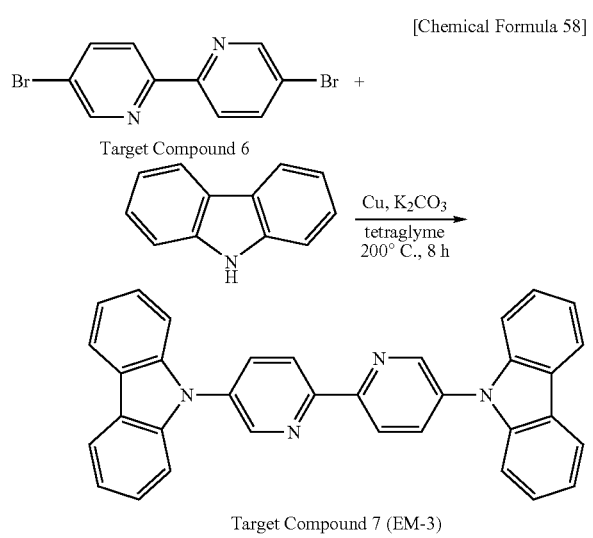

[Chemical Formula 58]

A mixture of Target Compound 6 (0.48 g), carbazole (1.02 g), copper powder (0.29 g), potassium carbonate (1.06 g), and Tetraglyme (4 ml) was stirred with heating at 200° C. in a nitrogen stream for eight hours, followed by standing to cool to room temperature. After the completion of reaction, the reaction mixture was combined with chloroform (200 ml), from which insoluble components were separated by filtration. Chloroform was distilled off from the filtrate under reduced pressure, and the residue was purified by silica gel column chromatography (n-hexane/methylene chloride=1/1). This was washed with ethyl acetate and with methanol, dried under reduced pressure, and thereby yielded Target Compound 6 (0.42 g, in a yield of 57%) as pale yellow crystals. The pale yellow crystals (0.42 g) were purified by sublimation to recover 0.22 g of a pale yellow solid.

This was identified as Target Compound 7 through DEI-MS (m/z=486 (M$^+$)).

This compound had a melting point of 323° C. and a gasification temperature of 443° C.

Synthesis Example 4

(i) Synthesis of Target Compound 8

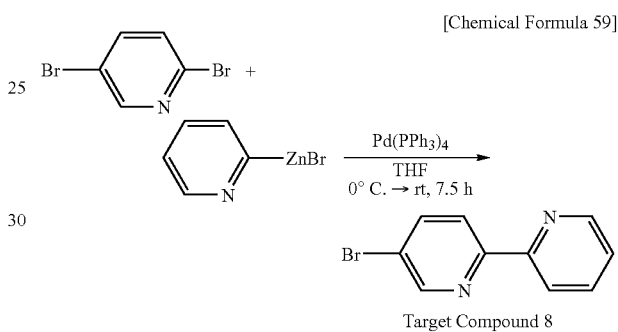

[Chemical Formula 59]

In a nitrogen stream, a mixture of 2,5-dibromopyridine (19.5 g), tetrakis(triphenylphosphine)palladium(0) (4.33 g), and tetrahydrofuran (THF) (75 ml) was cooled to 0° C., combined with a 0.5 M solution of 2-pyridylzinc bromide in THF (150 ml) added dropwise, warmed to room temperature, and stirred for 7.5 hours. The reaction mixture was combined with an aqueous solution of ethylenediamine tetraacetic acid (EDTA) (20 g) and sodium carbonate (20 g) in water (400 ml), followed by extraction with two portions of 300 ml of chloroform. The organic layer was dried over magnesium sulfate, concentrated, purified by column chromatography (methylene chloride/ethyl acetate=1/0 to 20/1), and thereby yielded Target Compound 8 (7.27 g, in a yield of 41%).

(ii) Synthesis of Target Compound 9

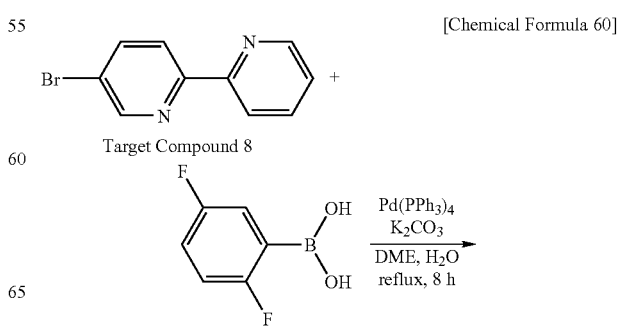

[Chemical Formula 60]

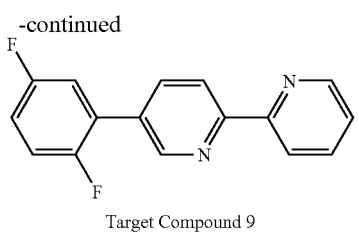

Target Compound 9

A mixture of Target Compound 8 (4-bromo-2,2'-bipyridyl) (2.40 g), 2,5-difluorophenylboronic acid (2.94 g), potassium carbonate (4.23 g), ethylene glycol dimethyl ether (20 ml), and water (10 ml) was stirred with heating at 60° C. in a nitrogen stream for fifteen minutes, combined with tetrakis (triphenylphosphine)palladium(0) (0.294 g), and stirred with heating under reflux for eight hours. After standing to cool to room temperature, the reaction mixture was combined with water (150 ml) to yield a precipitate. The precipitate was recovered by filtration, washed with a mixture of methanol/water, and dried under reduced pressure to yield crystals. The crystals were dissolved in toluene (150 ml) to yield a solution, and the solution was combined with activated clay, followed by stirring with heating under reflux for one hour. Insoluble components were separated by filtration, and the filtrate was concentrated to precipitate crystals. The crystals were washed with cold ethanol, dried under reduced pressure, and thereby yielded Target Compound 9 (0.79 g, in a yield of 29%) as white crystals.

(iii) Synthesis of Target Compound 10

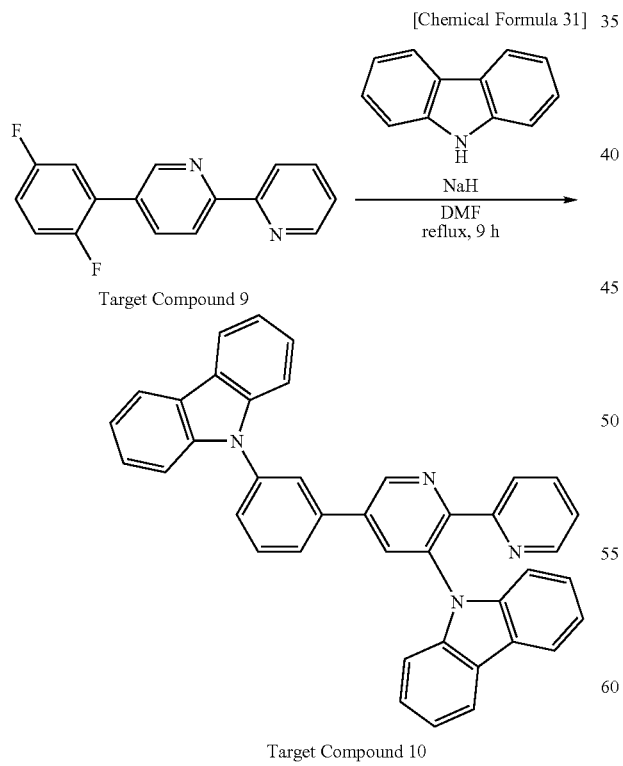

Target Compound 10

A suspension of sodium hydride (55%, 0.723 g) in anhydrous N,N-dimethylformamide (30 ml) was combined with carbazole (2.77 g), stirred with heating at 80° C. in a nitrogen stream for thirty minutes, and further combined with Target Compound 9 (4-(2,5-difluorophenyl)-2,2'-bipyridyl) (2.40 g), followed by stirring with heating under reflux for nine hours. This was combined with water (70 ml) and methanol (70 ml) under cooling with ice to yield a precipitate. The precipitate was separated by filtration, washed with methanol, and dried under reduced pressure to yield crystals. The crystals were purified by silica gel column chromatography (chloroform/acetone=1/0 to 20/1) further washed with ethanol, dried under reduced pressure, and thereby yielded Target Compound 5 (0.322 g, in a yield of 19%) as white crystals.

This was identified as Target Compound 10 through DEI-MS (m/z=562 (M$^+$)).

Synthesis Example 5

(i) Synthesis of Target Compound 11

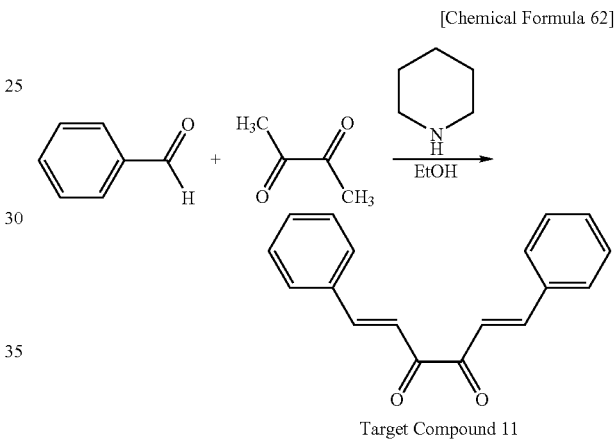

Target Compound 11

Benzaldehyde (10.6 g), diacetyl (4.3 g), and piperidine (0.5 ml) were dissolved in ethanol (50 ml) to yield a solution, and the solution was stirred with heating under reflux for 2.5 hours. After standing to cool, the mixture was cooled in a refrigerator to yield crystals. The crystals were collected by filtration, washed with methanol, dried, and thereby yielded Target Compound 11 (1.39 g).

(ii) Synthesis of Target Compound 12

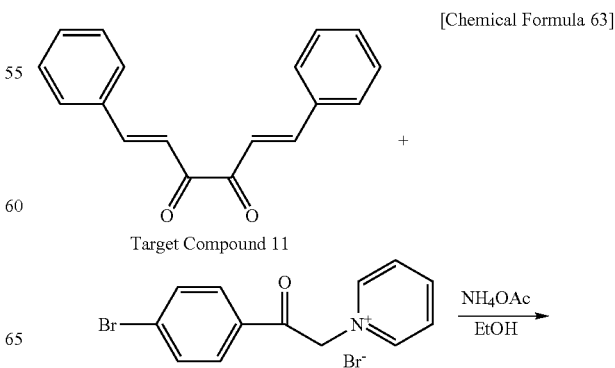

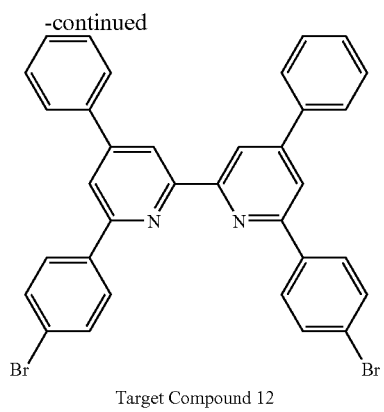

Target Compound 12

A mixture of 4-bromo-phenacylpyridinium bromide (3.56 g), Target Compound 11 (1.3 g), ammonium acetate (9.7 g), and ethanol (100 ml) was stirred with heating under reflux for four hours. After standing to cool, the crystals were separated by filtration, washed with methanol (100 ml), dried, and thereby yielded Target Compound 12 (0.98 g).

(iii) Synthesis of Target Compound 13

[Chemical Formula 64]

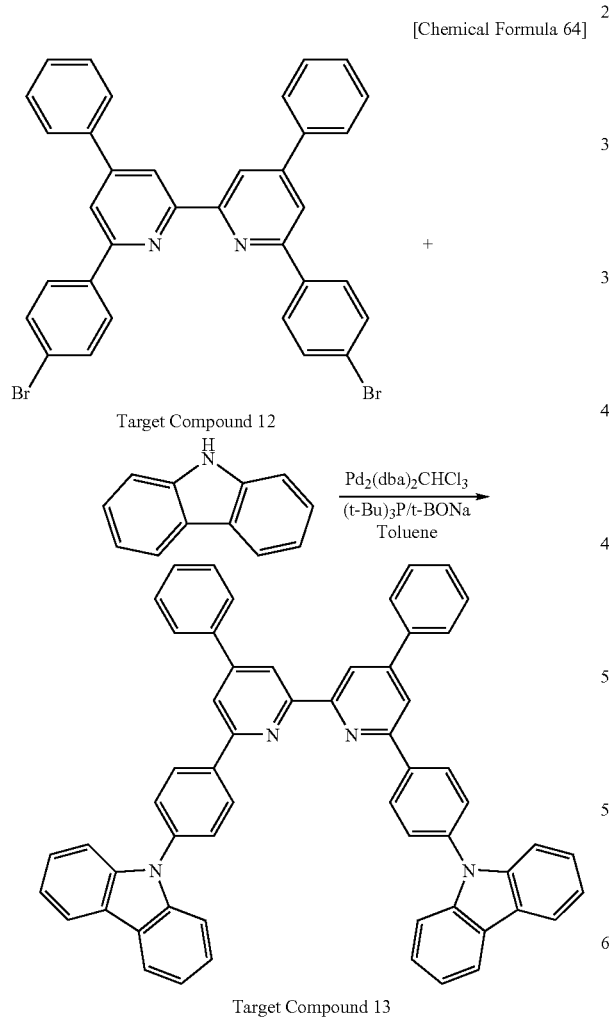

Target Compound 13

A mixture of Target Compound 12 (0.90 g), carbazole g), and sodium tert-butoxide (0.56 g) was combined with toluene (30 ml), followed by stirring to yield a mixture. Separately, tris(dibenzylideneacetone)dipalladium(0) chloroform (0.05 g) was dissolved in toluene (8 ml) and combined with tri-tert-butylphosphine (0.055 g) to yield a solution. The above-mentioned mixture was combined with the solution, followed by reaction with heating under reflux for four hours. After standing to cool, the crystals were collected by filtration, washed in a suspended state in methanol with heating, and further washed in a suspended state in a mixed solvent of methanol/water with heating. This was further purified by column chromatography and thereby yielded Target Compound 13 (0.65 g).

This was identified as Target Compound 13 through DEI-MS (m/z=791 (M$^+$)).

This compound had a melting point of 395° C., a gasification temperature of 555° C., and a glass transition temperature of 161° C.

Synthesis Example 6

(i) Synthesis of Target Compound 14

[Chemical Formula 65]

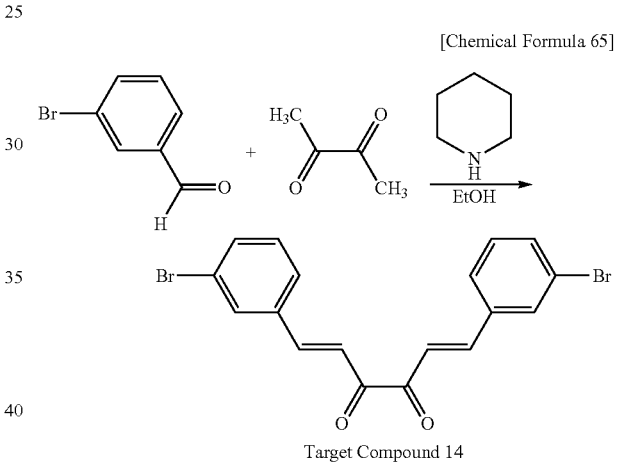

Target Compound 14

In ethanol (80 ml) were dissolved 3-bromobenzaldehyde (30.0 g), diacetyl (6.98 g), and piperidine (0.80 ml), followed by stirring with heating under reflux for 2.5 hours. After standing to cool, the mixture was cooled in a refrigerator to yield crystals. The crystals were collected by filtration, washed with methanol, dried, and thereby yielded Target Compound 14 (2.33 g).

(ii) Synthesis of Target Compound 15

[Chemical Formula 66]

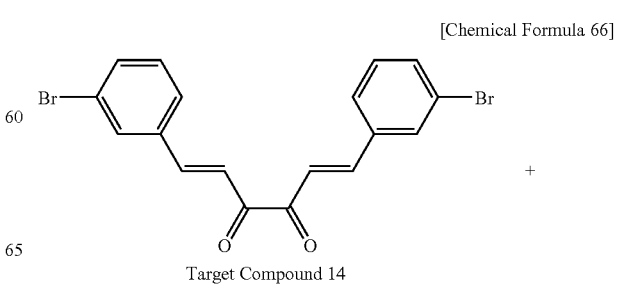

Target Compound 14

-continued

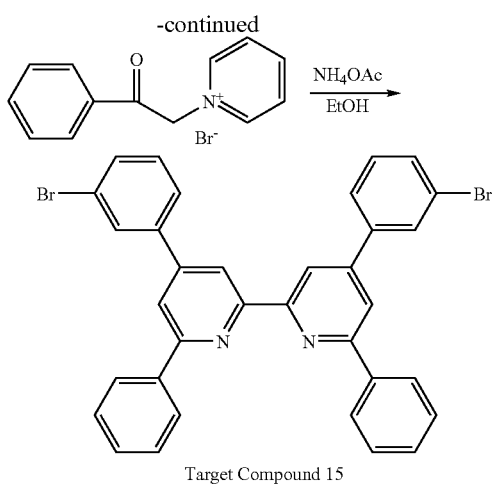

Target Compound 15

A mixture of phenacylpyridinium bromide (2.56 g), Target Compound 14 (2.00 g), ammonium acetate (9.30 g), and ethanol (100 ml) was stirred with heating under reflux for eight hours. After standing to cool, the crystals were collected by filtration, washed with methanol (100 ml), dried, and thereby yielded Target Compound 15 (1.30 g).

(iii) Synthesis of Target Compound 16

[Chemical Formula 67]

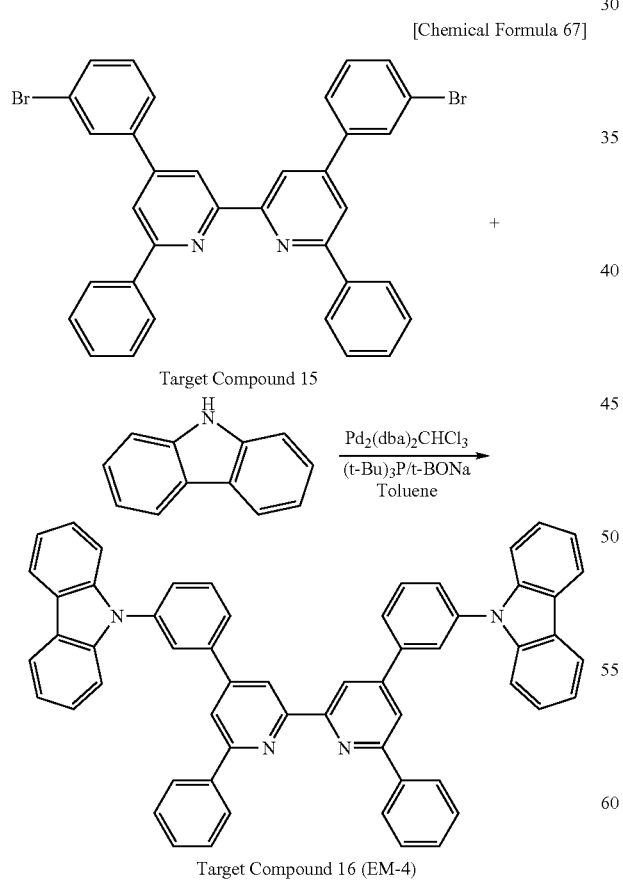

Target Compound 16 (EM-4)

A mixture of Target Compound 15 (1.2 g), carbazole g), and sodium tert-butoxide (0.74 g) was combined with toluene (40 ml), followed by stirring to yield a mixture. Separately, tris(dibenzylideneacetone)dipalladium(0) chloroform (0.066 g) was dissolved in toluene (8 ml) and combined with tri(tert-butyl)phosphine (0.051 g) to yield a solution. The solution was combined with the above-mentioned mixture, followed by stirring with heating under reflux for seven hours. After standing to cool, the crystals were collected by filtration, washed in a suspended state in methanol with heating, further washed in a suspended state in chloroform with heating several times, purified by sublimation, and thereby yielded Target Compound 16 (0.91 g).

This was identified as Target Compound 16 through DEI-MS (m/z=791 ($M^+$)).

This compound had a melting point of 316° C., a gasification temperature of 346° C., and a glass transition temperature of 140° C.

Synthesis Example 7

(i) Synthesis of Target Compound 17

[Chemical Formula 68]

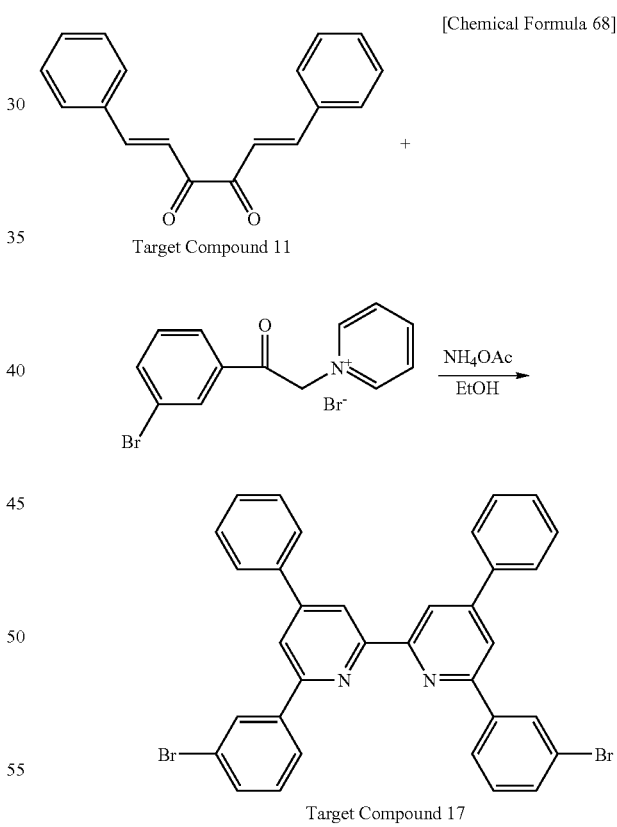

Target Compound 17

A mixture of 3-bromophenacylpyridinium bromide (8.23 g), Target Compound 11 (3.00 g) prepared according to Synthesis Example 5, ammonium acetate (22.5 g), and ethanol (200 ml) was stirred with heating under reflux for eight hours. After standing to cool, the crystals were collected by filtration, washed in a suspended state in methanol with heating, dried, and thereby yielded Target Compound 17 (1.05 g).

(ii) Synthesis of Target Compound 18

[Chemical Formula 69]

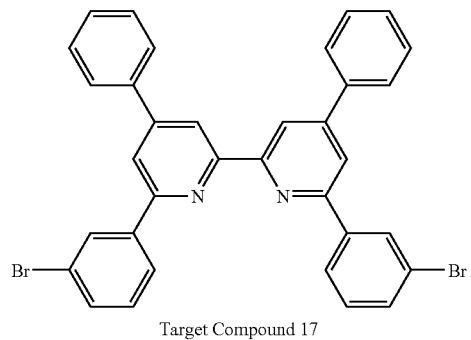

Target Compound 17

+

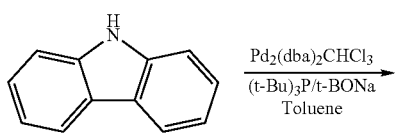

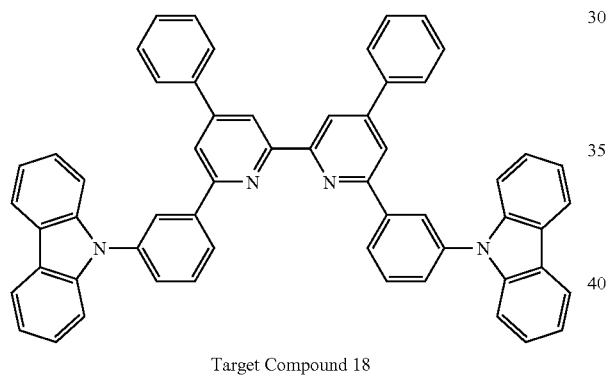

Target Compound 18

A mixture of Target Compound 17 (1.4 g), carbazole (0.94 g), and sodium tert-butoxide (0.86 g) was combined with toluene (70 ml), followed by stirring to yield a mixture. Separately, tris(dibenzylideneacetone)dipalladium(0) chloroform (0.087 g) was dissolved in toluene (8 ml) and combined with tri(tert-butyl)phosphine (0.068 g) to yield a solution. The solution was combined with the above-mentioned mixture, followed by stirring with heating under reflux for seven hours. After standing to cool, the crystals were collected by filtration, washed in a suspended state in methanol with heating, further washed in a suspended state in chloroform with heating several times, purified by sublimation, and thereby yielded Target Compound 18 (0.70 g).

This was identified as Target Compound 18 though DEI-MS (m/z=791 (M$^+$)).

This compound had a melting point of 317° C., a gasification temperature of 540° C., and a glass transition temperature of 139° C.

Synthesis Example 8

(i) Synthesis of Target Compound 19

[Chemical Formula 70]

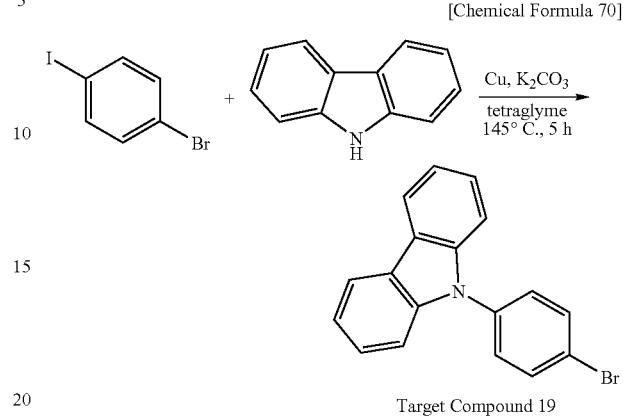

Target Compound 19

A mixture of carbazole (6.82 g), 4-bromoiodobenzene (15.0 g), copper powder (2.61 g), potassium carbonate (11.3 g), and Tetraglyme (30 ml) was stirred with heating at 145° C. in a nitrogen stream for five hours, followed by standing to cool to room temperature. The reaction mixture was combined with chloroform, from which insoluble components were separated by filtration. Chloroform was then distilled off from the filtrate under reduced pressure, and the residue was purified by silica gel column chromatography (n-hexane/toluene=4/1), dried under reduced pressure, and thereby yielded Target Compound 19 (9.08 g, in a yield of 69%) as white crystals.

(ii) Synthesis of Target Compound 20

[Chemical Formula 71]

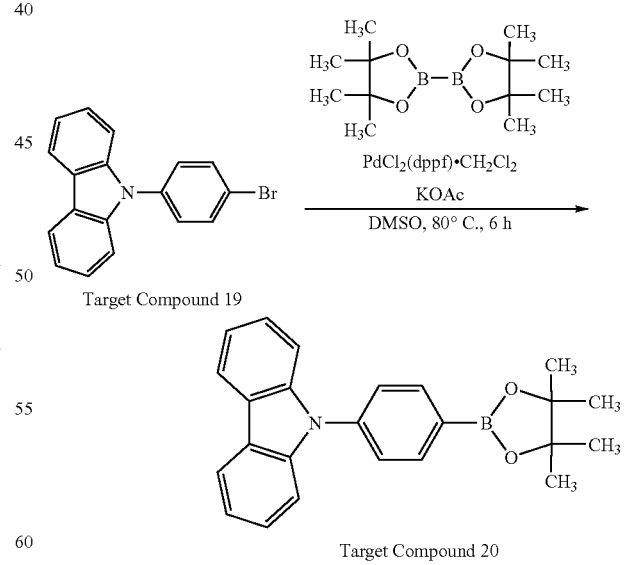

Target Compound 20

A mixture of Target Compound 19 (4.50 g), bis(pinacolatodiboron) (4.61 g), potassium acetate (4.61 g), and DMSO (75 ml) was stirred with heating at 60° C. in a nitrogen stream for fifteen minutes, and combined with [1,1'-bis(diphenylphosphino)ferrocene]dichloropalladium(II) dichloromethane complex (0.343 g), followed by stirring with heating at 80° C. for six hours. After standing to cool to room temperature, the reaction mixture was combined with water (250 ml) and toluene (500 ml), followed by stirring. The aqueous layer was reextracted twice with toluene, organic layers were combined, and magnesium sulfate and activated clay were added. Magnesium sulfate and activated clay were then separated by filtration, and toluene was distilled off under reduced pressure to precipitate crystals. The crystals were washed with cold methanol, dried under reduced pressure, and thereby yielded Target Compound 20 (4.46 g, in a yield of 86%) as white crystals.

(iii) Synthesis of Target Compound 21

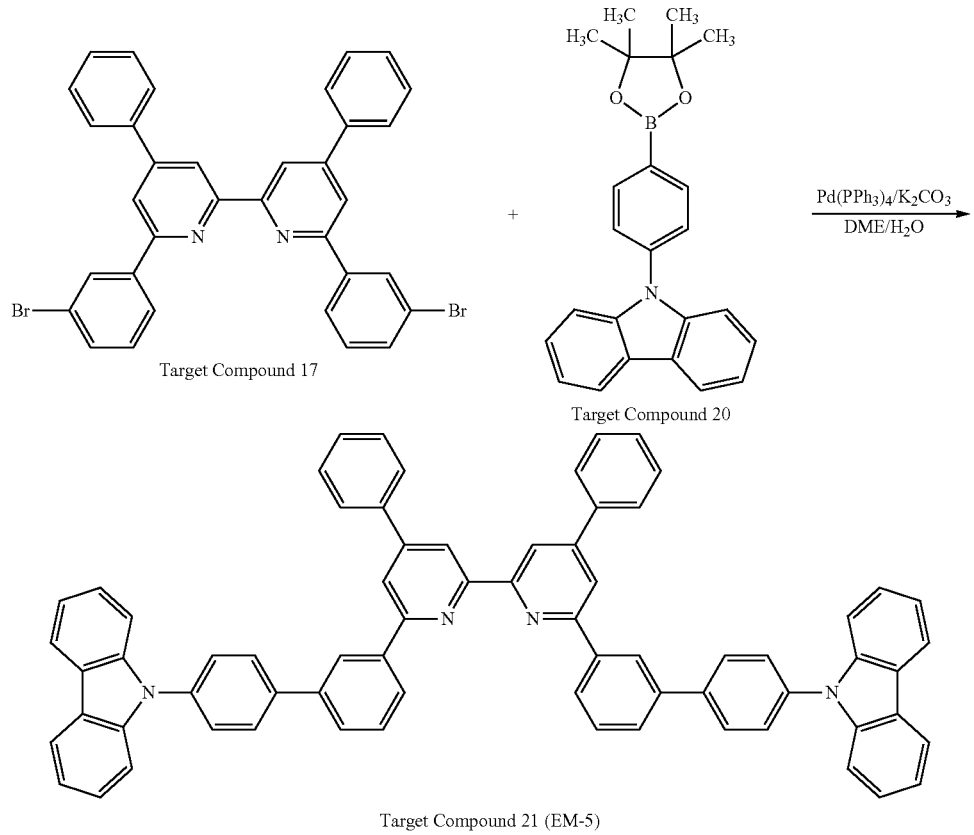

Target Compound 21 (EM-5)

A mixture of Target Compound 17 (1.20 g) prepared according to Synthesis Example 7, Target Compound 20 (1.64 g), and potassium carbonate (1.07 g) was combined with ethylene glycol dimethyl ether (80 ml) and water (16 ml), followed by stirring. This was combined with tetrakis(triphenylphosphine)palladium(0) (0.11 g), followed by stirring with heating under reflux for six hours. After standing to cool, the mixture was concentrated and combined with methanol to yield a precipitate. The precipitate was washed with different solvents, purified by column chromatography, and thereby yielded Target Compound 21 (1.40 g).

This was identified as Target Compound 21 through DEI-MS (m/z=942 (M$^+$)).

This compound had a melting point of 369° C., a gasification temperature of 574° C. and a glass transition temperature of 155° C.

Synthesis Example 9

(i) Synthesis of Target Compound 22

[Chemical Formula 73]

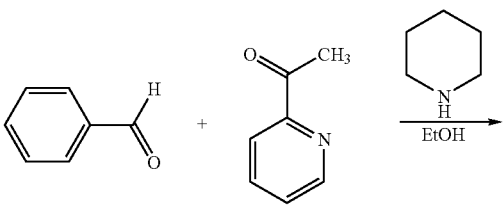

[Chemical Formula 72]

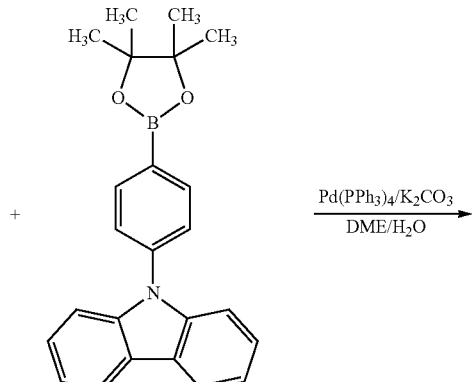

-continued

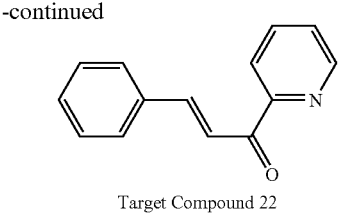

Target Compound 22

A mixture of 2-acetylpyridine (9.80 g), benzaldehyde (8.57 g), and piperidine (0.5 ml) was dissolved in ethanol (20 ml), followed by stirring with heating under reflux for eight hours. After standing to cool, the solvent was distilled off under reduced pressure, to thereby yield Target Compound 22 (17.0 g) as a liquid.

(ii) Synthesis of Target Compound 23

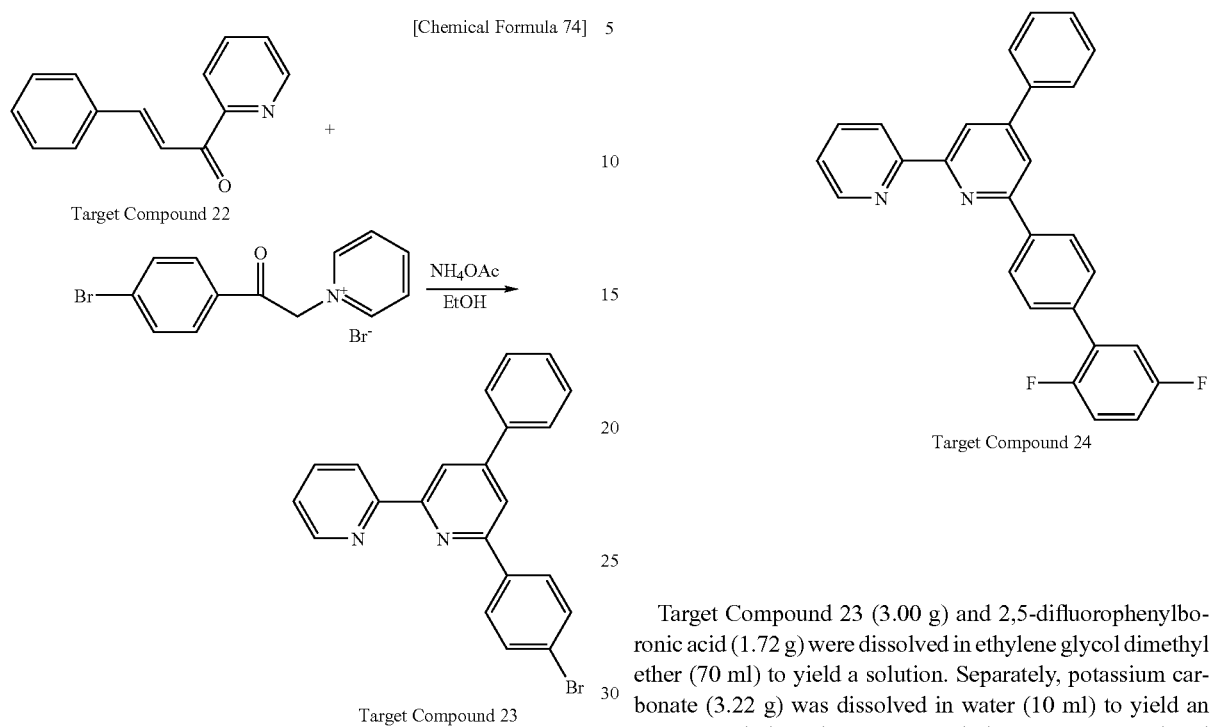

[Chemical Formula 74]

A mixture of 4-bromophenacylpyridinium bromide (7.14 g), Target Compound 22 (8.36 g), ammonium acetate (39.0 g), and ethanol (200 ml) was stirred with heating under reflux for eight hours to yield a solution. The solution was combined with methanol (50 ml), followed by stirring to yield a precipitate. The precipitate was filtrated to yield crystals. The crystals were washed with methanol (200 ml), collected by filtration, dried and thereby yielded Target Compound 23 (3.35 g).

(iii) Synthesis of Target Compound 24

[Chemical Formula 75]

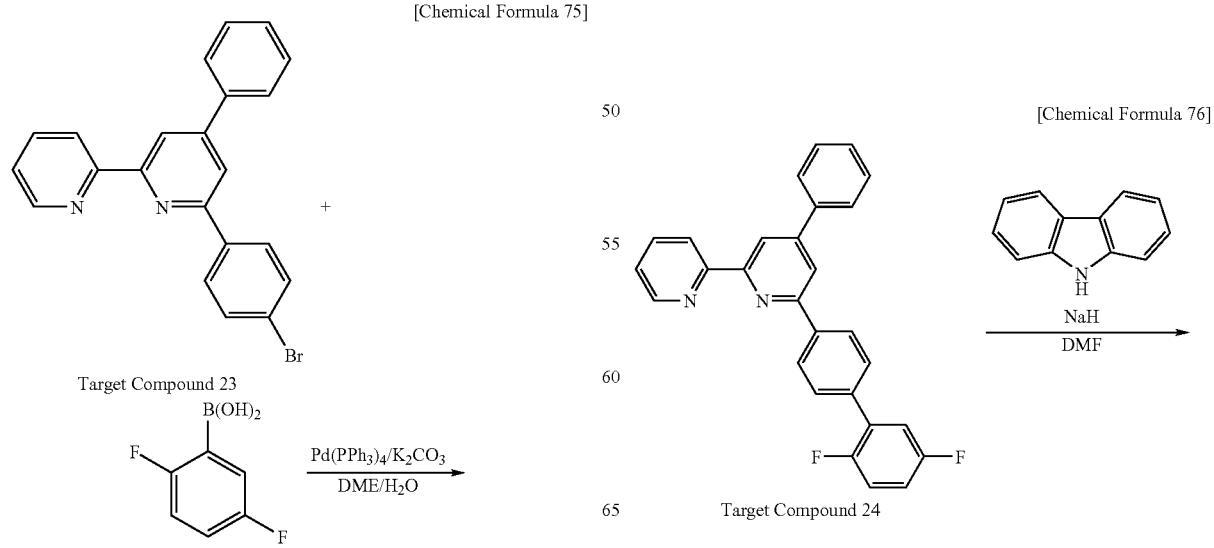

Target Compound 23 (3.00 g) and 2,5-difluorophenylboronic acid (1.72 g) were dissolved in ethylene glycol dimethyl ether (70 ml) to yield a solution. Separately, potassium carbonate (3.22 g) was dissolved in water (10 ml) to yield an aqueous solution, the aqueous solution was evacuated and added to the system. The entire system was evacuated, replaced with nitrogen atmosphere, and stirred with heating. This was combined with tetrakis(triphenylphosphine)palladium(0) (0.36 g) at an inner temperature of 60° C., followed by stirring with heating under reflux for four hours. After standing to cool, the mixture was concentrated, washed in a suspended state in methanol, recrystallized from methanol, dried, and thereby yielded Target Compound 24 (2.42 g).

(iv) Synthesis of Target Compound 25

[Chemical Formula 76]

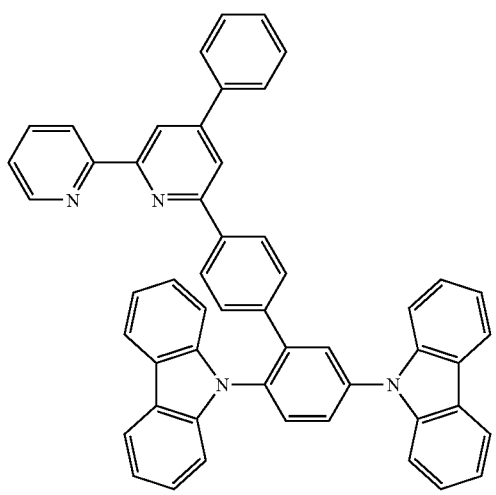

Target Compound 25 (EM-6)

Sodium hydride (55%, 0.62 g) was suspended with stirring in anhydrous dimethylformamide (50 ml), and carbazole (2.38 g) was added in small portions to the system. After completion of the addition, the system was raised in temperature to 80° C. and combined with Target Compound 24 (1.5 g), followed by stirring with heating under reflux for twelve hours. After standing to cool, the mixture was poured into methanol (200 ml) and water (40 ml) to yield crystals. The crystals were collected by filtration, washed in a suspended state in methanol with heating, recrystallized from methylene chloride/methanol, purified by column chromatography, and thereby yielded Target Compound 25 (0.81 g).

This was identified as Target Compound 25 through DEI-MS (m/z=714 (M$^+$)).

This compound had a melting point of 282° C., a gasification temperature of 508° C., and a glass transition temperature of 152° C.

[Preparation Examples of Organic Electroluminescent Devices]

Preparation examples of organic electroluminescent devices according to the present invention will be illustrated below.

Part of the prepared organic electroluminescent devices were subjected to the following driving lifetime tests.

<Driving Lifetime Test>
Temperature: room temperature
Driving method: direct-current driving (DC driving)
Initial luminance: 2,500 cd/m$^2$ In the tests, each device was allowed to continuously emit light by supplying a constant current, and a luminance and a voltage increase after 1,000 hours from the beginning of driving were determined to compare. The ratio ($L_{1,000}/L_0$) of the luminance ($L_{1,000}$) after 1,000 hour-driving to the initial luminance ($L_0$), and the increase in voltage ($\Delta V=V_{1,000}-V_0$) from the initial voltage ($V_0$) to the voltage ($V_{1,000}$) after 1,000 hour-driving were determined, respectively.

Example 1

An organic electroluminescent device having the structure shown in FIG. 3 was prepared in the following manner.

An indium-tin oxide (ITO) transparent electroconductive film deposited to a thickness of 150 nm on a glass substrate 1 (sputtered film; sheet resistance: 15Ω) was patterned in a 2-mm width stripe pattern using a common photolithography technique and etching with hydrochloric acid, thereby forming an anode 2. The thus patterned ITO substrate was washed by applying ultrasonic waves in acetone, washed with pure water, then washed by applying ultrasonic waves in isopropyl alcohol, followed by drying using a nitrogen blow and washing by applying UV rays and ozone.

As a material for a hole injection layer 3, a non-conjugated polymeric compound (PB-1, having a weight-average molecular weight of 29400 and a number-average molecular weight of 12600) having an aromatic amino group of the following structural formula was applied by spin coating together with an electron acceptor (A-2) having the following structural formula under the following conditions.

[Chemical Formula 77]

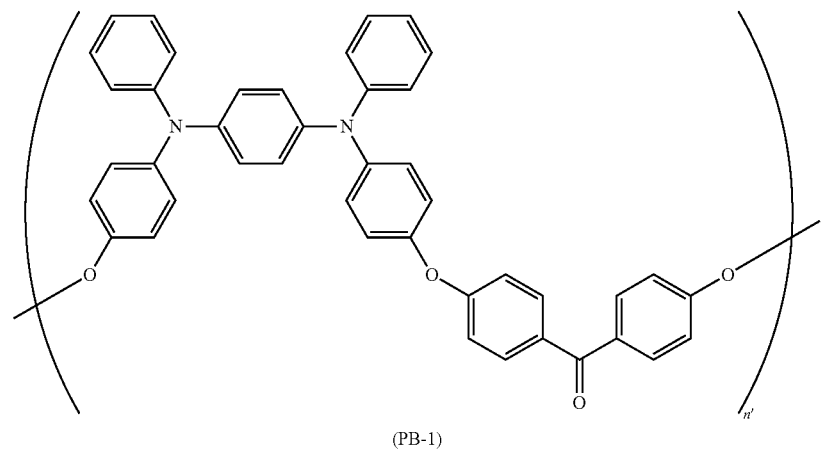

(PB-1)

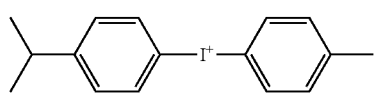

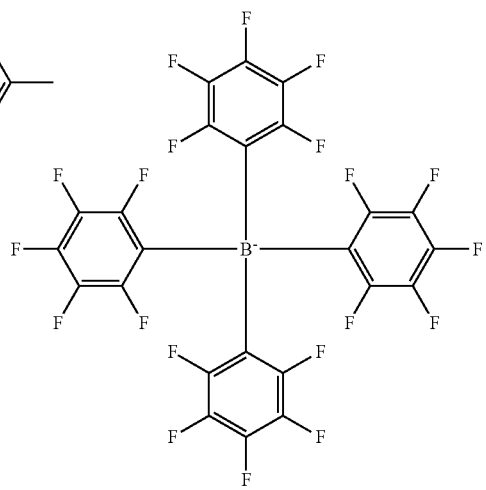

(A-2)

Condition of Spin Coating
Solvent: ethyl benzoate;
Concentration of coating composition: 2 percent by weight;
Ratio of PB-1 to A-2: 10:2 (by weight);
Revolution number of spinner: 1500 [rpm];
Rotation time of spinner: 30 [sec.]; and
Drying condition: 230 [° C.] for 15 [min.]

The spin coating yielded a uniform thin film 30 nm thick.

Next, the substrate bearing the formed hole injection layer 3 was placed in a vacuum deposition chamber. After roughly evacuating the chamber using an oil rotary pump, the inside of the chamber was evacuated to a vacuum degree of $5.2 \times 10^{-5}$ Pa (about $3.9 \times 10^{-7}$ Torr) or less by using a cryogenic pump. An arylamine compound (H-1) shown below was placed in a ceramic crucible placed within the chamber and was heated through a tantalum wire heater disposed around the crucible to conduct vacuum deposition. The temperature of the crucible in this procedure was controlled within the range of from 258° C. to 271° C. The vacuum deposition was conducted at a vacuum degree of $5.8 \times 10^{-5}$ Pa (about $4.4 \times 10^{-7}$ Torr) and a vacuum deposition rate of 0.18 nm per second and thereby yielded a hole transport layer 4 having a thickness of 40 nm.

[Chemical Formula 79]

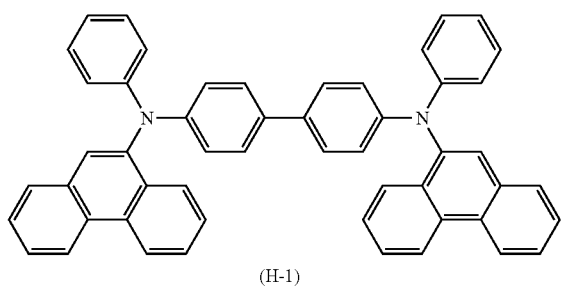

(H-1)

Subsequently, Target Compound 3 (following EM-1) prepared according to Synthesis Example 1 as a major component (host material) and an organic iridium complex (D-1) as a minor component (dopant) of a light-emitting layer 5 were placed in different ceramic crucibles, and film formation was carried out by binary vacuum deposition.

[Chemical Formula 80]

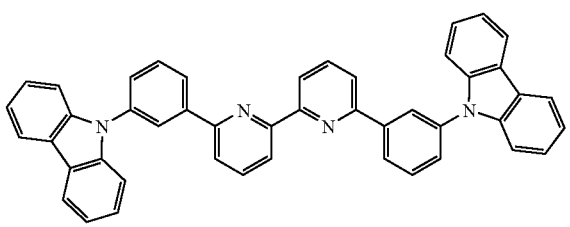

(EM-1)

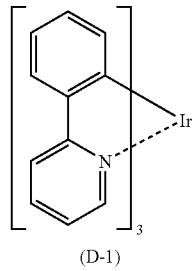

(D-1)

The crucible temperature and the vacuum deposition rate for Target Compound 3 (EM-1) were controlled to be 307° C. to 309° C., and 0.10 nm per second, respectively, and the crucible temperature for the compound (D-1) was controlled to be 244° C. to 245° C. Thus, a light-emitting layer 5 having a thickness of 30 nm and containing about 6 percent by weight of the compound (D-1) was stacked on the hole transport layer 4. The degree of vacuum upon vacuum deposition was $5.5 \times 10^{-5}$ Pa (about $4.1 \times 10^{-7}$ Torr).

Further, the following pyridine derivative (HB-1) was stacked as a hole blocking layer 6 in a thickness of 5 nm at a crucible temperature of 213° C. to 216° C. at a vacuum deposition rate of 0.08 nm per second. The degree of vacuum upon vacuum deposition was $4.9 \times 10^{-5}$ Pa (about $3.7 \times 10^{-7}$ Torr).

[Chemical Formula 81]

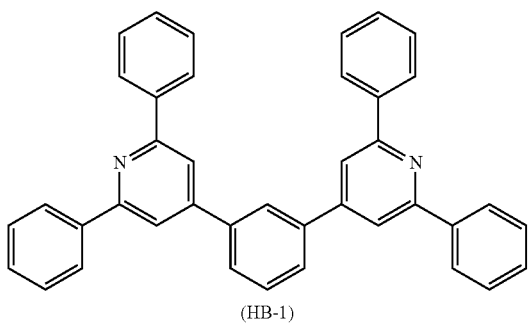

(HB-1)

On the hole blocking layer 6 was deposited, as an electron transport layer 7, the following aluminum 8-hydroxyquinoline complex (ET-1) in the same manner. The temperature of the crucible for the aluminum 8-hydroxyquinoline complex in this procedure was controlled within the range of from 250° C. to 260° C. The vacuum deposition was carried out at a degree of vacuum of $5.0\times10^{-5}$ Pa (about $3.8\times10^{-7}$ Torr) and a vacuum deposition rate of 0.21 nm per second to yield a film 30 nm thick.

[Chemical Formula 82]

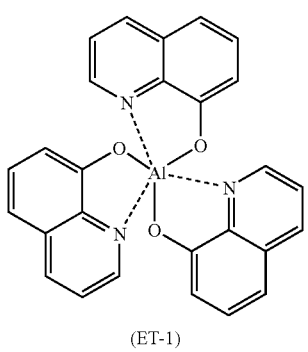

(ET-1)

The temperature of the substrate upon vacuum deposition of the hole injection layer 3, the hole transport layer 4, the light-emitting layer 5, the hole blocking layer 6, and the electron transport layer 7 was kept to room temperature.

The device which had been subjected to vacuum deposition up to the electron transport layer 6 was once taken out of the vacuum deposition chamber into the atmosphere. A 2-mm width striped shadow mask as a mask for vacuum deposition of a cathode was brought in close contact with the device perpendicularly to the ITO stripe of the anode 2, and the device was placed in a different vacuum deposition chamber. The chamber was evacuated to a degree of vacuum of $2.0\times10^{-6}$ Torr (about $2.7\times10^{-4}$ Pa) or less in the same manner as with the organic layers. As a cathode 8, initially, a film of lithium fluoride (LiF) was deposited to a thickness of 0.5 nm on the electron transport layer 7 at a vacuum deposition rate of 0.03 nm per second and a degree of vacuum of $2.8\times10^{-6}$ Torr (about $3.7\times10^{-4}$ Pa) using a molybdenum boat. Next, aluminum was heated in the same manner using a molybdenum boat and was deposited at a vacuum deposition rate of 0.46 nm per second and a degree of vacuum of $9.6\times10^{-6}$ Torr (about $1.3\times10^{-3}$ Pa) to yield an aluminum layer 80 nm thick. Thus, the cathode 8 was completed. The temperature of the substrate upon vacuum deposition of the two-layered cathode 8 was kept to room temperature.

Thus, an organic electroluminescent device having a light-emitting area of 2 mm wide and 2 mm long was obtained.

The light emitting properties and lifetime properties of the device are shown in Table 1.

The maximal wavelength in emission spectrum of the device was 512 nm with chromaticity in terms of CIE (x, y) of (0.30, 0.60), which was identified to be from the organic iridium complex (D-1).

This device had a higher luminous efficiency and a longer lifetime than those of the after-mentioned devices according to Comparative Examples.

Example 2

A device was prepared by the procedure of Example 1, except for not forming a layer of the pyridine derivative (HB-1) as a hole blocking layer.

The light emitting properties and lifetime properties of the device are shown in Table 1.

The maximal wavelength in emission spectrum of the device was 512 nm with chromaticity in terms of CIE (x, y) of (0.29, 0.60), which was identified to be from the organic iridium complex (D-1).

The device emitted light from the organic iridium complex with a high efficiency, even though having no hole blocking layer.

Example 3

A device was prepared by the procedure of Example 1, except for using following Target Compound 5 (following EM-2) as a major component (host material) of the light-emitting layer 5 instead of Target Compound 3 (EM-1).

The light emitting properties of the device are shown in Table 1.

The maximal wavelength in emission spectrum of the device was 514 nm with chromaticity in terms of CIE (x, y) of (0.30, 0.61), which was identified to be from the organic iridium complex (D-1).

The device emitted light from the organic iridium complex with a high efficiency and was driven at a low drive voltage.

[Chemical Formula 83]

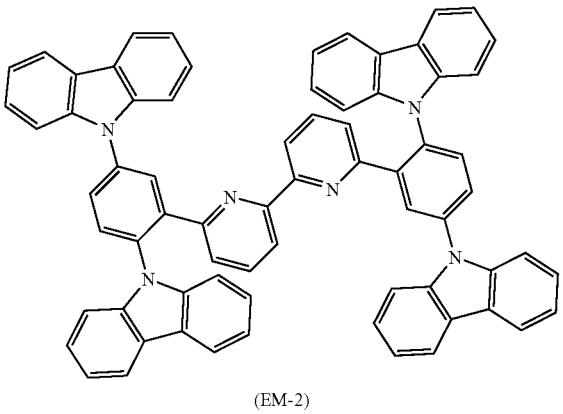

(EM-2)

Example 4

A device was prepared by the procedure of Example 3, except for not forming a layer of the pyridine derivative (HB-1) as a hole blocking layer.

The light emitting properties of the device are shown in Table 1.

The maximal wavelength in emission spectrum of the device was 514 nm with chromaticity in terms of CIE (x, y) of (0.30, 0.61), which was identified to be from the organic iridium complex (D-1).

The device emitted light from the organic iridium complex with a high efficiency and was driven at a low drive voltage, even though having no hole blocking layer.

Example 5

A device was prepared by the procedure of Example 1, except for using following Target Compound 7 (following EM-3) as a major component (host material) of the light-emitting layer 5 instead of Target Compound 3 (EM-1).

The light emitting properties of the device are shown in Table 1.

The maximal wavelength in emission spectrum of the device was 513 nm with chromaticity in terms of CIE (x, y) of (0.30, 0.61), which was identified to be from the organic iridium complex (D-1).

[Chemical Formula 84]

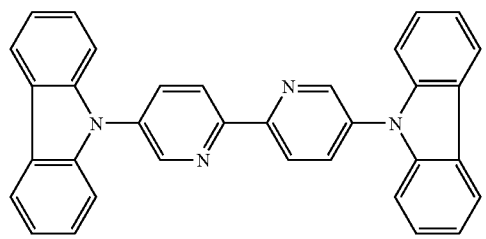

(EM-3)

Example 6

A device was prepared by the procedure of Example 5, except for not forming a layer of the pyridine derivative (HB-1) as a hole blocking layer.

The light emitting properties of the device are shown in Table 1.

The maximal wavelength in emission spectrum of the device was 513 nm with chromaticity in terms of CIE (x, y) of (0.30, 0.61), which was identified to be from the organic iridium complex (D-1).

The device emitted light from the organic iridium complex with a high efficiency, even though having no hole blocking layer, and was driven at a lower drive voltage than those of the devices according to Comparative Examples 1 and

Example 7

A device was prepared by the procedure of Example 2, except for using following Target Compound 16 (EM-4) as a major component (host material) of the light-emitting layer 5 instead of Target Compound 3 (EM-1).

The light emitting properties of the device are shown in Table 1.

The maximal wavelength in emission spectrum of the device was 513 nm with chromaticity in terms of CIE (x, y) of (0.30, 0.61), which was identified to be from the organic iridium complex (D-1).

The device emitted light from the organic iridium complex with a high efficiency, even though having no hole blocking layer, and was driven at a lower voltage than that of the device according to Comparative Example 2.

[Chemical Formula 85]

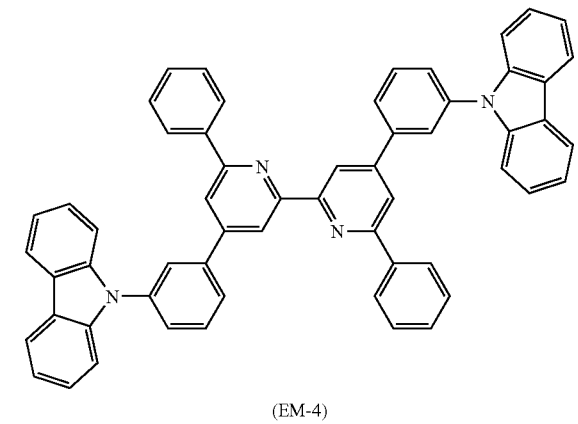

(EM-4)

Example 8

A device was prepared by the procedure of Example 2, except for using following Target Compound 21 (EM-5) as a major component (host material) of the light-emitting layer 5 instead of Target Compound 3 (EM-1).

The light emitting properties of the device are shown in Table 1.

The maximal wavelength in emission spectrum of the device was 513 nm with chromaticity in terms of CIE (x, y) of (0.30, 0.61), which was identified to be from the organic iridium complex (D-1).

The device emitted light from the organic iridium complex with a high efficiency, even though having no hole blocking layer, and was driven at a lower voltage than that of the device according to Comparative Example 2.

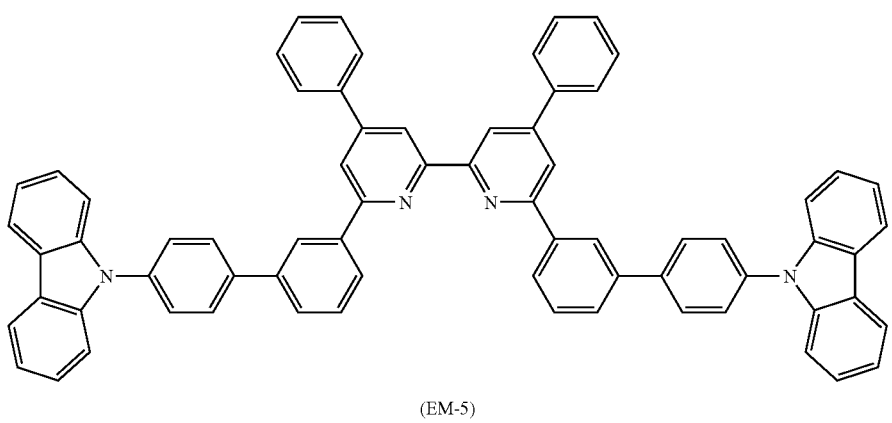

(EM-5)

Example 9

A device was prepared by the procedure of Example 1, except for using following Target Compound 25 (EM-6) as a major component (host material) of the light-emitting layer 5 instead of Target Compound 3 (EM-1).

The light emitting properties of the device are shown in Table 1.

The maximal wavelength in emission spectrum of the device was 514 nm with chromaticity in terms of CIE (x, y) of (0.31, 0.61), which was identified to be from the organic iridium complex (D-1).

The device emitted light from the organic iridium complex with a high efficiency and was driven at a lower voltage than that of the device according to Comparative Example 1.

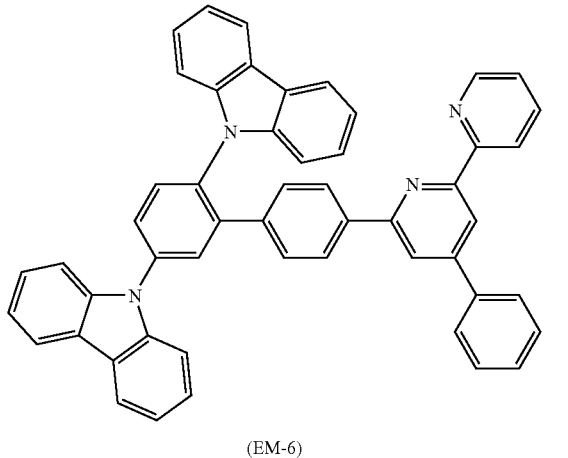

(EM-6)

Example 10

A device was prepared by the procedure of Example 9, except for not forming a layer of the pyridine derivative (HB-1) as a hole blocking layer.

The light emitting properties of the device are shown in Table 1.

The maximal wavelength in emission spectrum of the device was 515 nm with chromaticity in terms of CIE (x, y) of (0.31, 0.62), which was identified to be from the organic iridium complex (D-1).

The device emitted light from the organic iridium complex with a high efficiency, even though having no hole blocking layer, and was driven at a lower voltage than that of the device according to Comparative Example 2.

Comparative Example 1

A device was prepared by the procedure of Example 1, except for using the following compound (CBP) as a major component (host material) of the light-emitting layer 5 instead of Target Compound (EM-1).

The light emitting properties and lifetime properties of the device are shown in Table 1.

The maximal wavelength in emission spectrum of the device was 514 nm with chromaticity in terms of CIE (x, y) of (0.30, 0.58), which was identified to be from the organic iridium complex (D-1).

This device had a lower luminous efficiency than those of the devices according to Examples 1 to 6.

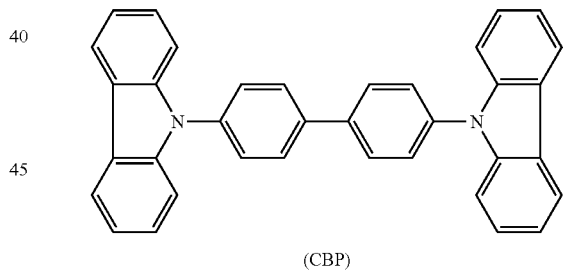

(CBP)

Comparative Example 2

A device was prepared by the procedure of Comparative Example 1, except for not forming a layer of the pyridine derivative (HB-1) as a hole blocking layer.

The light emitting properties of the device are shown in Table 1.

The maximal wavelength in emission spectrum of the device was 512 nm with chromaticity in terms of CIE (x, y) of (0.30, 0.60), which was identified to be from the organic iridium complex (D-1).

This device emitted light from the organic iridium complex, even though having no hole blocking layer, but had a lower luminous efficiency than those of the devices according to Examples 1 to 6. In addition, it was driven at a higher drive voltage than those of the devices according to Examples 1 and 2.

TABLE 1

| | Component of device | | Properties of device | | | | |
|---|---|---|---|---|---|---|---|
| | Host material | Hole | Luminance/current density | Voltage | Luminous efficiency | Lifetime properties | |
| | of light-emitting layer | blocking material | [cd/A] (@2.5 mA/cm²) | [V] (@2.5 mA/cm²) | [lm/W] (@2.5 mA/m²) | Luminance ($L_{1,000}/L_0$) | Increase in voltage ($\Delta V$) |
| Example 1 | EM-1 | HB-1 | 30.5 | 6.7 | 14.3 | 0.63 | 1.1 |
| Example 2 | EM-1 | — | 28.5 | 6.3 | 14.2 | 0.57 | 0.9 |
| Example 3 | EM-2 | HB-1 | 24.6 | 5.1 | 15.2 | | |
| Example 4 | EM-2 | — | 21.4 | 5.1 | 13.2 | | |
| Example 5 | EM-3 | HB-1 | 28.3 | 5.1 | 17.4 | | |
| Example 6 | EM-3 | — | 25.5 | 4.6 | 17.4 | | |
| Example 7 | EM-4 | — | 17.4 | 6.3 | 8.8 | | |
| Example 8 | EM-5 | — | 17.9 | 5.2 | 10.9 | | |
| Example 9 | EM-6 | HB-1 | 33.1 | 6.1 | 17.1 | | |
| Example 10 | EM-6 | — | 32.3 | 5.3 | 19.4 | | |
| Com. Ex. 1 | CBP | HB-1 | 25.3 | 6.2 | 12.8 | 0.53 | 1.7 |
| Com. Ex. 2 | CBP | — | 16.6 | 7.3 | 7.1 | | |

As is described above, the devices according to Examples 1 to 4 have higher luminous efficiencies than those of the devices according to Comparative Examples 1 and 2. Among them, the devices according to Examples 1 and 2 emit light with a higher luminance and show a smaller increase in voltage than those of the device according to Comparative Example 1. These results demonstrate that phosphorescent devices capable of emitting light with a high efficiency, being highly stably driven and having a long lifetime can be provided by using organic compounds according to the present invention.

While the present invention has been shown and described in detail with reference to specific embodiments thereof, it will be understood by those skilled in the art that various changes and modifications may be made without departing from the spirit and scope of the present invention.

The present invention is based on Japanese Patent Application No. 2005-17098 filed on Jan. 25, 2005, the entire contents of which being incorporated herein by reference.

The invention claimed is:

1. A compound of Formula (I):

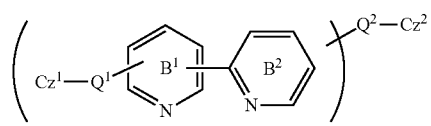

(I)

wherein
Cz¹ and Cz² may be the same as or different from each other and each represent a carbazolyl group;
Q¹ and Q² may be the same as or different from each other and each represent a direct bond or an arbitrary linkage group;
Cz¹, Cz², Q¹, Q², Ring B¹ and Ring B² may optionally each be substituted, wherein Formula (I) is represented by following Formula (I-1):

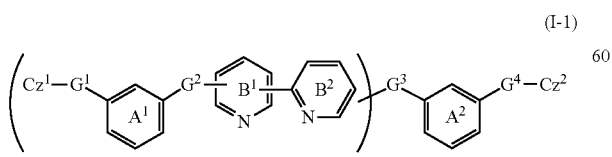

(I-1)

wherein G¹, G², G³, and G⁴ may be the same as or different from each other and each represent a direct bond or an arbitrary linkage group;

ring A¹ and Ring A² each represent a benzene ring which may be substituted; and
Cz¹, CZ², Ring B¹ and Ring B² are as defined in Formula (I).

2. The organic compound according to claim 1, wherein the partial structure of Formula (I) represented by following Formula (I') is represented by following Formula (III-1):

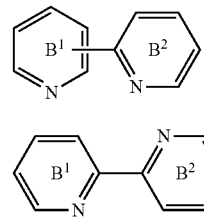

(I')

(III-1)

wherein Ring B¹ and Ring B² are as defined in Formula (I).

3. The organic compound according to claim 1, wherein all the carbazolyl groups in the molecule are N-carbazolyl groups represented by following Formula (II):

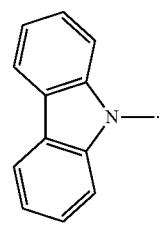

(II)

4. The organic compound according to claim 1, wherein within Formula (I), the partial structure represented by Formula (I') is a structure of Formula (III-2):

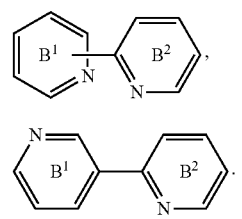

(I')

(III-2)

5. The organic compound according to claim 1, wherein within Formula (I), the partial structure represented by Formula (I') is a structure of Formula (III-3):

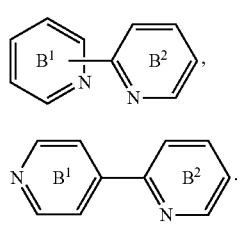

6. The organic compound according to claim 1, which is represented by the following structural formula:

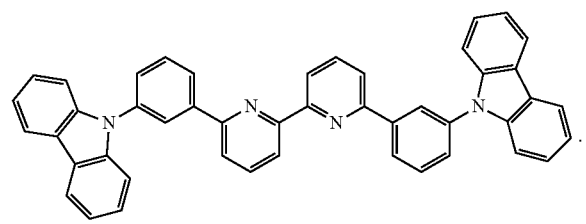

7. The organic compound according to claim 1, which is represented by the following structural formula:

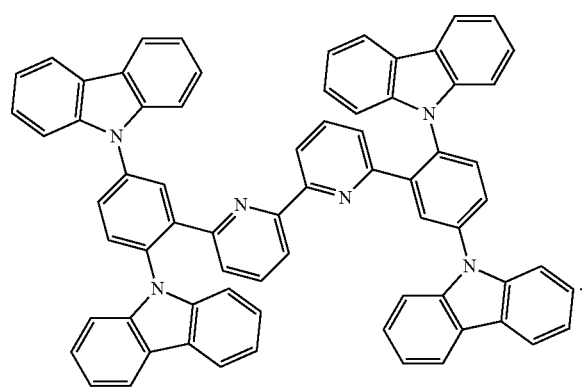

8. An organic compound, which is represented by the following structural formula:

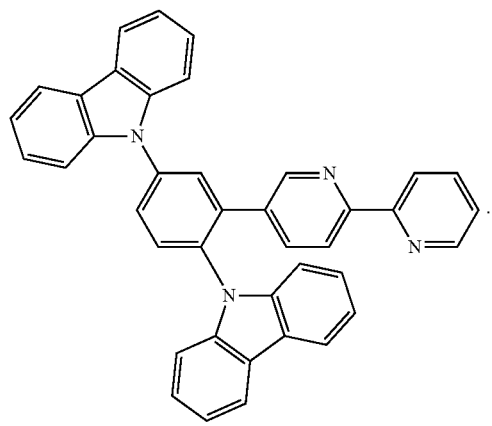

9. An organic compound, which is represented by the following structural formula:

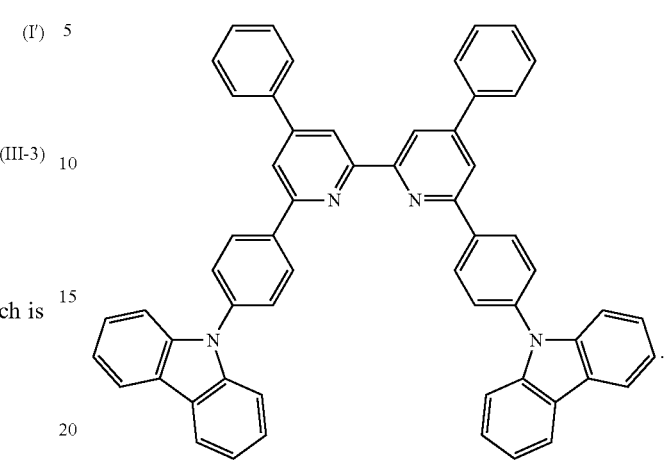

10. The organic compound according to claim 1, which is represented by the following structural formula:

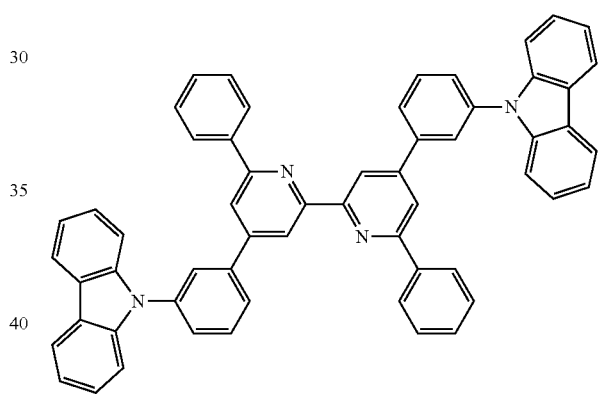

11. The organic compound according to claim 1, which is represented by the following structural formula:

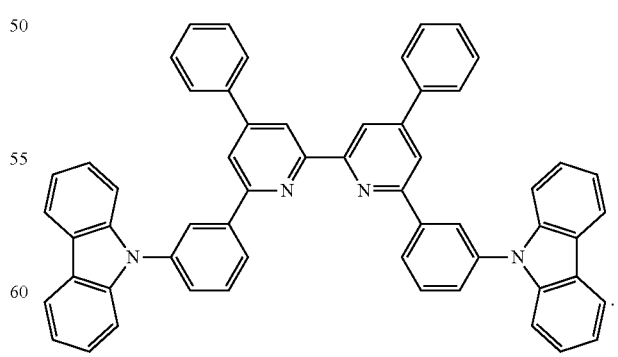

12. The organic compound according to claim 1, which is represented by the following structural formula:

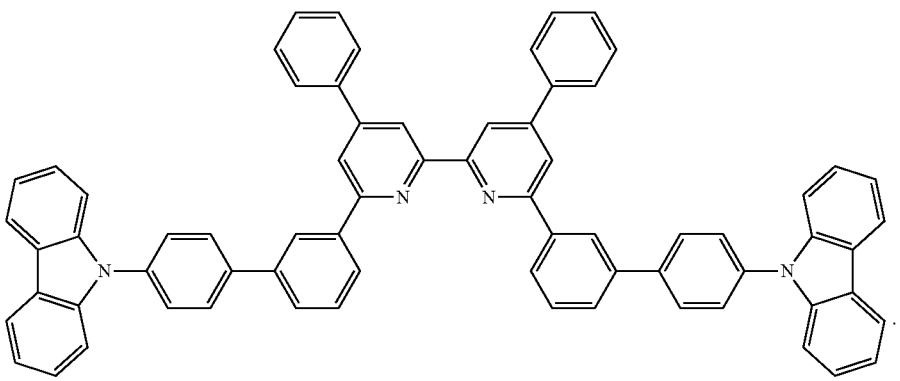

13. An organic compound, which is represented by the following structural formula:

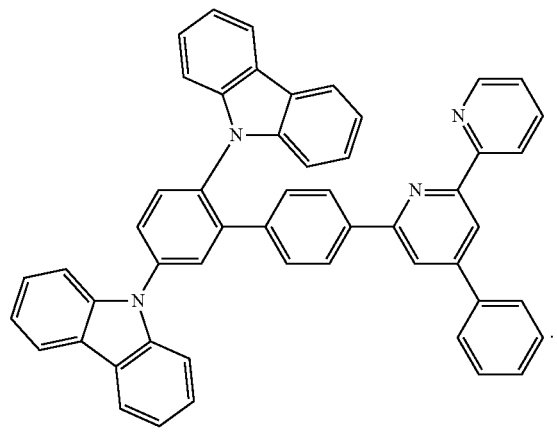

14. A charge transporting material comprising the organic compound of claim 1.

15. An organic electroluminescent device comprising a substrate bearing an anode, a cathode, and an organic light-emitting layer arranged between the two electrodes, wherein the organic electroluminescent device includes a layer containing the organic compound of claim 1 between the anode and the cathode.

* * * * *